US010919882B2

(12) United States Patent
Al-Abed et al.

(10) Patent No.: US 10,919,882 B2
(45) Date of Patent: Feb. 16, 2021

(54) COMPOUNDS FOR USE IN SYNTHESIS OF PEPTIDOMIMETICS

(71) Applicant: THE FEINSTEIN INSTITUTES FOR MEDICAL RESEARCH, Manhasset, NY (US)

(72) Inventors: Yousef Al-Abed, Manhasset, NY (US); Kai Fan Cheng, Manhasset, NY (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 0 days.

(21) Appl. No.: 16/869,794

(22) Filed: May 8, 2020

(65) Prior Publication Data

US 2020/0354344 A1      Nov. 12, 2020

Related U.S. Application Data

(60) Provisional application No. 62/845,617, filed on May 9, 2019.

(51) Int. Cl.
*C07D 403/12* (2006.01)
*C07K 1/06* (2006.01)

(52) U.S. Cl.
CPC .......... *C07D 403/12* (2013.01); *C07K 1/061* (2013.01)

(58) Field of Classification Search
CPC .............................. C07D 403/12; C07K 1/061
USPC ......................................................... 548/259
See application file for complete search history.

(56) References Cited

U.S. PATENT DOCUMENTS

| 5,602,231 | A | * | 2/1997 | Cotton | C07K 7/06 530/334 |
|---|---|---|---|---|---|
| 8,563,565 | B2 | | 10/2013 | Norimine et al. | |
| 9,186,371 | B2 | | 11/2015 | Taniguchi et al. | |
| 2006/0281686 | A1 | | 12/2006 | Lopez Areiza et al. | |
| 2011/0086836 | A1 | | 4/2011 | Soeberdt et al. | |
| 2018/0344808 | A1 | | 12/2018 | Tracey et al. | |
| 2019/0055283 | A1 | | 2/2019 | Ekici et al. | |

FOREIGN PATENT DOCUMENTS

WO    WO 2016/094899 A2    6/2016

OTHER PUBLICATIONS

International Search Report dated Sep. 2, 2020, from corresponding International Application No. PCT/US20/31998.
Written Opinion of the International Searching Authority dated Sep. 2, 2020, from corresponding International Application No. PCT/US20/31998.
PubChem CID-136595533 "(2,5-Dioxopyrrol-1-yl) N-(2,5-dihydroxpyrrol-1-yl)-N-(1,3-dioxoisoindol-2-yl)carbamate" Created on Jan. 4, 2019.
PubChem CID-132255576 "(2S)-2-(Imidazole-1-carbonylamino)pentanedioic acid" Created on Jan. 29, 2018.
International Search Report dated Jul. 31, 2020, from corresponding International Application No. PCT/US20/32025.
Written Opinion of the International Searching Authority dated Jul. 31, 2020, from corresponding International Application No. PCT/US20/32025.
Yang et al. "MD-2 is required for disulfide HMGB1-dependent TLR4 signaling" The Journal of Experimental Medicine; Published on Jan. 5, 2015; vol. 212; p. 5-14.
Sun et al. "Folic acid derived-P5779 mimetics regulate DAMP-mediated inflammation through disruption of HMGB1:TLR4:MD-2 axes" PLOS ONE; Published on Feb. 15, 2018; vol. 13; p. 1-14.
International Search Report dated Sep. 10, 2020, from corresponding International Application No. PCT/US20/31992.
Written Opinion of the International Searching Authority dated Sep. 10, 2020, from corresponding International Application No. PCT/US20/31992.
PubChem CID-519335 "Methanethioic S-acid" Created on Mar. 27, 2005.
Heffeter et al. "Anticancer Thiosemicarbazones: Chemical Properties, Interaction with Iron Metabolism, and Resistance Development" Antioxidants & Redox Signaling; vol. 30, No. 8, 2019.
International Search Report dated Sep. 16, 2020, from corresponding International Application No. PCT/US20/31988.
Written Opinion of the International Searching Authority dated Sep. 16, 2020, from corresponding International Application No. PCT/US20/31988.
PubChem CID-67548889 "Methyl (2S)-1-(imidazole-1-carbonyl)pyrrolidine-2-carboxylate" Created on Nov. 30, 2012.
PubChem CID-1089188 "(2S)-1-(1-Imidazolylcarbonyl)pyrrolidine-2-carboxylic acid benzyl ester" Created on Oct. 26, 2006.

* cited by examiner

*Primary Examiner* — Kristin A Vajda
(74) *Attorney, Agent, or Firm* — Davidson, Davidson & Kappel, LLC

(57) ABSTRACT

Synthesis of O-benzotriazole and O-imidazole synthons are described. Uses of synthons in synthesis of azapeptides and other peptidomimetics, azapeptides and other peptidomimetics synthesized from the synthons and uses of azapeptides and other peptidomimetics are also described.

21 Claims, 3 Drawing Sheets

COMPOUNDS FOR USE IN SYNTHESIS OF PEPTIDOMIMETICS

This application claims the benefit of U.S. Provisional Application No. 62/845,617, filed on May 9, 2019, hereby incorporated by reference.

FIELD OF THE INVENTION

The present invention is directed to compounds for use in synthesis of azapeptides and other aza-amino acid conjugates; synthesis of azapeptides and other aza-amino acid conjugates, and uses of azapeptides and other aza-amino acid conjugates in drug discovery, diagnosis, prevention, inhibition, and treatment of diseases.

BACKGROUND OF THE INVENTION

The in vitro and in vivo stability and in vitro and in vivo half-lives of peptides are limited, e.g., by their rate of hydrolysis and enzymatic degradation.

Azapeptides are analogs of peptides. An azapeptide contains a substituted semicarbazide instead of one or more of the amino acid residue(s) of the parent peptide. In other words, one or more of α-carbon atom(s) of the parent peptide are replaced with a nitrogen atom in the azapeptide. As compared to the parent peptides, azapeptides are hydrolysed and degraded by enzymes at a slower rate.

Aza-amino acids have not been ideal synthons for use in synthesis of azapeptides and other aza-amino acid conjugates. As compared to the parent peptides, azapeptides contain a nitrogen atom instead of one or more of α-carbon atom(s). Due, to the reduced reactivity of the carbonyl moiety in the aza-amino acid residue relative to a natural amino acid counterpart, an aza-peptide bond is more stable under the effect of peptidases. Thus, azapeptides are hydrolysed and degraded by peptidases at a slower rate and exhibit, e.g., an improved metabolic stability, than the parent peptides.

Nevertheless, the rate of formation of the aza-peptide bond is much slower than that of a typical peptide bond. Consequently, there is a greater potential of formation of unwanted side products during azapeptide synthesis with aza-amino acids than with conventional amino acids. An additional obstacle in utilizing aza-amino acids in syntheses of azapeptides is the orthogonal functionalization of the two available nitrogen atoms in the hydrazine system. For these and other reasons, syntheses of azapeptides with aza-amino acids and conventional coupling agents was challenging prior to the present invention.

There is a need for compounds which overcome the limitations of conventional aza-amino acids and/or allow, e.g., for a faster and/or cheaper and/or more efficient synthesis of azapeptides and other aza-amino acid conjugates.

SUMMARY OF THE INVENTION

It is an object of the invention to provide compounds for synthesis of azapeptides and other aza-amino acid conjugates.

It is another object of the invention to provide azapeptides and other aza-amino acid conjugates that are more stable and/or more efficacious than their parent peptides.

It is yet an additional object of the invention to provide azapeptide diagnostic and therapeutic agents.

In connection with the above objects and others, the invention is directed to compounds of Formula (IA):

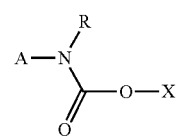

(IA)

wherein A is N-phthalimidyl (NPhth) or $NR_1R_2$, $R_1$ is H, $R_2$ is tert-butoxycarbonyl (Boc), 9-fluorenylmethoxycarbonyl (Fmoc), 2-(3,5-dimethoxyphenyl)propan-2-yloxycarbonyl (Ddz), or R and $R_1$ or $R_2$ are connected and together form a side chain radical of proline;

X is a heteroaryl; and

R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, serine, and glutamine. The heteroaryl may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or —$NH_3$. In certain embodiments, the heteroaryl is substituted with —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. In certain embodiments, the heteroaryl is an imidazolyl or a benzotriazolyl. Imidazolyl or benzotriazolyl may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or —$NH_3$. In certain embodiments, imidazolyl or benzotriazolyl is substituted with —$CF_3$. Compounds of Formula (IA) could be used as building blocks or synthons for synthesis of azapeptides and other peptidomimetics.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is imidazolyl or benzotriazolyl; and

R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, and glutamine. Imidazolyl and benzotriazolyl may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or —$NH_3$. In certain embodiments, the imidazolyl and benzotriazolyl are substituted with —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is imidazolyl substituted with —$CF_3$, —$CHF_2$, —$CH_2F$, —$CBr_3$, —$CHBr_2$, —$CH_2Br$, —$CCl_3$, —$CHCl_2$, —$CH_2Cl$; and R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (IA) is a compound in which

A is N-phthalimidyl or $NR_1R_2$, $R_1$ is H, $R_2$ is tert-butoxycarbonyl, 9-fluorenylmethoxycarbonyl, 2-(3,5-dimethoxyphenyl)propan-2-yloxycarbonyl;

X is benzotriazolyl substituted with —$CF_3$, —$CHF_2$, —$CH_2F$, —$CBr_3$, —$CHBr_2$, —$CH_2Br$, —$CCl_3$, —$CHCl_2$, or —$CH_2Cl$; and R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine.

In certain embodiments, a compound of Formula (IA) is a compound in which X is imidazolyl or benzotriazolyl, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, a compound of Formula (IA) is a compound in which X is imidazolyl substituted with —$CF_3$, —$CHF_2$, —$CH_2F$, —$CBr_3$, —$CHBr_2$, —$CH_2Br$, —$CCl_3$, —$CHCl_2$, or —$CH_2Cl$, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, a compound of Formula (IA) is a compound in which X is benzotriazolyl substituted with —$CF_3$, —$CHF_2$, —$CH_2F$, —$CBr_3$, —$CHBr_2$, —$CH_2Br$, —$CCl_3$, —$CHCl_2$, or —$CH_2Cl$, and (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl, and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

In certain embodiments, compound of Formula (IA) is a compound in which $R_1$ and R are $CH_2CH_2CH_2$, and $R_2$ is tert-butoxycarbonyl, 9-fluorenylmethoxycarbonyl, 2-(3,5-dimethoxyphenyl)propan-2-yloxycarbonyl, and X is imidazolyl or benzotriazolyl.

In certain embodiments, compound of Formula (IA) is a compound in which $R_1$ and R are $CH_2CH_2CH_2$, and $R_2$ is tert-butoxycarbonyl, 9-fluorenylmethoxycarbonyl, 2-(3,5-dimethoxyphenyl)propan-2-yloxycarbonyl, and X is imidazolyl or benzotriazolyl.

The invention is also directed in part to compounds of Formula (IA):

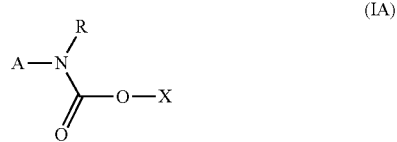

(IA)

wherein

X is imidazolyl or benzotriazolyl, and wherein (i) A and R are connected and form a side chain of proline, or (ii) A is hydrogen, or a protecting group comprising phthalimidyl, tert-butoxycarbonyl, 9-fluorenylmethoxycarbonyl, 2-(3,5-dimethoxyphenyl)propan-2-yloxycarbonyl; and R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, cysteine, serine, threonine, and glutamine.

Compounds of Formula (IA) could be used in drug discovery and/or as building blocks or synthons for synthesis of azapeptides and other peptidomimetics.

The invention is also directed in part to compounds of Formula (IB):

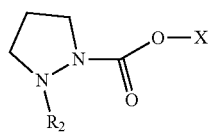

(IB)

wherein $R_2$ is a protecting group (e.g., tert-butoxycarbonyl, 9-fluorenylmethoxycarbonyl, 2-(3,5-dimethoxyphenyl)propan-2-yloxycarbonyl), and X is imidazolyl or benzotriazolyl. Compounds of Formula (IB) could be used in drug discovery and/or as building blocks or synthons for synthesis of azapeptides and other peptidomimetics.

In certain embodiments, the invention is directed to Phth-protected carbamoyl aza-imidazole derivatives and Phth-protected carbamoyl aza-benzotriazole derivatives of unnatural amino acids, including, e.g., aza-imidazole derivatives and Phth-protected carbamoyl aza-benzotriazole derivatives of β-amino acids (e.g., L-β-homotyrosine, β-alanine, L-β-homoasparagine, L-β-homoalanine, L-β-homophenylalanine, L-β-homoproline, L-β-holysine, L-β-homorarginine, L-β-proline, etc.), aliphatic amino acids (e.g., 6-aminohexanoic acid, 2-amino-3-methoxybutanoic acid, 1-aminocyclopentane-1-carboxylic acid, 2-(aminooxy)acetic acid, 6-aminohaxanoic acid, 2-[2-(amino)-ethoxy]-ethoxy}acetic acid), β-cyclohexyl-L-alanine, 6-aminohexanoic acid, L-α,β-diaminopropionic acid, L-propargylglycinel, L-α,β-diaminopropionic acid, α-aminoisobutyric acid, β-(2-pyridyl)-L-alanine, β-(3-pyridyl)-L-alanine, 3-cyclopropyl-L-alanine, β-t-butyl-L-alanine, (2,4-dinitrophenyl))-L-α,β-diaminopropionic acid, (allyloxycarbonyl)-L-α,β-diaminopropionic acid, D-α,β-diaminopropionic acid, L-α,β-diaminopropionic acid, (N-γ-1-(4,4-dimethyl-2,6-dioxocyclohex-1-ylidene)ethyl)-L-α,γ-diaminobutyric acid, (N-γ-4-methyltrityl)-L-α,γ-diaminobutyric acid, L-α,γ-diaminobutyric acid, 4-fluoro-L-phenylglycine, 5,5,5-trifluoro-DL-leucine, epsilon-aminohexanoic-OH, L-α-t-butylglycine, L-2-amino-3-(dimethylamino)propionic acid, L-2-aminocaproic acid, L-allylglycine, lysine azide, (Nδ-4-methyltrityl)-L-ornithine, Arg(Me)(Pbf)-OH, dimethyl-L-arginine (symmetrical and unsymmetrical), L-2-amino-3-guanidinopropionic acid, L-citrulline, ε-acetyl-L-lysine, Lys(ivDde)-OH, Lys(Me)2-OH•HCl, Lys(Me3)-OHchloride, α-methyl-DL-glutamic acid, γ-carboxy-L-glutamic acid γ,γ-di-t-butyl ester, (N-γ-ethyl)-L-glutamine, 2,6-diaminopimelic acid, Glu(OA11)-OH, L-cysteic acid, α-methyl-DL-methionine, DL-buthionine, L-cysteic acid, L-selenomethionine, S-[2-(4-pyridyl)ethyl]-L-cysteine, S-[2-(4-pyridyl)ethyl]-L-cysteine, S-diphenylmethyl-L cysteine, S-trityl-L-homocysteine, S-trityl-L-penicillamine, (Se-p-methoxybenzyl)-L-selenocysteine, β-hydroxyphenylalanine, 2-cyano-L-phenylalanine, L-thyroxine, O-methyl-L-tyrosine, β-methyl-DL-phenylalanine, 2-cyano-L-phenylalanine, L-thyroxine, O-methyl-L-tyrosine, β-methyl-DL-phenylalanine, 2-cyano-L-phenylalanine, 3,4-dichloro-L-phenylalanine, 3,4-difluoro-L-phenylalanine, 3,4-dihydroxy-L-phenylalanine, 3,4-dihydroxy-phenylalanine, 3-amino-L-tyrosine, 3-chloro-L-tyrosine, 3-fluoro-DL-tyrosine, 3-nitro-L-tyrosine, 4-amino-L-phenylalanine, 4-aminomethyl-L-phenylalanine, 4-(phosphonomethyl)-phenylalanine, 4-benzoyl-D-phenylalanine, 4-bis(2-chloroethyl)amino-L-phenylalanine, 4-cyano-L-phenylalanine, 4-fluoro-L-phenylalanine, 4-iodo-L-phenylalanine, DL-m-tyrosine, 2,6-dimethyl-tyrosine, L-homophenylalanine, O-methyl-L-tyrosine, Phe(4-guanidino) OH, O-benzyl-L-phosphotyrosine, (2S,3R)-3-phenylpyrrolidine-2-carboxylic acid, (2S,4S)-4-phenylpyrrolidine-2-carboxylic acid, (2S,3aS,7aS)-Octahydro-1H-indole-2-carboxylic acid, (2S,3R)-3-phenylpyrrolidine-2-carboxylic acid, (2S,4R)-(−)-4-t-butoxypyrrolidine-2-carboxylic acid, trans-4-Fluoro-L-proline, (3S,4S)-4-amino-3-hydroxy-6-methylheptanoic acid, 4-amino-3-hydroxybutanoic acid, L-α-methylserine, (2S,3S)-2-amino-3-methoxybutanoic acid, Thr(β-D-GlcNAc(Ac)3)-OH, O-benzyl-L-phosphoserine, O-benzyl-D-phosphothreonine, O-benzyl-L-phosphothreonine, 4-methyl-DL-tryptophan, 6-fluoro-DL-tryptophan, 6-methyl-DL-tryptophan, DL-7-azatryptophan, (R)-7-Azatryptophan, 5-benzyloxy-DL-tryptophan, 5-bromo-DL-tryptophan, 5-chloro-DL-tryptophan, 5-fluoro-DL-tryptophan, 5-hydroxy-L-tryptophan, 5-methoxy-L-tryptophan, 6-chloro-L-tryptophan, 6-methyl-DL-tryptophan, 7-methyl-DL-tryptophan, DL-7-azatryptophan, 5-azido-pentanoic acid, 2-Amino-N-(3-azidopropyl)-3-mercaptopropionamide, 2-Amino-N-(3-azidopropyl)-3-mercaptopropionamide, Azidohomoalanine, L-propargylglycine•DCHA, azidolysine, p-azidophenylalanine, Azidohomoalanine, D-propargylglycine, L-propargylglycine, azidolysine, Tris[(1-benzyl-1H-1,2,3-triazol-4-yl)methyl] amine, 2-(7'-octenyl) alanine, 2-(4'-pentenyl) alanine, 2-(4'-pentenyl)glycine, 2-(7'-octenyl) alanine, [5-((2-Aminoethyl)amino)naphthalene-1-sulfonic acid], L-glutamic acid-γ-[2-(1-sulfonyl-5-naphthyl)-aminoethylamide], N-ε-(5-carboxyfluorescein)-L-lysine, N-ε-(5/6-carboxyfluorescein)-L-lysine, N-ε-(4,4-dimethylazobenzene-4' carbonyl)-L-lysine, Nε-2,4-dinitrophenyl-L-lysine, N-ε-[(7- methoxycoumarin-4-yl)-acetyl-L-lysine, glycosylated amino acids (e.g., Ser(β-D-GlcNAc(Ac)3)-OH, Thr(β-D-GlcNAc(Ac)3)—OH), 3-azabicyclo[3.1.0]hexane-2-carboxylic acid, 4-amino-(1-carboxymethyl) piperidine, 4-phenylpiperidine-4-carboxylic acid, Nα-methyl-N-im-trityl-L-histidine, Nα-methyl-O-benzyl-L-serine dicyclohexylammonium salt, Nalpha-methyl-Nomega-(4-methoxy-2,3,6-trimethylbenzenesulfonyl)-L-arginine, Nalpha-methyl-L-leucine, Nalpha-methyl-L-norvaline, Nalpha-methyl-L-phenylalanine, Nalpha-methyl-N-im-trityl-L-histidine, Nalpha-methyl-O-t-butyl-L-serine, Nalpha-methylglycine, 21-amino-4,7,10,13,16,19-hexaoxaheneicosanoic acid, {2-[2-(amino)-ethoxy]-ethoxy}acetic acid, 6-Amino-4-oxahexanoic acid, 5-Amino-3-Oxapentamoic Acid, NH-(PEG)10-$CH_2CH_2COOH$, NH-(PEG)12-$CH_2CH_2COOH$, 9-Amino-4; 7-Dioxanonanoic acid, 9-Amino-4; 7-Dioxanonanoic acid, 12-amino-4,7,10-trioxadodecanoic acid, 15-amino-4,7,10,13-tetraoxapentadecacanoic acid, 18-amino-4,7,10,13,16-pentaoxaoctadecanoic acid, 21-amino-4,7,10,13,16,19-hexaoxaheneicosanoic acid, NH-(PEG)8-$CH_2CH_2COOH$, 11-amino-3,6,9-trioxaundecanoic acid, N-(Fmoc-8-amino-3,6-dioxa-octyl) succinamic acid, —N-ε-acetyl-L-lysine, L-citrulline, Arg(Me)(Pbf)-OH, Nω,ω-dimethyl-L-arginine (assymetrical and symmetrical), Lys(Me)2-OH chloride, N-ε,ε-t-methyl-L-lysine, Lys(Me3)-OH chloride, O-benzyl-L-phosphoserine, O-benzyl-D-phosphothreonine, O-benzyl-L-phosphothreonine, O-benzyl-L-phosphotyrosine.

The invention is also directed to compounds of Formula (II):

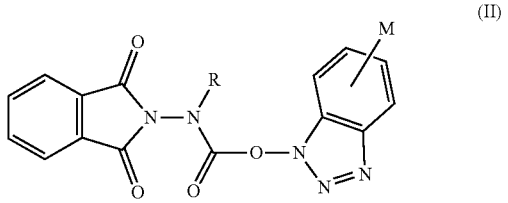

(II)

wherein R is selected from the group consisting of side chain radicals of aspartic acid, phenylalanine, alanine, histidine, glutamic acid, tryptophan, valine, leucine, lysine, methionine, tyrosine, threonine, isoleucine (including, R-isoleucine, S-isoleucine and RS-isoleucine), arginine, glycine, asparagine, serine, and glutamine; and M is an optional substituent selected from the group consisting of a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., —$CF_3$, —$CHF_2$, —$CH_2F$, —$CBr_3$, —$CHBr_2$, —$CH_2Br$, —$CCl_3$, —$CHCl_2$, —$CH_2Cl$), —$NH_2$, or —$NH_3$. In certain embodiments, M is —$CF_3$. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. Compounds of Formula (II) could be used in drug discovery and/or as building blocks or synthons for synthesis of azapeptides and other peptidomimetics.

The invention is also directed to compounds of Formula (III):

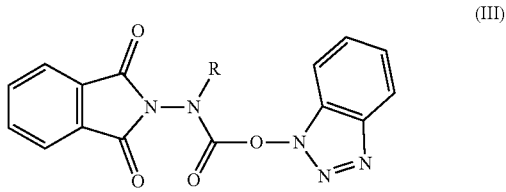

(III)

wherein R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, serine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., N-Phth, N-Boc, N-Fmoc, N-Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. Compounds of Formula (III) could be used in drug discovery, diagnosis, prevention and treatment of diseases, or as building blocks or synthons for synthesis of azapeptides and other peptidomimetics.

The invention is also directed to compounds of Formula (IV):

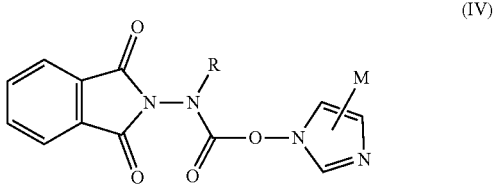

(IV)

wherein R is selected from the group consisting of side chain radicals of aspartic acid, phenylalanine, alanine, histidine, glutamic acid, tryptophan, threonine, valine, leucine, lysine, methionine, tyrosine, isoleucine (including, R-isoleucine, S-isoleucine and RS-isoleucine), arginine, glycine, asparagine, serine, and glutamine. The side chain radicals may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., N-Phth, N-Boc, N-Fmoc, N-Ddz, etc.). In certain embodiments, R is selected from the group consisting of H, methyl, isopropyl, isobutyl, benzyl, and side chain radicals of aspartic acid, histidine, glutamic acid, tryptophan, lysine, methionine, tyrosine, isoleucine (including, R-isoleucine, S-isoleucine and RS-isoleucine), arginine, asparagine, and glutamine. Compounds of Formula (IV) could be used in drug discovery, diagnosis, prevention and treatment of diseases, or as building blocks or synthons for synthesis of azapeptides, e.g., for use in drug discovery, diagnosis, prevention and treatment of diseases.

The invention is further directed to the use of compounds of Formulas (IA), (IB), (II), (III), and (IV) in the preparation of compounds of Formula (V):

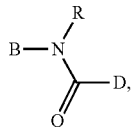

(V)

wherein

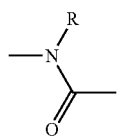

is at the N-terminus and/or the C-terminus and/or at or adjacent to a cleavage or a hydrolysis site of the compound of Formula (V);

wherein B is selected from the group consisting of hydrogen, —NH$_2$, —NNH$_2$, —CONH$_2$, —COORS, —COOH, —COH, —COC$_1$-C$_4$ alkyl, —COC$_1$-C$_4$ haloalkyl, —OH, an amino acid, an aza amino acid, a 2 to 60-mer peptide, a 2 to 60-mer aza peptide, a 2 to 60-mer azatide;

D is selected from the group consisting of —OR$_4$, —OH, —NH$_2$, —NNH$_2$, —NHCOCH$_3$, —NHCH$_3$, —N(CH$_3$)$_2$, —CONH$_2$, —COOH, —COH, —COC$_1$-C$_4$ alkyl, —COC$_1$-C$_4$ haloalkyl, an amino acid, an aza amino acid, a 2 to 60-mer peptide, a 2 to 60-mer aza peptide, a 2 to 60-mer azatide;

R$_3$ and R$_4$ is each independently selected from the group consisting of C$_1$-C$_6$ alkyl (e.g., methyl), methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a C$_1$-C$_6$ alkyl (e.g., methyl), hydroxyl, —COOH, —COH, methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.) Compounds of Formula (V) are azapeptide analogues of compounds of Formula (VI):

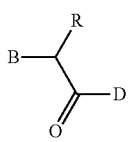

(VI)

wherein B is selected from the group consisting of hydrogen, —NH$_2$, —NNH$_2$, —CONH$_2$, —COOR$_3$, —COOH, —COH, —COC$_1$-C$_4$ alkyl, —COC$_1$-C$_4$ haloalkyl, —OH, an amino acid, an aza amino acid, a 2 to 60-mer peptide, a 2 to 60-mer aza peptide, a 2 to 60-mer azatide;

D is selected from the group consisting of —OR$_4$, —OH, —NH$_2$, —NNH$_2$, —NHCOCH$_3$, —NHCH$_3$, —N(CH$_3$)2, —CONH$_2$, —COOH, —COH, —COC$_1$-C$_4$ alkyl, —COC$_1$-C$_4$ haloalkyl, an amino acid, an aza amino acid, a 2 to 60-mer peptide, a 2 to 60-mer aza peptide, a 2 to 60-mer azatide;

R$_3$ and R$_4$ is each independently selected from the group consisting of C$_1$-C$_6$ alkyl (e.g., methyl), methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a C$_1$-C$_6$ alkyl (e.g., methyl), hydroxyl, —COOH, —COH, methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.). In the preferred embodiments, compounds of Formula (V) are more resistant to hydrolysis and/or enzymatic degradation than compounds of Formula (VI). In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention and treatment of diseases.

The invention is further directed to the use of compounds of Formulas (IA), (IB), (II), (III), and (IV) in the preparation of compounds of Formula (V):

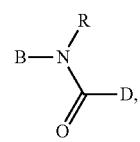

(V)

wherein

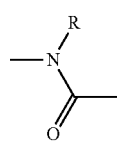

is adjacent to the N-terminus and/or the C-terminus of the compound of Formula (V);

wherein B is selected from the group consisting of hydrogen, —NH$_2$, —NNH$_2$, —CONH$_2$, —COORS, —COOH, —COH, —COC$_1$-C$_4$ alkyl, —COC$_1$-C$_4$ haloalkyl, —OH, an amino acid, an aza amino acid, a 2 to 60-mer peptide, a 2 to 60-mer aza peptide, a 2 to 60-mer azatide;

D is selected from the group consisting of —OR$_4$, —OH, —NH$_2$, —NNH$_2$, —NHCOCH$_3$, —NHCH$_3$, —N(CH$_3$)$_2$, —CONH$_2$, —COOH, —COH, —COC$_1$-C$_4$ alkyl, —COC$_1$-C$_4$ haloalkyl, an amino acid, an aza amino acid, a 2 to 60-mer peptide, a 2 to 60-mer aza peptide, a 2 to 60-mer azatide;

R$_3$ and R$_4$ is each independently selected from the group consisting of C$_1$-C$_6$ alkyl (e.g., methyl), methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a C$_1$-C$_6$ alkyl (e.g., methyl), hydroxyl, —COOH, —COH, methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.) Compounds of Formula (V) are azapeptide analogues of compounds of Formula (VI):

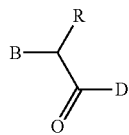

(VI)

wherein B is selected from the group consisting of hydrogen, —NH$_2$, —NNH$_2$, —CONH$_2$, —COOR$_3$, —COOH, —COH, —COC$_1$-C$_4$ alkyl, —COC$_1$-C$_4$ haloalkyl, —OH, an amino acid, an aza amino acid, a 2 to 60-mer peptide, a 2 to 60-mer aza peptide, a 2 to 60-mer azatide;

D is selected from the group consisting of —OR$_4$, —OH, —NH$_2$, —NNH$_2$, —NHCOCH$_3$, —NHCH$_3$, —N(CH$_3$)$_2$, —CONH$_2$, —COOH, —COH, —COC$_1$-C$_4$ alkyl, —COC$_1$-C$_4$ haloalkyl, an amino acid, an aza amino acid, a 2 to 60-mer peptide, a 2 to 60-mer aza peptide, a 2 to 60-mer azatide;

R$_3$ and R$_4$ is each independently selected from the group consisting of C$_1$-C$_6$ alkyl (e.g., methyl), methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a C$_1$-C$_6$ alkyl (e.g., methyl), hydroxyl, —COOH, —COH, methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.). In the preferred embodiments, compounds of Formula (V) are more resistant to hydrolysis and/or enzymatic degradation than compounds of Formula (VI). In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention, inhibition, and treatment of diseases.

In certain embodiments, in compounds of Formula (V) and compounds of Formula (VI), B of each compound is independently selected from the group consisting of hydrogen, —NH$_2$, —NNH$_2$, —CONH$_2$, —COORS, —COC$_1$-C$_4$ alkyl, —COC$_1$-C$_4$ haloalkyl, —OH, an amino acid, an aza amino acid, a 2 to 60-mer peptide, a 2 to 60-mer aza peptide, a 2 to 60-mer azatide;

D of each compound is independently selected from the group consisting of —OR$_4$, —NH$_2$, —NNH$_2$, —NHCOCH$_3$, —NHCH$_3$, —N(CH$_3$)$_2$, —CONH$_2$, —COOH, —COH, —COC$_1$-C$_4$ alkyl, —COC$_1$-C$_4$ haloalkyl, an amino acid, an aza amino acid, a 2 to 60-mer peptide, a 2 to 60-mer aza peptide, a 2 to 60-mer azatide;

R$_3$ and R$_4$ is each independently selected from the group consisting of C$_1$-C$_6$ alkyl (e.g., methyl), methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.); and R of each compound is independently selected from the group consisting of side chain radicals of aspartic acid, phenylalanine, alanine, histidine, glutamic acid, tryptophan, valine, leucine, lysine, serine, threoinine, methionine, tyrosine, isoleucine (including, R-isoleucine, S-isoleucine and RS-isoleucine), arginine, glycine, asparagine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, may be unsubstituted or substituted with one or more of the following: a halogen (Cl, F, or Br), a C$_1$-C$_6$ alkyl (e.g., methyl), hydroxyl, —COOH, —COH, methoxyl, ethoxyl, propoxyl, a C$_1$-C$_6$ haloalkyl (e.g., a chloromethyl, a fluromethyl, etc.) or a protecting group (e.g., Phth, Boc, Fmoc, Ddz, etc.).

The invention is further directed to the use of compounds of Formulas (IA), (IB), (II), (III), and (IV) in the preparation of azabradykinin, including, e.g., aza-7 bradykinin, aza-2,8 bradykinin, aza-2 bradykinin, and aza-8 bradykinin:

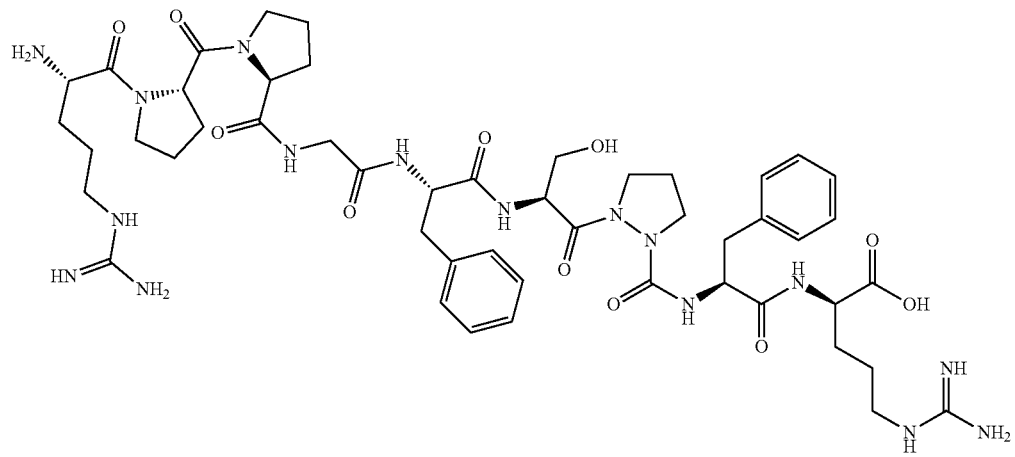
aza-7 bradykinin
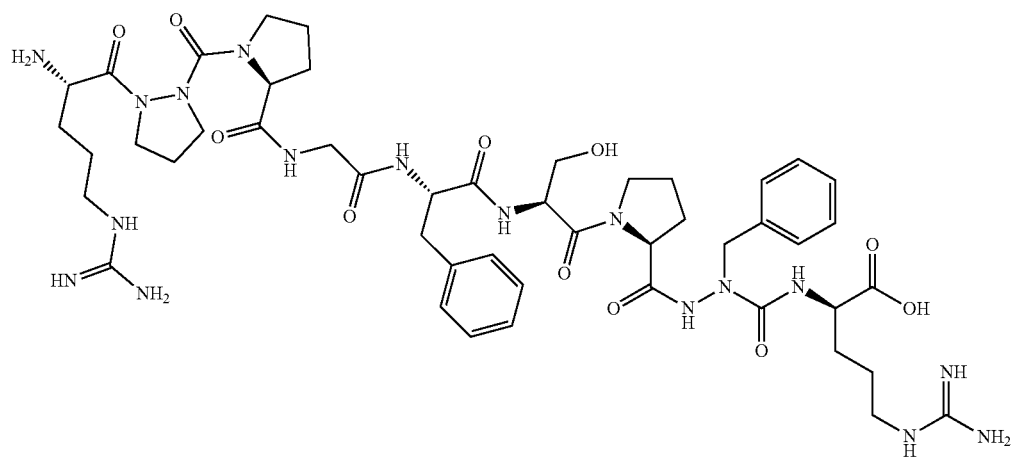
aza-2, 8 bradykinin
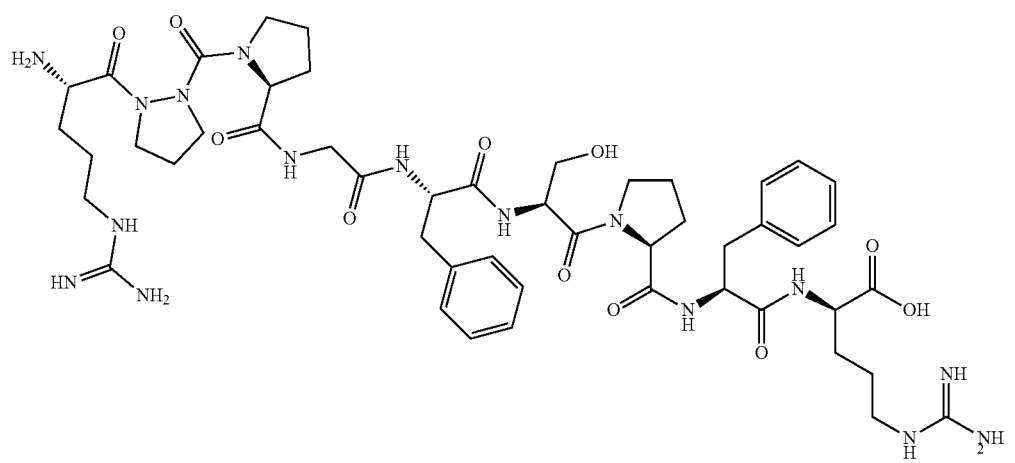
aza-2 bradykinin

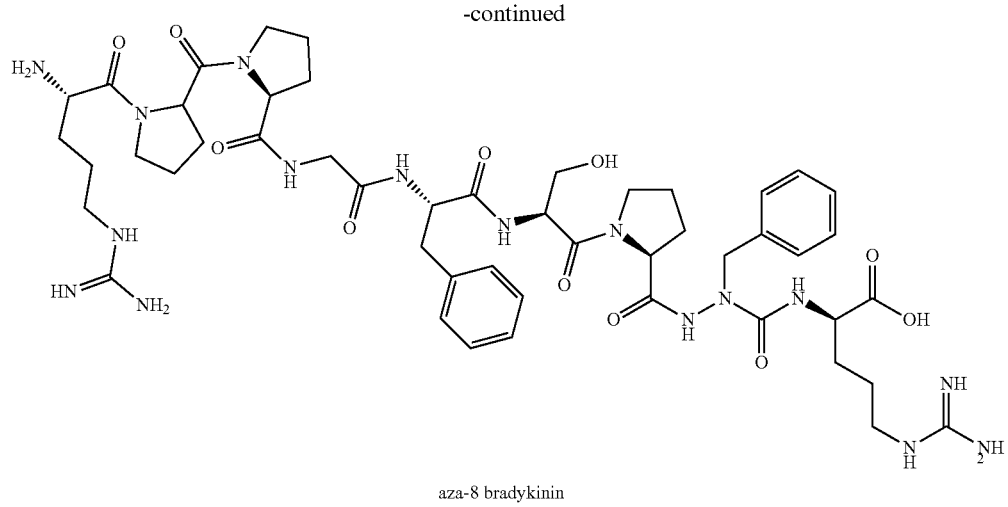

aza-8 bradykinin

The invention is also directed in part to a method of preparing a compound of Formula (V), the method comprising a step of activating a compound of Formula (IA), Formula (IB), Formula (II), Formula (III) or Formula (IV) to form an activated compound of Formula (IA), Formula (IB), Formula (II), Formula (III), or Formula (IV), a step of coupling the activated compound of Formula (IA), Formula (IB), Formula (II), Formula (III), or Formula (IV) with N-terminal of an amino acid, N-terminal of an aza-mino acid, provided that, if a side chain of the amino acid or aza-amino acid contains a group selected from amino, amide, guanidino N, carboxyl, sulfhydryl, carboxyl, hydroxyl, indole, imidazole phenol, the group is protected with a protecting group selected from tert-butoxycarbonyl (Boc), 9-fluorenylmethoxycarbonyl (Fmoc), or 2-(3,5-dimethoxyphenyl)propan-2-yloxycarbonyl (Ddz), phthalimide (Phth), carboxybenzyl (Cbz), 2,2,4,6,7-pentamethyl-dihydrobenzofuran-5-sulfonyl (Pbf), trityl or triphenylmethyl (Trt), t-butyl ester (OtBu), t-butyl ether (tBu), S-t-butyl ether (StBu), allyloxycarbonyl (Aloc), methoxytrimethylbenzene sulfonyl (Mtr), 4,4-dimethyloxybenzhydryl (Mbh), 2,2,5,7,8-pentamethyl-chroman-6-sulfonyl chloride (Pmc), 2,4,6-trimethoxybenzyl (Tmob), allyl ester (OAl), acetamidomethyl (Acm), and the like to form a protected compound of Formula (V), and a step of deprotecting the protected compound of Formula (V), e.g., with hydrazine, piperadine, TFA, acetic acid, thioanisole, EDT, anisole, etc., to form the compound of Formula (V).

In certain embodiments, compounds of Formula (IA), Formula (IB) and Formula (IV) are activated by iodomethane (MeI).

In certain embodiments, the compound of Formula (IA), Formula (IB) and Formula (III) are activated by DIPEA in acetonitrile.

The invention is also directed to a method of preparing an azapeptide comprising a step of activating a compound according to Formula (I); and a step of coupling the activated compound with N-terminal of an amino acid, N-terminal of an aza-mino acid; wherein the azapeptide is a compound of Formula (V). The compound of Formula (I) may be unsubstituted or substituted with one or more of the following: a halogen, a $C_1$-$C_6$ alkyl, hydroxyl, —COOH, —COH, methoxyl, ethoxyl, propoxyl, or a $C_1$-$C_6$ haloalkyl. The

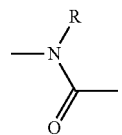

in the compound of Formula (V) may be at the N-terminus and/or the C-terminus of the compound of Formula (V), is adjacent to the N-terminus and/or the C-terminus of the compound of Formula (V) or hydrolysis site of the compound of Formula (V). In some embodiments, the compound of Formula (I) is activated by iodomethane, the coupling is in acetonitrile and comprises addition of DIPEA, and is during solid phase azapeptide synthesis. In additional embodiments, the compound of Formula (I) is activated by iodomethane, the coupling is in acetonitrile and comprises addition of DIPEA, and is during liquid phase azapeptide synthesis.

In the methods of the invention, the azapeptide is preferably prepared in a yield of at least about 40% (by weight) (e.g., from about 45% to about 65%, from about 50% to about 65%, or from about 55% to about 65%, etc.). In certain embodiments, the yield is greater than about 45%, about 50%, about 55%, or about 60%. Thus, the yield may, e.g., be about about 50%, about 55%, about 60%, or about 65%. In certain embodiments, the azapeptide is a di-azapeptide and is synthesized in a yield from about 80% to about 98%.

The invention is also directed in part to a method of preparing a compound of Formula (V), the method comprising a step of coupling a compound of Formula (IA), (IB), (II), (III), or (IV) with an aza-amino acid to form a protected di-azatide, and a step of deprotecting the protected di-azatide, e.g., with hydrazine, TFA, acetic acid, thioanisole, EDT, anisole, a mixture of any of the foregoing, or another de-protecting compound, to form a compound of Formula (V).

The invention is also directed in part to a method of preparing a compound of Formula (V), the method comprising a step of coupling a first compound of Formula (IA), (IB), (II), (III), or (IV) with an amino acid, a second compound of Formula (IA), (IB), (II), (III), or (IV), a peptide, or an azatide in acetonitrile at a temperature from 15° C. to 35° C., wherein the coupling is for a time period from about 20 minutes to about 6 hours, from about 30 minutes to about 5 hours, from about 40 minutes to about 4 hours, from about 50 minutes to about 3 hours, from about 50 minutes to about 2 hours. In some of these embodiments, the coupling is for a time period from about 30 minutes to about 90 minutes at a temperature from about 18° C. to about 25° C. From about 1 to about 3 equivalents of DIPEA and from about 1 equivalents to about 1.4 equivalents (preferably, about 1.1 equivalent) of the amino acid, the second compound of Formula (IA), (IB), (II), (III), or (IV), the peptide, or the azatide may be added to the acetonitrile for the coupling reaction. In some embodiments, no additional reagents are added during the coupling step. In certain embodiments, a compound that is being coupled is an azapeptides with activated carbamoyl imidazole moiety and about 1.5 eq of an amino acid and about 1.0 eq of DIPEA are used, and the coupling is at room temperature under nitrogen for about 20 hours. In certain embodiments, a compound that is being coupled is an azatide with activated carbamoyl imidazole moiety and about 1.5 eq hydrazines and about 1.0 eq DIPEA are used, and the coupling is at about 40° C. under nitrogen for about 20 hours. In certain embodiments, a compound that is being coupled is an azapeptides with carbamoyl benzotriazole (HBt) moiety and about 1.5 eq. of an amino acid and about 2.0 eq. of DIPEA are used, and the coupling is at about 40° C. under nitrogen for about 20 hours. In certain embodiments, a compound that is being coupled is an azapeptide with carbamoyl 1-O-benzotriazole (HOBt) moiety and about 1.1 eq. of an amino acid and about 2.0 eq DIPEA are used, and the coupling is at about 25° C. under nitrogen for 1 hour.

The invention is further directed in part to a solution phase synthesis of the compounds of Formula (V), the solution phase synthesis comprising a step of converting a compound of Formula (IA), (IB), (II), (III), or (IV) to an amide of the compound of Formula (IA), (IB), (II), (III), or (IV), a step of deprotectecting the amide of the compound of Formula (IA), (IB), (II), (III), or (IV), a step of coupling the deprotected amide of Formula (IA), (IB), (II), (III), or (IV) with an additional compound of Formula (IA), (IB), (II), (III), or (IV), or a protected amino acid, or a protected aza-amino acid to form a protected azapeptide, and a step of deprotecting the protected azapeptide to provide a compound of Formula (V).

The invention is further directed in part to a solid phase synthesis of the compounds of Formula (V), the solid phase synthesis comprising a step of coupling a protected compound of Formula (IA), (IB), (II), (III), or (IV) to a support, a step of deprotecting the protected compound of Formula (IA), (IB), (II), (III), or (IV), a step of coupling the deprotected compound of Formula (IA), (IB), (II), (III), or (IV) to an additional protected compound of Formula (IA), (IB), (II), (III), or (IV), an additional protected amino acid, or an additional protected aza-amino acid to form a protected peptide, and a step of deprotecting and cleaving the protected peptide to provide a compound of Formula (V).

The invention is also directed in part to a process of preparing a compound of Formula (V) comprising a step of cleaving a peptide at its N-terminus and/or C-terminus, and a step of coupling the cleaved peptide with a compound of Formula (IA), (IB), (II), (III), or (IV) to form a compound of Formula (V). In certain embodiments, the compound of Formula (IA), (IB), (II), (III), or (IV) is activated prior to the coupling with the cleaved peptide.

The invention is also directed in part to a process of preparing a compound of Formula (V) comprising a step of cleaving a peptide at its cleavage site to form two smaller peptides, a step of replacing the last amino acid of at least one of the smaller peptides with an aza-amino acid to form an azapeptide, and a step of conjugating the azapeptide with the remaining smaller peptide to provide a compound of Formula (V).

The invention is also directed in part to a process of preparing a compound of Formula (V) comprising hydrolizing a peptide at its cleavage site, and reacting the cleaved peptide with a compound of Formula (IA), (IB), (II), (III), or (IV) to provide a compound of Formula (V).

The invention is further directed in part to a method of azapeptide synthesis comprising reacting a compound of Formula (IA), (IB), (II), (III), or (IV) with an aza-amino acid, an amino acid, or a peptide to form the azapeptide, wherein the azapeptide is a compound of formula (V).

The compounds of Formula (IA), (IB), (II), (III), or (IV) and process of the invention allow, e.g., for preparation of a compound of Formula (V) in yields (% by weight) of at least about 40% (e.g., from about 45% to about 65%, from about 50% to about 65%, or from about 55% to about 65%, etc.). In certain embodiments, the yield is greater than about 45%, about 50%, about 55%, or about 60%. Thus, the yield may, e.g., be about 50%, about 55%, about 60%, or about 65%. In certain embodiments, the compound of Formula (V) is a di-azapeptide and is synthesized in a yield from about 80% to about 98%.

DEFINITIONS

The term "about" in the present specification means a value within 15% (±15%) of the value recited immediately after the term "about," including the value equal to the upper limit (i.e., +15%) and the value equal to the lower limit (i.e., −15%) of this range. For example, the phrase "about 100" encompasses any numeric value that is between 85 and 115, including 85 and 115.

An "azapeptide" means a peptide in which one or more α-carbon(s) are replaced by nitrogen trivalent atom(s).

An "azatide" means a peptide in which all α-carbons are replaced by nitrogen trivalent atoms.

An "α-nitrogen" means a nitrogen atom bonded to a carbonyl group in an azapeptide or an azatide. The carbon atom next to the α-nitrogen is called the β-carbon.

An "aza-amino acid" is defined as an amino acid where the chiral α-carbon atom is replaced by a nitrogen atom.

An "azapeptide analogue" means a compound which differs from a peptide that it is an analogue of in that one or more α-carbon atoms of the peptide have been replaced by a nitrogen atom with or without additional structural modification(s) to the side chain(s) of the amino acid residues of the peptide. The one or more α-carbon atoms that are replaced may, e.g., be at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide). Despite having a backbone different from the peptide, the azapeptide analogue preserves, extends and/or improves functional activity of the peptide. The azapeptide analogue is more resistant to degradation than the peptide and/or has an improved therapeutic activity than the peptide and/or has an improved selectivity for a biological receptor than the peptide and/or improved affinity to a biological receptor and/or reversed activity at a biological receptor (agonistic activity instead of antagonist activity or antagonistic activity instead of agonistic activity).

The term "heteroaryl" includes all aryl compounds with atoms other than C and H.

The term "protected" as it is used herein means that one or more group(s) (e.g., —OH) in an amino acid, an aza-amino acid, a peptide, an azapeptide, or a compound is protected with a protecting group (e.g., Phth, Ddz, etc.). Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups include, for example, nitrogen protecting groups and hydroxy-protecting groups. Examples of protective group include, e.g., benzyl, diphenylmethyl, trityl, Cbz, Boc, Fmoc, methoxycarbonyl, ethoxycarbonyl, Phth, Ddz, as well as other protective groups known to those skilled in the art.

A "side chain radical" of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine have the following structures:

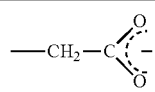

Aspartic Acid

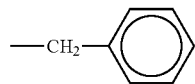

Phenylalanine

Alanine

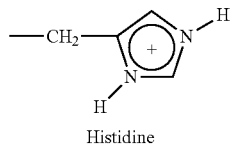

Histidine

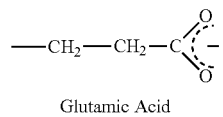

Glutamic Acid

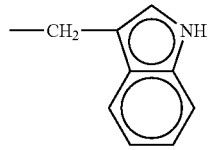

Tryptophan

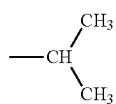

Valine

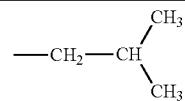

Leucine

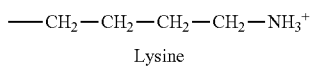

Lysine

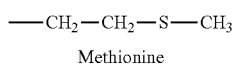

Methionine

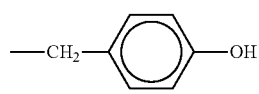

Tyrosine

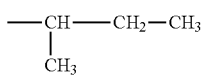

Isoleucine

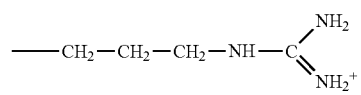

Arginine

Glycine

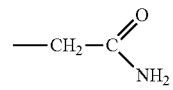

Asparagine

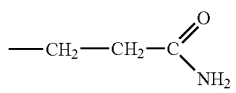

Glutamine

A "side chain radical of proline" is a secondary amine, in that the alpha-amino group is attached directly to the main chain, making the α carbon a direct substituent of the side chain:

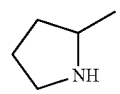

Amino acids which can be used in the present invention are L- and D-amino acids.

Unless otherwise indicated, the terms "prevent," "preventing" and "prevention" contemplate an action that occurs before a patient begins to suffer from the symptoms of specified disease or disorder, which inhibits or reduces the severity of the disease or disorder or of one or more of its symptoms. The terms encompass prophylaxis.

The compounds of the invention can be used in the form of pharmaceutically acceptable salts derived from inorganic or organic acids. For clarity, the term "pharmaceutically acceptable salt[s]" as used herein generally refers to salts prepared from pharmaceutically acceptable acids or bases including inorganic acids and bases and organic acids and bases. Suitable pharmaceutically acceptable base addition salts include, e.g., metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific acids include, e.g., hydrochloric, hydrobromic, phosphoric, sulfuric, and methanesulfonic acids. Examples of specific salts include, e.g., hydrochloride and mesylate salts. Others are well-known in the art. See, e.g., Remington's Pharmaceutical Sciences, 18th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom. In preferred embodiments, methods of diagnosis of the present invention comprise administration of such an isotopically labelled compound.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis- or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Unless otherwise indicated, a "diagnostically effective amount" of a compound is an amount sufficient to diagnose a disease or condition. In general, administration of a compound for diagnostic purposes does not continue for as long as a therapeutic use of a compound, and could be administered only once if such is sufficient to produce the diagnosis.

The term "Phth-protected carbamoyl aza-imidazole derivative of an unnatural amino acid" as used herein means an unnatural aza-amino acid covalently bound (conjugated) to phthalimidyl at its N-terminus and to imidazole at its C-terminus. The unnatural amino acid may be substituted and unsubstituted.

The term "Phth-protected carbamoyl aza-benzotriazole derivative of an unnatural amino acid" as used herein means an unnatural aza-amino acid covalently bound (conjugated) to phthalimidyl at its N-terminus and to benzotriazole at its C-terminus. The unnatural amino acid may be substituted and unsubstituted.

The term "solid-phase synthesis" means a method in which molecules (e.g., amino acids, aza-amino acids, etc.) are covalently bound on a solid support material and synthesised step-by-step in a single reaction vessel utilising selective protecting group chemistry. In this method, building blocks are typically protected at all reactive functional groups. The order of functional group reactions can be controlled by the order of deprotection. For example, in an aza-peptide synthesis, an amino-protected amino acid or an amino-protected aza-amino acid is bound to a solid phase material (e.g., low cross-linked polystyrene beads), forming a covalent bond between the carbonyl group and the resin, e.g., an amido or an ester bond. Then, the amino group is deprotected and reacted with the carbonyl group of the next amino-protected amino acid or amino-protected aza-amino acid. This cycle is repeated to form the desired peptide or aza-peptide chain. After all reactions are complete, the synthesised peptide or aza-peptide is cleaved from the bead.

The terms "solution phase synthesis" and "liquid phase synthesis" means a method in which molecules (e.g., amino acids, aza-amino acids, etc.) are synthesized in a solution without being covalently bound on a solid support material.

The term "synthon" means a building block.

The term "room temperature" means 20° C.

The term "ambient temperature" means 18-28° C.

The terms "parent peptide" and "corresponding peptide" mean a native peptide (i.e., natural or convention peptide) that differs from an azapeptide in that one or more of the amino residue(s) of the native peptide is (are) replaced by a semicarbazide or a substituted semicarbazide (i.e., one or more α-carbon(s) of the native peptide are replaced by nitrogen trivalent atom(s)) in the azapeptide. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

The term "phthalimidyl" means:

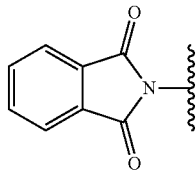 [SMILES: *N1C(=O)c2ccccc2C1=O]

The term "phthaloyl" means:

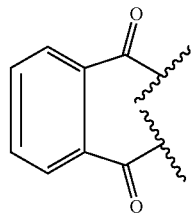 [SMILES: *C(=O)c1ccccc1C(*)=O]

The abbreviation "N-Phth" means "N-phthalimidyl."
The abbreviation "Boc" means "tert-butoxycarbonyl."
The abbreviation "Fmoc" means "9-fluorenylmethoxycarbonyl."
The abbreviation "Ddz" means "2-(3,5-dimethoxyphenyl)propan-2-yloxycarbonyl."
The abbreviation "HOBt" means "1-OH-Benzotriazole."
The abbreviation "SPPS" means "Solid Phase Peptide Synthesis."
The abbreviation "TCCA" means "trichloroisocyanuric acid."
The abbreviation "TBACl" means "tetrabutyl ammonium chloride."
The abbreviation "Phth" means "phthaloyl."
The abbreviation "Cbz" means "carboxybenzyl."
The abbreviation "Pbf" means "2,2,4,6,7-pentamethyldihydrobenzofuran-5-sulfonyl."
The abbreviation "Trt" means "trityl or triphenylmethyl."
The abbreviation "OtBu" means "O-t-butyl."
The abbreviation "tBu" means "t-butyl."
The abbreviation "StBu" means S-t-butyl ether.
The abbreviation "Aloc" means "allyloxycarbonyl."
The abbreviation "Mtr" means "methoxytrimethylbenzene sulfonyl."
The abbreviation "Mbh" means "4,4-dimethyloxybenzhydryl."
The abbreviation "Pmc" means "2,2,5,7,8-pentamethylchroman-6-sulfonyl chloride."
The abbreviation "Tmob" means 2,4,6-trimethoxybenzyl.
The abbreviation "OAl" means "allyl ester."
The abbreviation "Acm" means "acetamidomethyl."
The abbreviation "DEAD" means "Diethyl Azodicarboxylate" (IUPAC name N-ethyl-N-propan-2-ylpropan-2-amine).

In peptide chemistry, "deprotection" refers to a process of removing the protecting groups (e.g., phthaloyl, Boc, Cbz, Fmoc, etc) by a chemical agent. For example, Boc protecting group could be removed under acidic conditions (e.g., 4M HCl, or neat trifluoroacetic acid TFA); Fmoc protecting group could be removed under basic conditions when pH is higher than 12 (20% pipyridine/DMF or DCM); and Phthaloyl group can be cleaved, e.g., under basic conditions or by the use of hydrazine.

DETAILED DESCRIPTION

Figure 1:
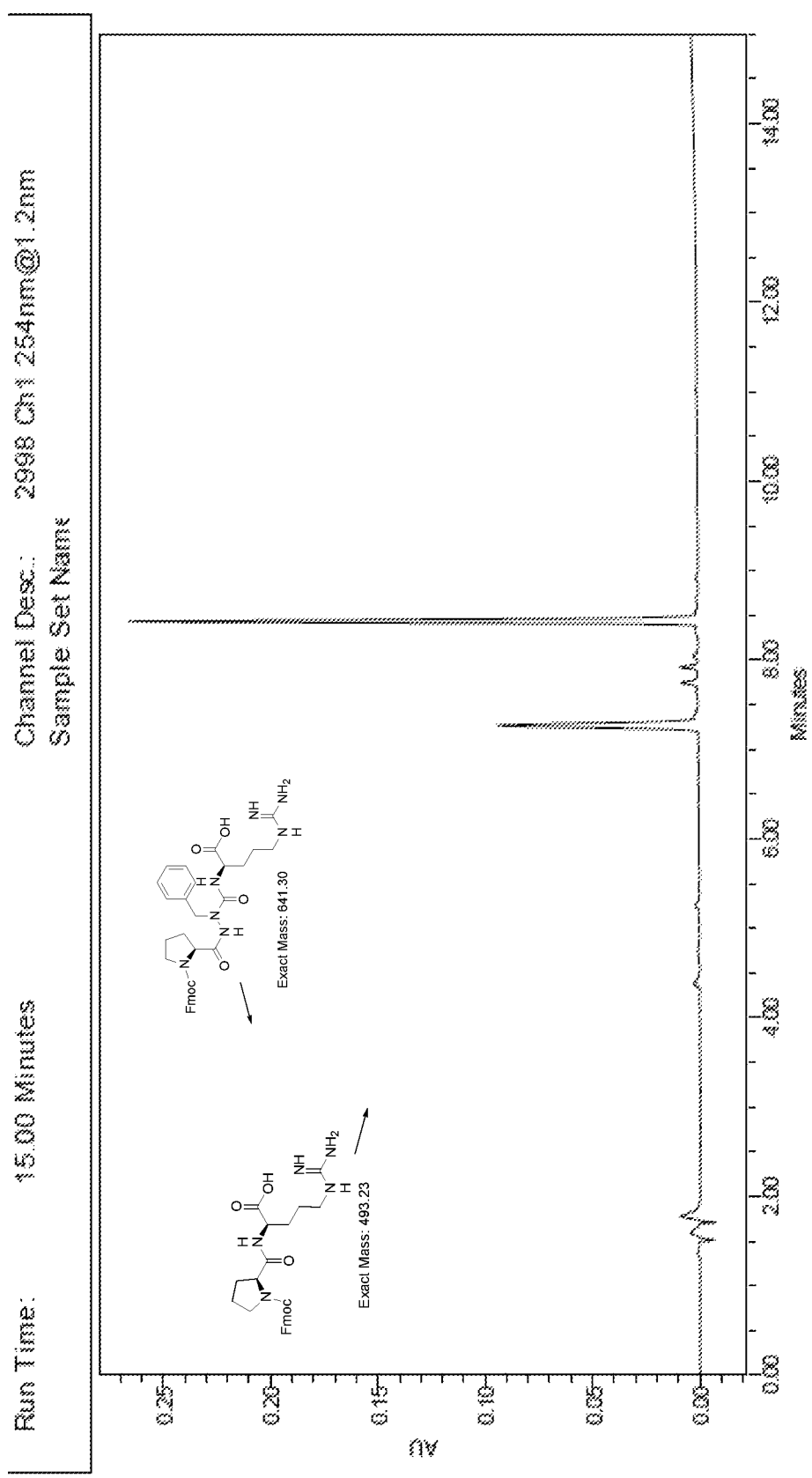
FIG. 1 is HPLC of the intermediate (M=641) with side product (M=493) from SPPS of Example 15.

A replacement of one or more α-carbon(s) with nitrogen in a peptide converts the peptide to an "azapeptide"; and replacement of all α-carbon(s) with nitrogen(s) in a peptide converts the peptide to an "azatide."

Azapeptides and azatides are peptidomimetics and are generally more resistant to enzymatic hydrolysis than corresponding peptides. The increase in resistance to enzymatic degradation may lead to increased metabolic stability of the compounds and/or an improved receptor binding (e.g., an improved affinity to the receptor). Therefore, azapeptides and azatides are useful tools for drug design, applications in medicinal chemistry, and in diagnosis, prevention and treatment of diseases, and may be used, e.g., instead of peptides, as azapeptide analogues ("peptidomimetics").

Compounds of Formula (IA), (IB), (II), (III), and (IV) of the present invention could be used as "building blocks" or synthons for the synthesis of azapeptides and other peptidomimetics and aza-amino acid conjugates, including compounds of Formula (V) in a solution phase synthesis, a solid phase synthesis or a synthesis comprising both a solution phase synthesis and a solid phase synthesis.

Compounds of Formula (IA), (IB), (II), and (III)

Compounds of Formula (IA), (IB), (II), and (III) are stable at 37° C. in an aqueous medium (e.g., an aqueous solution) with a pH of about 7 (e.g., distilled water) for at least 30 minutes, 60 minutes, 90 minutes, 1 hour, 2 hours, 3 hours, 4 hours or 5 hours.

Compounds of Formula (IA), (IB), (II), and (III) may be used as building blocks or synthons for synthesis of azapeptides and other peptidomimetics and aza-amino acid conjugates. The resulting azapeptides and peptidomimetics may have utility in drug discovery, diagnosis, prevention, inhibition, and treatment of diseases.

In certain embodiments, compounds of Formula (IA), (IB), (II), and (III) are selected from the group consisting of:

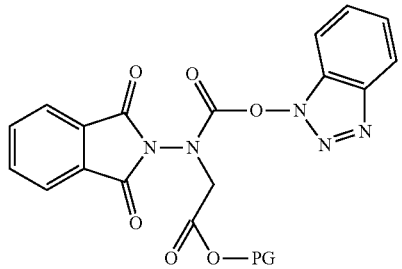

25
-continued
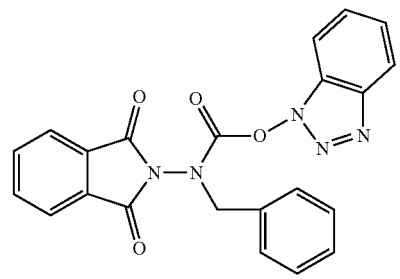 [SMILES: O=C(On1nnc2ccccc21)N(Cc1ccccc1)N1C(=O)c2ccccc2C1=O]
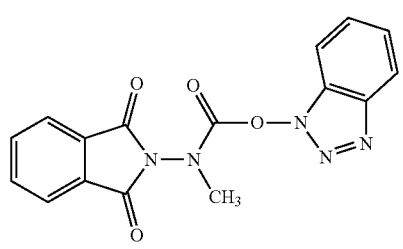 [SMILES: CN(C(=O)On1nnc2ccccc21)N1C(=O)c2ccccc2C1=O]
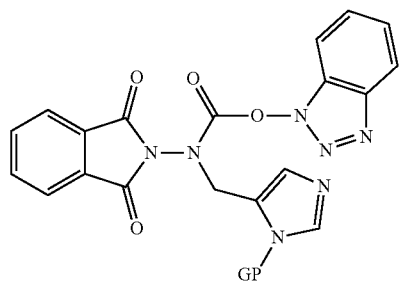
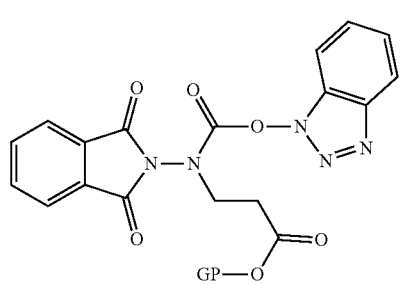
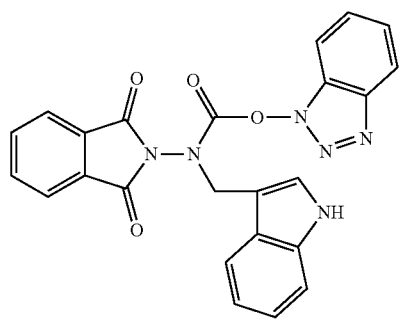 [SMILES: O=C(On1nnc2ccccc21)N(Cc1c[nH]c2ccccc12)N1C(=O)c2ccccc2C1=O]
26
-continued
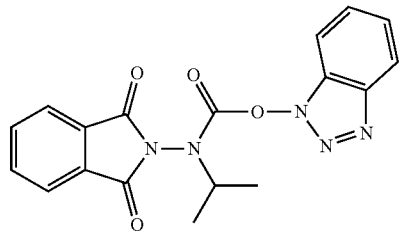 [SMILES: CC(C)N(C(=O)On1nnc2ccccc21)N1C(=O)c2ccccc2C1=O]
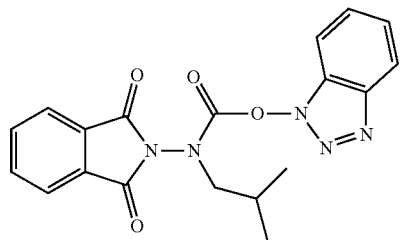 [SMILES: CC(C)CN(C(=O)On1nnc2ccccc21)N1C(=O)c2ccccc2C1=O]
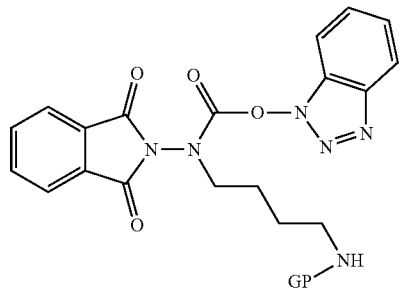
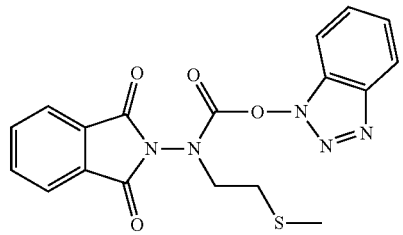 [SMILES: CSCCN(C(=O)On1nnc2ccccc21)N1C(=O)c2ccccc2C1=O]
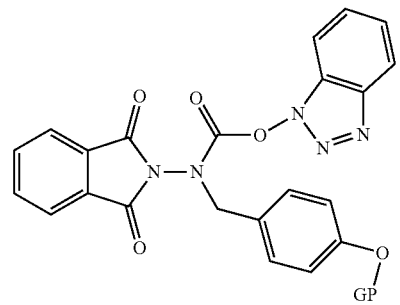
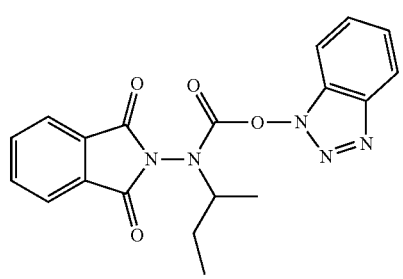 [SMILES: CCC(C)N(C(=O)On1nnc2ccccc21)N1C(=O)c2ccccc2C1=O]

-continued

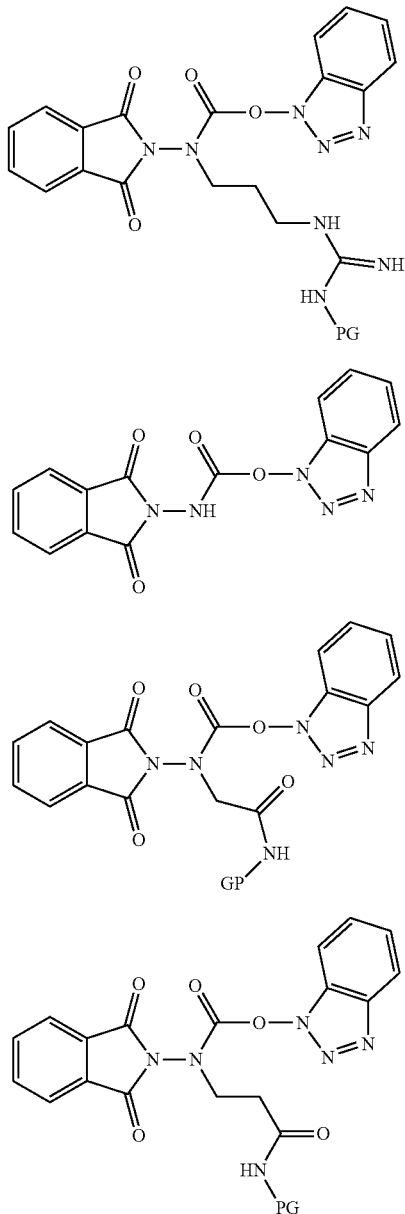

and pharmaceutically acceptable salts thereof, wherein "PG" is H or a protecting group (e.g., Phth, Boc, Fmoc, Ddz, etc.).

In certain embodiments, compounds of Formula (IA), (IB), (II), and (III) are selected from the group consisting of N-(((1H-benzo[d][1,2,3]triazol-1-yl)oxy)carbonyl)-N-(1,3-dioxoisoindolin-2-yl)glycine (Phth-aza-aspartic acid-carbamoyl-O-benzotriazole), 1H-benzo[d][1,2,3]triazol-1-yl benzyl(1,3-dioxoisoindolin-2-yl)carbamate (Phth-aza-phenylalanine-carbamoyl-O-benzotriazole), 1H-benzo[d][1,2,3]triazol-1-yl (1,3-dioxoisoindolin-2-yl)(methyl)carbamate (Phth-aza-alanine-carbamoyl-O-benzotriazole), 1H-benzo[d][1,2,3]triazol-1-yl ((1H-pyrrol-2-yl)methyl)(1,3-dioxoisoindolin-2-yl)carbamate (Phth-aza-histidine-carbamoyl-O-benzotriazole), 3-((((1H-benzo[d][1,2,3]triazol-1-yl)oxy)carbonyl)(1,3-dioxoisoindolin-2-yl)amino)propanoic acid (Phth-aza-glutamic acid-carbamoyl-O-benzotriazole), 1H-benzo[d][1,2,3]triazol-1-yl ((1H-indol-3-yl)methyl)(1,3-dioxoisoindolin-2-yl)carbamate (Phth-aza-tryptophan-carbamoyl-O-benzotriazole), 1H-benzo[d][1,2,3]triazol-1-yl (1,3-dioxoisoindolin-2-yl)(isopropyl)carbamate (Phth-aza-valine-carbamoyl-O-benzotriazole), 1H-benzo[d][1,2,3]triazol-1-yl (1,3-dioxoisoindolin-2-yl)(isobutyl)carbamate (Phth-aza-leucine-carbamoyl-O-benzotriazole), 1H-benzo[d][1,2,3]triazol-1-yl (4-aminobutyl)(1,3-dioxoisoindolin-2-yl)carbamate (Phth-aza-lysine-carbamoyl-O-benzotriazole), 1H-benzo[d][1,2,3]triazol-1-yl (1,3-dioxoisoindolin-2-yl)(2-(methylthio)ethyl)carbamate (Phth-aza-cysteine-carbamoyl-O-benzotriazole), 1H-benzo[d][1,2,3]triazol-1-yl (1,3-dioxoisoindolin-2-yl)(4-hydroxybenzyl)carbamate (Phth-aza-tyrosine-carbamoyl-O-benzotriazole), 1H-benzo[d][1,2,3]triazol-1-yl sec-butyl(1,3-dioxoisoindolin-2-yl)carbamate (Phth-aza-leucine-carbamoyl-O-benzotriazole), 1H-benzo[d][1,2,3]triazol-1-yl (1,3-dioxoisoindolin-2-yl)(3-guanidinopropyl)carbamate (Phth-aza-arginine-carbamoyl-O-benzotriazole), 1H-benzo[d][1,2,3]triazol-1-yl (1,3-dioxoisoindolin-2-yl)carbamate (Phth-aza-glycine-carbamoyl-O-benzotriazole), 1H-benzo[d][1,2,3]triazol-1-yl (2-amino-2-oxoethyl)(1,3-dioxoisoindolin-2-yl)carbamate (Phth-aza-asparagine-carbamoyl-O-benzotriazole), 1H-benzo[d][1,2,3]triazol-1-yl (3-amino-3-oxopropyl)(1,3-dioxoisoindolin-2-yl)carbamate (Phth-aza-glytamine-carbamoyl-O-benzotriazole), and pharmaceutically acceptable salts thereof.

Compounds of Formula (IV)

Compounds of Formula (IV) are stable at 37° C. in an aqueous medium (e.g., an aqueous solution) with a pH of about 7 (e.g., distilled water) for at least 30 minutes, 60 minutes, 90 minutes, 1 hour, 2 hours, 3 hours, 4 hours or 5 hours.

Compound of Formula (IV) may be used as building blocks or synthons for synthesis of azapeptides and other peptidomimetics. The resulting azapeptides and peptidomimetics may have utility in drug discovery, diagnosis, prevention, inhibition, and treatment of diseases.

In certain embodiments, compounds of Formula (IV) are selected from the group consisting of:

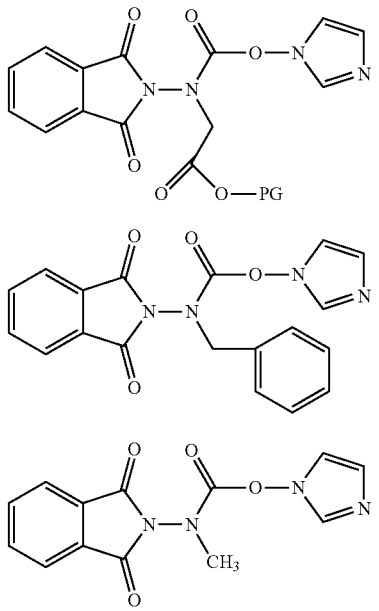

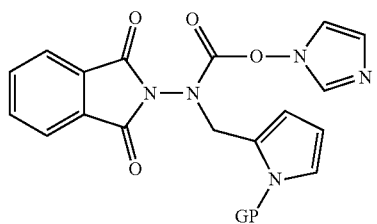
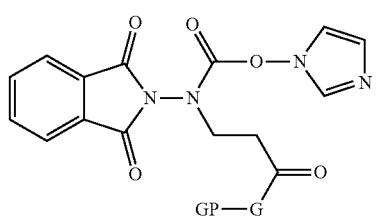
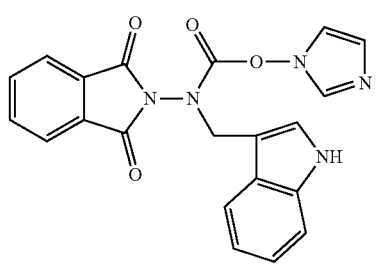 [SMILES: O=C(On1ccnc1)N(Cc1c[nH]c2ccccc12)N1C(=O)c2ccccc2C1=O]
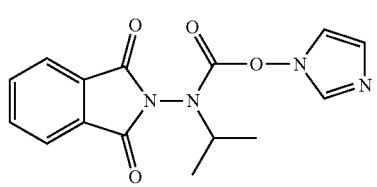 [SMILES: CC(C)N(C(=O)On1ccnc1)N1C(=O)c2ccccc2C1=O]
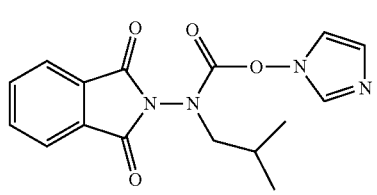 [SMILES: CC(C)CN(C(=O)On1ccnc1)N1C(=O)c2ccccc2C1=O]
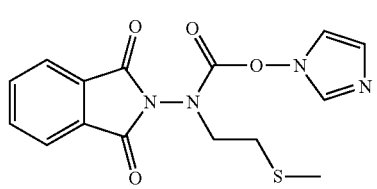 [SMILES: CSCCN(C(=O)On1ccnc1)N1C(=O)c2ccccc2C1=O]
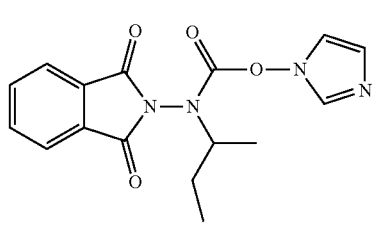 [SMILES: CCC(C)N(C(=O)On1ccnc1)N1C(=O)c2ccccc2C1=O]

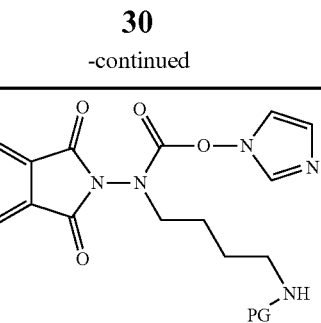
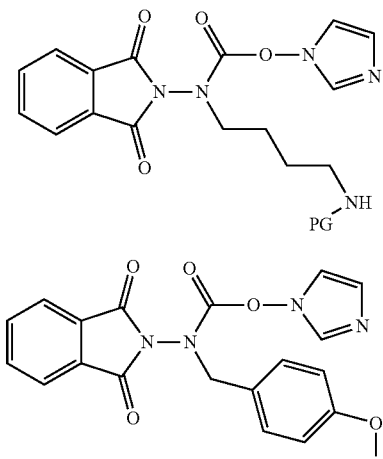
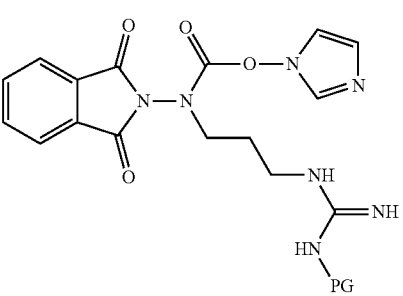
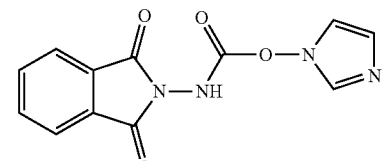
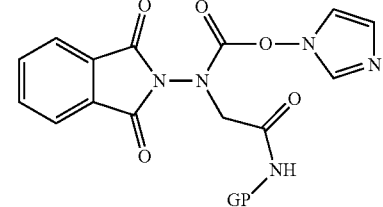
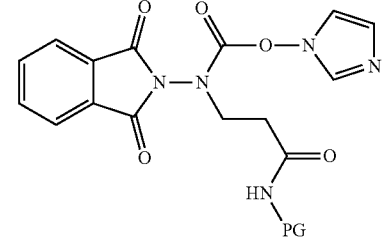

and pharmaceutically acceptable salts thereof, wherein "PG" is H or a protecting group (e.g., Phth, Boc, Fmoc, Ddz, etc.).

In certain embodiments, compounds of Formula (IV) are selected from the group consisting of N-(((1H-imidazol-1-yl)oxy)carbonyl)-N-(1,3-dioxoisoindolin-2-yl)glycine (Phth-aza-aspartic acid-carbamoyl-O-imidazole), 1H-imidazol-1-ylbenzyl(1,3-dioxoisoindolin-2-yl)carbamate (Phth-aza-phenylalanine-carbamoyl-O-imidazole), 1H-imidazol- 1-yl (1,3-dioxoisoindolin-2-yl)(methyl)carbamate (Phth-aza-alanine-carbamoyl-O-imidazole), 1H-imidazol-1-yl ((1H-pyrrol-2-yl)methyl)(1,3-dioxoisoindolin-2-yl)carbamate (Phth-aza-histidine-carbamoyl-O-imidazole), 3-((((1H-imidazol-1-yl)oxy)carbonyl)(1,3-dioxoisoindolin-2-yl)amino)propanoic acid (Phth-aza-glutamic acid-carbamoyl-O-imidazole), 1H-imidazol-1-yl ((1H-indol-3-yl)methyl)(1,3-dioxoisoindolin-2-yl)carbamate (Phth-aza-tryptophan-carbamoyl-O-imidazole), 1H-imidazol-1-yl (1,3-dioxoisoindolin-2-yl)(isopropyl)carbamate (Phth-aza-valine-carbamoyl-O-imidazole), 1H-imidazol-1-yl (1,3-dioxoisoindolin-2-yl)(isobutyl)carbamate (Phth-aza-leucine-carbamoyl-O-imidazole), 1H-imidazol-1-yl (4-aminobutyl)(1,3-dioxoisoindolin-2-yl)carbamate (Phth-aza-lysine-carbamoyl-O-imidazole), 1H-imidazol-1-yl (1,3-dioxoisoindolin-2-yl)(2-(methylthio)ethyl)carbamate (Phth-aza-cysteine-carbamoyl-O-imidazole), 1H-imidazol-1-yl (1,3-dioxoisoindolin-2-yl)(4-hydroxybenzyl)carbamate (Phth-aza-tyrosine-carbamoyl-O-imidazole), 1H-imidazol-1-yl sec-butyl(1,3-dioxoisoindolin-2-yl)carbamate (Phth-aza-iso-leucine-carbamoyl-O-imidazole), 1H-imidazol-1-yl (1,3-dioxoisoindolin-2-yl)(3-guanidinopropyl)carbamate (Phth-aza-arginine-carbamoyl-O-imidazole), 1H-imidazol-1-yl (1,3-dioxoisoindolin-2-yl)carbamate (Phth-aza-glycine-carbamoyl-O-imidazole), 1H-imidazol-1-yl (2-amino-2-oxoethyl)(1,3-dioxoisoindolin-2-yl)carbamate (Phth-aza-asparagine-carbamoyl-O-imidazole), 1H-imidazol-1-yl (3-amino-3-oxopropyl)(1,3-dioxoisoindolin-2-yl)carbamate (Phth-aza-glutamine-carbamoyl-O-imidazole), and pharmaceutically acceptable salts thereof.

Synthesis of Azapeptides and Azatides

Compounds of Formula (IA), (IB), (II), (III), and (IV) can be coupled in a linear, stepwise, chain-lengthening fashion to each other, amino acids, aza-amino acids, peptides, azapeptides, and azatides by solution or liquid phase, solid-phase and mixed solution/solid phase synthetic methodologies to construct compounds of Formulas (V).

Compounds of Formula (IA), (IB), (II), (III), and (IV) can also be used, e.g., as sub-monomers to elongate and/or cap peptides and azapeptides.

For example, in certain embodiments, compounds of Formula (IA), (IB), (II), and (IV) may be activated by iodomethane, and the activated compound may be coupled, e.g., a protected or unprotected aza-amino acid; a protected or unprotected peptide; a protected or unprotected azapeptide; a protected or unprotected azatide; or a protected or unprotected compound of Formula (IA), Formula (IB) Formula (II), Formula (III), or Formula (IV); or a protected or unprotected hydrazine, by either solution or liquid phase synthetic methodologies, e.g., to form a compound of Formula (V). The amino acid, the aza-amino acid, the peptide, the azapeptide, compound of Formula (IA), (IB), (II), (III), and (IV) may each be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). The coupling may, e.g., be for up to about 20 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes.

The methods of the invention may be used to synthesize azapeptides and azatides from 2 to 200 mers in length, e.g., di-azatides, tri-azatides, tetra-azapeptides, penta-azapeptides, etc. In certain embodiments, the peptide is 9 mers in length.

In certain embodiments, the method of preparing an azapeptide or an azatide comprises hydrolysing a peptide, e.g., a compound of Formula (VI) into fragments and reacting one or more fragments with a compound of Formula (IA), (IB), (II), (III), or (VI).

In certain embodiments, the method of preparing an azapeptide or an azatide comprises cleaving a peptide, e.g., a compound of Formula (VI), into fragments and reacting one or more fragments with a compound of Formula (IA), (IB), (II), (III), or (VI).

In certain embodiments, the method of preparing an azapeptide or an azatide comprises cleaving an end of a peptide, e.g., a compound of Formula (VI), and reacting the cleaved peptide with a compound of Formula (IA), (IB), (II), (III), or (VI).

In certain embodiments, the method of preparing an azapeptide or an azatide comprises reacting a compound of Formula (IA), (IB), (II), (III), or (VI) with a truncated peptide.

In certain embodiments, the method of preparing an azapeptide or an azatide comprises conjugating a compound of Formula (IA), (IB), (II), (III), or (VI) with a truncated peptide, e.g., a compound of Formula (VI).

In certain embodiments, a method of azapeptide or azatide synthesis comprises reacting (i) a benzotriazole derivative of an aza-amino acid comprising an aza-amino acid covalently bound (conjugated) to a protecting group at its N-terminus and to benzotriazole at its C-terminus with (ii) a peptide to form the azapeptide or azatide, wherein the benzotriazole derivative of the aza-amino acid azapeptide or azatide is a compound of Formula (IA), (IB), (II) or (III).

In certain embodiments, a method of azapeptide or azatide synthesis comprises reacting (i) an imidazole derivative of an aza-amino acid comprising an aza-amino acid covalently bound (conjugated) to a protecting group at its N-terminus and to imidazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a hydrazide to form an azapeptide. In certain embodiments, the imidazole derivatve is a compound of Formula (IV).

Uses of Compounds of Formula (V)

Compounds of Formula (V) are azapeptide analogues of compounds of Formula (VI). In the preferred embodiments, compounds of Formula (V) are more resistant to hydrolysis and/or enzymatic degradation than compounds of Formula (VI).

Compounds of Formula (V) may be used to inhibit peptidases, both in vitro and in vivo. The peptidase may, e.g., be an endopeptidase, an exopeptidase, an aspartic protease, a glutamic protease, an asparagine peptide lyase, or a retroviral protease.

In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention, inhibition, and treatment of diseases.

Compounds of Formulas (V) may each comprise from 2 to 200 carbonyl group(s). For example, compounds of Formula (V) may each comprise 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 36, 37, 38, 39, 40, 41, 43, 44, 56, or 166 carbonyl groups. In certain embodiments, compounds of Formula (V) comprise from 2 to 60 carbonyl groups, from 2 to 50 carbonyl groups, from 2 to 40 carbonyl groups, from 2 to 30 carbonyl groups, from 2 to 25 carbonyl groups, from 2 to 20 carbonyl groups, from 2 to 15 carbonyl groups, from 2 to 12 carbonyl groups, from 2 to 10 carbonyl groups, from 2 to 9 carbonyl groups, from 3 to 40 carbonyl groups, from 3 to 30 carbonyl groups, from 3 to 25 carbonyl groups, from 3 to 20 carbonyl groups, from 3 to 15 carbonyl groups, from 3 to 12 carbonyl groups, from 3 to 10 carbonyl groups, or from 3 to 9 carbonyl groups.

In certain embodiments, compounds of Formula (V) comprise from 2 to 200 carbonyl groups and at least one α-nitrogen covalently bound to at least one of said carbonyl groups, and have a greater bioavailability (e.g., oral, transdermal, and/or intranasal) than a peptide structurally different from the compounds of Formula (V) only in that that the peptide comprises α-carbon instead of said α-nitrogen. In certain embodiments, the α-nitrogen is at the N-termini or C-termini of the compounds of Formula (V). In certain embodiments, the α-nitrogen is at the N-termini and the C-termini of the compounds of Formula (V). In certain embodiments, the α-nitrogen is not at the N-termini and not at the C-termini of the compounds of Formula (V), rather it is at a cleavage or hydrolysis site(s) of the peptide.

In certain embodiments, compounds of Formula (V) are azapeptide analogues of therapeutic peptides.

In certain embodiments, compounds of Formula (V) are azapeptide analogues of diagnostic peptides.

Compounds of Formula (V) may be used in drug discovery, diagnosis, prevention, inhibition, and treatment of diseases.

In certain embodiments, compounds of Formula (V) comprise a backbone comprising from 2 to 200 carbonyl groups and α-nitrogen covalently bound to at least one of said carbonyl groups, and are therapeutically effective for the treatment of a disorder in a subject, while a peptide structurally different from the compounds of Formula (V) only in that the peptide comprises α-carbon instead of said α-nitrogen is not therapeutically effective for the treatment of the disorder. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 2 to 200 carbonyl groups and α-nitrogen covalently bound to at least one of said carbonyl groups, and have a therapeutic efficacy greater than a peptide structurally different from the compounds of Formula (V) only in that the peptide comprises an α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 2 to 200 carbonyl groups and α-nitrogen covalently bound to at least one of said carbonyl groups, and have a longer duration of therapeutic activity than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 2 to 75 carbonyl groups and at least one α-nitrogen covalently bound to at least one of said carbonyl groups, and have an in vivo half-life greater than a peptide structurally different from the compounds of Formula (V) only in that said at least one α-nitrogen is replaced with α-carbon. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise a backbone comprising from 2 to 75 carbonyl groups, wherein at least two carbonyl groups are covalently bound to a trivalent nitrogen, and compounds of Formula (V) have an in vivo half-life greater than a peptide structurally different from the compounds of Formula (V) only in that one or more alpha nitrogen(s) of the compounds of Formula (V) is replaced with alpha carbon(s). The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise at least one aza-amino acid, and have an in vivo half-life greater than a peptide structurally different from the compounds of Formula (V) only in that the aza-amino acid(s) is replaced with a corresponding amino acid. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 2 to 200 carbonyl groups and α-nitrogen covalently bound to at least one of said carbonyl groups, and are more resistant to protease degradation than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 2 to 200 carbonyl groups and α-nitrogen covalently bound to at least one of said carbonyl groups, and have a greater affinity to a biological receptor than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprises from 2 to 60 carbonyl groups.

In certain embodiments, compounds of Formula (V) are linear.

In certain embodiments, compounds of Formula (V) are cyclic.

In certain embodiments, compounds of Formula (V) are pegylated.

In certain embodiments, compounds of Formula (V) are conjugated to an immunoglobulin.

In certain embodiments, compounds of Formula (V) comprise α-nitrogen at the N-terminus of its backbone.

In certain embodiments, compounds of Formula (V) comprise α-nitrogen at the C-terminus of its backbone In certain embodiments, compounds of Formula (V) comprise two carbonyl groups and two α-nitrogens.

In certain embodiments, compounds of Formula (V) comprise three carbonyl groups and one α-nitrogen.

In certain embodiments, compounds of Formula (V) comprise three carbonyl groups and two α-nitrogens.

In certain embodiments, compounds of Formula (V) comprise three carbonyl groups and three α-nitrogens.

In certain embodiments, compounds of Formula (V) comprise four carbonyl groups and one α-nitrogen.

In certain embodiments, compounds of Formula (V) comprise four carbonyl groups and two α-nitrogens.

In certain embodiments, compounds of Formula (V) comprise four carbonyl groups and three α-nitrogens.

In certain embodiments, compounds of Formula (V) comprise four carbonyl groups and four α-nitrogens.

In certain embodiments, compounds of Formula (V) are azapeptide analogues of a 2 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 2 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine, wherein the analogue includes at least one corresponding aza-amino acid of the amino acid.

In certain embodiments, compounds of Formula (V) are azapeptide analogues of a 2 to 200 amino acid peptide, the 2 to 200 amino acid peptide comprising amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, the analogue differing from the amino acid peptide in that that the aza-analogues comprise an aza-amino acid instead of at least one of the amino acids, wherein the aza-analogues comprise aza-glycine instead of glycine, and/or the aza-analogues comprise aza-alanine instead of alanine, and/or the aza-analogues comprise aza-valine instead of valine, and/or the aza-analogues comprise aza-leucine instead of leucine, or/and the aza-analogues comprise aza-isoleucine instead of iso-leucine, and/or the aza-analogues comprise aza-proline instead of proline, and/or the aza-analogues comprise aza-phenylalanine instead of phenylalanine, or/and the aza-analogues comprise comprises aza-tyrosine instead of tyrosine, and/or the aza-analogues comprise aza-tryptophan instead of tryptophan, or/and the aza-analogues comprise aza-aspartic acid instead of aspartic acid, and/or the aza-analogues comprise aza-glutamic acid instead of glutamic acid, and/or the aza-analogues comprise aza-aspargine instead of aspargine, and/or the aza-analogues comprise aza-glutamine instead of glutamine, and/or the aza-analogues comprise aza-histidine instead of histadine, and/or the aza-analogues comprise aza-lysine instead of lysine, and/or the aza-analogues comprise aza-arginine instead of arginine.

In certain embodiments, compounds of Formula (V) are azapeptide analogues of a peptide comprising from 2 to 50 amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, and at least 2, 3, 4, 5, 6, 7, 8, 9 or 10 of the amino acids are replaced with corresponding aza-amino acids. In some of these embodiments, the replaced amino acid is the first amino acid of the peptide. In some of these embodiments, the replaced amino acid is the last amino acid of the peptide. In some of these embodiments, the first and the last amino acids of the peptide are both replaced with corresponding aza-amino acids.

In certain embodiments, compounds of Formula (V) are azapeptide analogues of a 10-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 9-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 8-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 7-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 6-mer peptide comprising an amino acid selected from the group consisting of glycine, alanine, valine, leucine, isoleucine, proline, phenylalanine, tyrosine, tryptophan, aspartic acid, glutamic acid, asparagine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 5-mer peptide comprising an amino acid selected from the group consisting of glycine, alanine, valine, leucine, isoleucine, proline, phenylalanine, tyrosine, tryptophan, aspartic acid, glutamic acid, asparagine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 5-mer peptide comprising an amino acid selected from the group consisting of glycine, alanine, valine, leucine, isoleucine, proline, phenylalanine, tyrosine, tryptophan, aspartic acid, glutamic acid, asparagine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 4-mer peptide comprising an amino acid selected from the group consisting of glycine, alanine, valine, leucine, isoleucine, proline, phenylalanine, tyrosine, tryptophan, aspartic acid, glutamic acid, asparagine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 3-mer peptide comprising an amino acid selected from the group consisting of glycine, alanine, valine, leucine, isoleucine, proline, phenylalanine, tyrosine, tryptophan, aspartic acid, glutamic acid, asparagine, glutamine, histidine, lysine, and arginine; the aza-analogues differing from the amino acid peptide in that that the amino acid of the peptide is replaced with a corresponding aza-amino acid.

In certain embodiments, the last amino acid of the peptide is selected from the group consisting of aspartic acid, phenylalanine, and arginine.

In certain embodiment, the first amino acid of the peptide is selected from the group consisting of tyrosine, phenylalanine, and arginine.

In certain embodiments, the first and the last amino acid of the peptide are the same.

In certain embodiments, the first and the last amino acids of the peptide are different.

In certain embodiments, compounds of Formula (V) are not azatides.

In certain embodiments, compounds of Formula (V) comprise an amino acid selected from the group consisting of cysteine, methionine, serine and threonine.

In certain embodiments, compounds of Formula (V) comprise at least one, at least two or at least three aza-glycine(s).

In certain embodiments, compounds of Formula (V) comprise at least one, at least two or at least three aza-alanine(s).

In certain embodiments, compounds of Formula (V) comprise at least one, at least two or at least three aza-valine(s).

In certain embodiments, compounds of Formula (V) comprise at least one, at least two or at least three aza-leucine(s).

In certain embodiments, compounds of Formula (V) comprise at least one, at least two or at least three aza-isoleucine(s).

In certain embodiments, compounds of Formula (V) comprise at least one, at least two or at least three aza-proline(s).

In certain embodiments, compounds of Formula (V) comprise at least one, at least two or at least three aza-phenylalanine(s).

In certain embodiments, compounds of Formula (V) comprise at least one, at least two or at least three aza-tyrosine(s).

In certain embodiments, compounds of Formula (V) comprise at least one, at least two or at least three aza-tryptophan(s).

In certain embodiments, compounds of Formula (V) comprise at least one, at least two or at least three aza-aspartic acid(s).

In certain embodiments, compounds of Formula (V) comprise at least one, at least two or at least three aza-glutamic acid(s).

In certain embodiments, compounds of Formula (V) comprise at least one, at least two or at least three aza-aspargine(s).

In certain embodiments, compounds of Formula (V) comprise at least one, at least two or at least three aza-glutamine(s).

In certain embodiments, compounds of Formula (V) comprise at least one, at least two or at least three aza-histidine(s).

In certain embodiments, compounds of Formula (V) comprise at least one, at least two or at least three aza-lysine(s).

In certain embodiments, compounds of Formula (V) comprise at least one, at least two or at least three aza-arginine(s).

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, and have a greater bioavailability (e.g., oral, transdermal, and/or intranasal) than the therapeutic peptide (in its unaltered state).

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, maintain the therapeutic efficacy of the therapeutic peptide and have an in vivo half-life greater than the in vivo half-life of the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a longer duration of therapeutic activity than the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and are more resistant to protease degradation than the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a greater affinity to a biological receptor than the therapeutic peptide.

Di-azatides

In certain embodiments, a compound of Formula (V) is a di-azatide of a compound of Formula (IX)

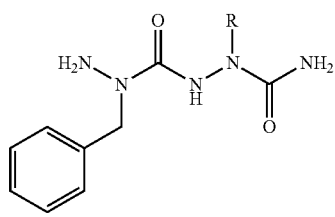

(IX)

or a pharmaceutically acceptable salt thereof, wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine.

The di-azatides may, e.g., be prepared by a solution phase or a solid phase synthesis. In certain embodiments, the yield (in % by weight) is from about 80% to about 98%.

The di-azatides may be prepared both with C-to-N terminal construction and N-to-C terminal construction.

Tri-azatide

In certain embodiments, a compound of Formula (V) or is a tri-azatide of Formula (X):

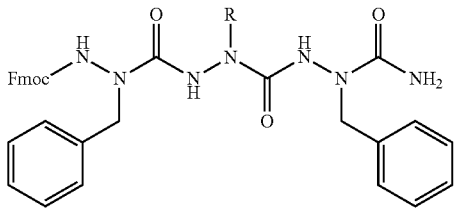

(X)

or a pharmaceutically acceptable salt thereof, wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, proline, and glutamine.

The tri-azatides may, e.g., be prepared by a solution phase or a solid phase synthesis.

The tri-azatides may be prepared both with C-to-N terminal construction and N-to-C terminal construction.

Tetra-Azapeptides

In certain embodiments, a compound of Formula (V) is a compound of formula:

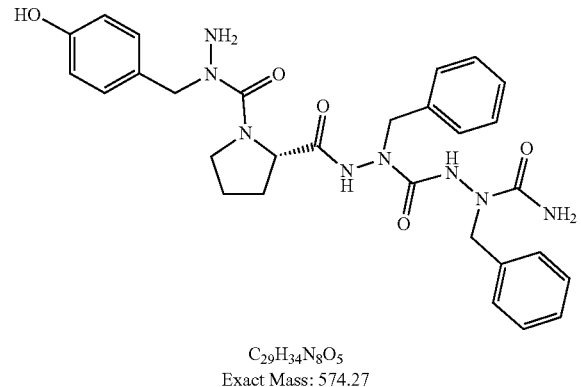

K763

$C_{29}H_{34}N_8O_5$
Exact Mass: 574.27 or a pharmaceutically acceptable salt thereof.

In certain embodiments, a compound of Formula (V) is a compound of formula:

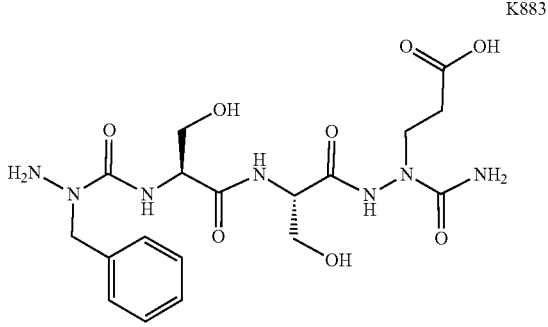

K883

$C_{18}H_{27}N_7O_8$
Exact Mass: 469.19 or a pharmaceutically acceptable salt thereof.

The tetra-azatides may, e.g., be prepared by a solution phase or a solid phase synthesis.

The tetra-azatides may be prepared both with C-to-N terminal construction and N-to-C terminal construction.

Nine-mer Azapeptides

In certain embodiments, a compound of Formula (V) is a compound of formula:

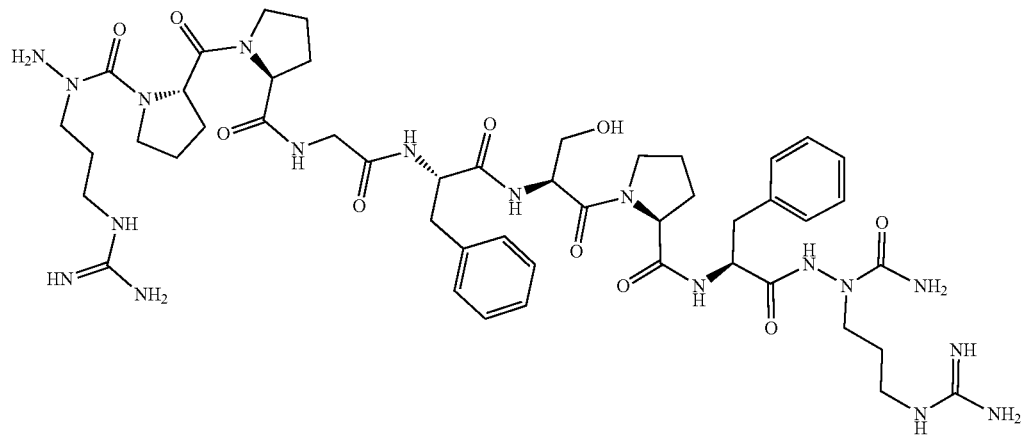 [SMILES: N=C(N)NCCCN(N)C(=O)N1CCC[C@H]1C(=O)N1CCC[C@H]1C(=O)NCC(=O)N[C@@H](Cc1ccccc1)C(=O)N[C@@H](CO)C(=O)N1CCC[C@H]1C(=O)N[C@@H](Cc1ccccc1)C(=O)NN(CCCNC(=N)N)C(N)=O]

or a pharmaceutically acceptable salt thereof.

In certain embodiments, a compound of Formula (V) is a compound of formula:

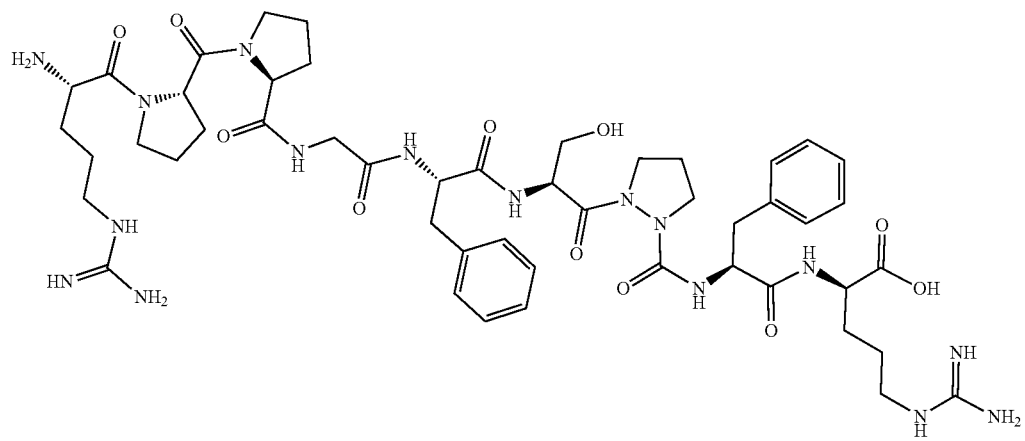 [SMILES: N=C(N)NCCC[C@H](N)C(=O)N1CCC[C@H]1C(=O)N1CCC[C@H]1C(=O)NCC(=O)N[C@@H](Cc1ccccc1)C(=O)N[C@@H](CO)C(=O)N1CCCN1C(=O)N[C@@H](Cc1ccccc1)C(=O)N[C@H](CCCNC(=N)N)C(=O)O]

or a pharmaceutically acceptable salt thereof.

In certain embodiments, a compound of Formula (V) is a compound of formula:
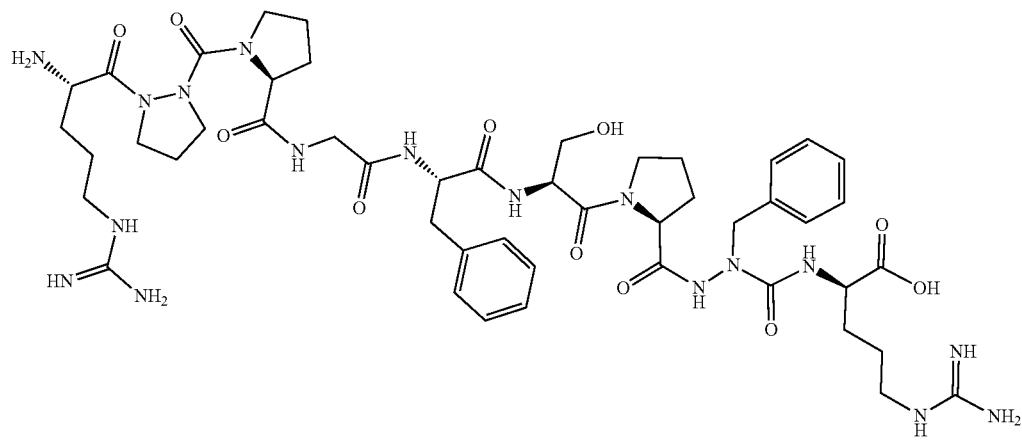 [SMILES: N=C(N)NCCC[C@H](N)C(=O)N1CCCN1C(=O)N1CCC[C@H]1C(=O)NCC(=O)N[C@@H](Cc1ccccc1)C(=O)N[C@@H](CO)C(=O)N1CCC[C@H]1C(=O)NN(Cc1ccccc1)C(=O)N[C@H](CCCNC(=N)N)C(=O)O]
or a pharmaceutically acceptable salt thereof.
In certain embodiments, a compound of Formula (V) is a compound of formula:
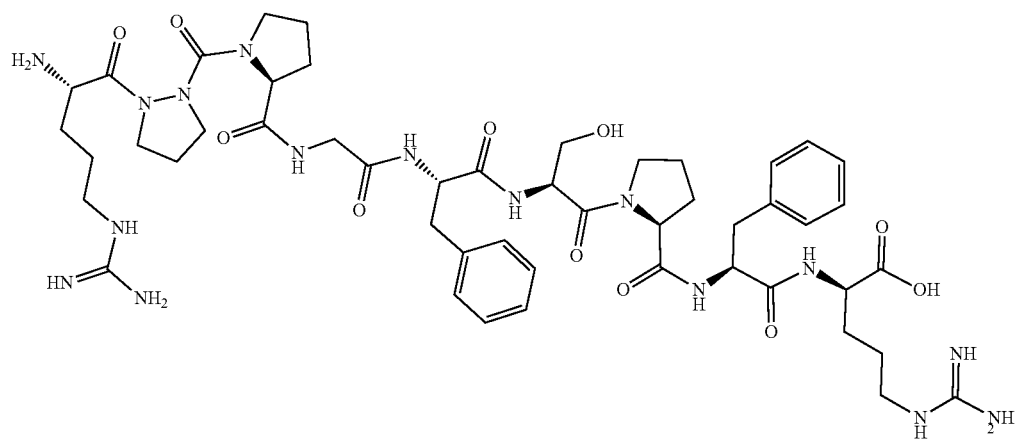 [SMILES: N=C(N)NCCC[C@H](N)C(=O)N1CCCN1C(=O)N1CCC[C@H]1C(=O)NCC(=O)N[C@@H](Cc1ccccc1)C(=O)N[C@@H](CO)C(=O)N1CCC[C@H]1C(=O)N[C@@H](Cc1ccccc1)C(=O)N[C@H](CCCNC(=N)N)C(=O)O]
or a pharmaceutically acceptable salt thereof.
In certain embodiments, a compound of Formula (V) is a compound of formula:
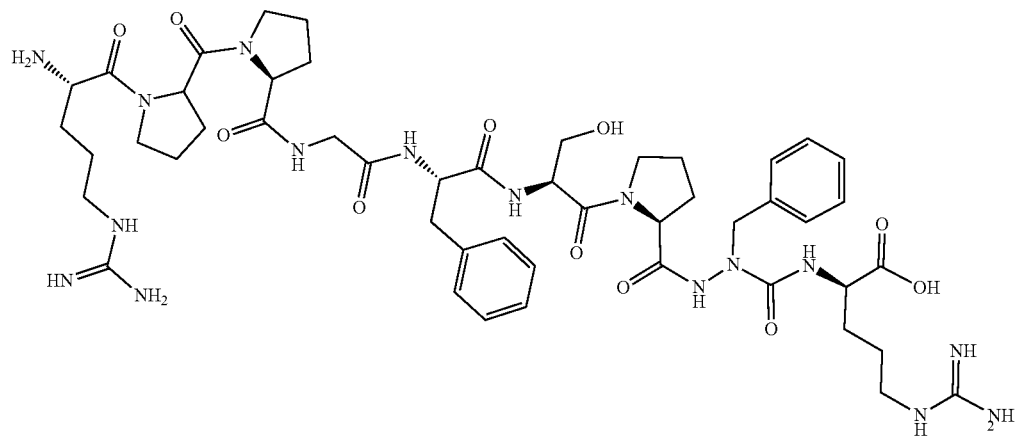 [SMILES: N=C(N)NCCC[C@H](N)C(=O)N1CCCC1C(=O)N1CCC[C@H]1C(=O)NCC(=O)N[C@@H](Cc1ccccc1)C(=O)N[C@@H](CO)C(=O)N1CCC[C@H]1C(=O)NN(Cc1ccccc1)C(=O)N[C@H](CCCNC(=N)N)C(=O)O]
or a pharmaceutically acceptable salt thereof.

The nine-mer azapeptides may, e.g., be prepared by a solution phase, a solid phase synthesis and a combination of the solution and solid phase synthesis.

The nine-mer azapeptides may be prepared both with C-to-N terminal construction and N-to-C terminal construction.

Additional Azapeptides

In certain embodiments, compounds of Formula (V) are selected from the group consisting of aza-analogues of A-6, A-623 (AMG-623), A-71378, A-75998, Abarelix (PPI-149), ABT-510, AC-100, AC-162352 (PYY 3-36), AC-253, AC-2592, AC-625, ACV-1, ADH-1, AEZS-108 (AN-152) (ZEN-008), AF-37702, Afamelanotide (EP-1647) (CUV-1647) (Melanotan I), AG2/102, AG-284, AI-502, AKL-0707 (LAB GHRH), Albiglutide (GSK-716155), Albuvirtide, ALG-889, Alloferon, Allotrap 2702 (B-2702), ALTY-0601, ALX-40-4C, Ambamustine (PTT-119), Anaritide, Antagonist G (PTL-68001), AOD-9604, APL-180, ATN-161, Atosiban (ORF-22164), Atriopeptin, Aviptadil (PSD-510), Avorelin (EP-23904), AZD-2315, Azetirelin (YM-14673), AZX-100, B27PD, BA-058, Barusiban (FE-200400), BAY-73-7977, BDM-E, BGC-728, BIM-23190, BIM-44002, BIO-1211, Bivalirudin (BG-8865), BMS-686117, Bremelanotide (PT-141), BRX-0585, Buserelin, Calcitonin (Human), Calcitonin (Salmon), Carbetocin, Carfilzomib (PR-171), Cargutocin (Y-5350), Carperitide (SUN-4936), Casokefamide, CB-182804, CB-183315, CBP-501, CBT-101, CCK (25-33), CD-NP, Cemadotin (LU-103793), Cetrorelix (NS-75), CG-77X56, CGRP (LAB-CGRP), Chlorotoxin (TM-601), Cilengitide (EMD-121974) (EMD-85189), CJC-1008 (DAC: Dynorphin A), CJC-1131 (DAC: GLP-1), CJC-1134 (PC-DAC) (Exendin-4), CJC-1295 (DAC:GRF), Cnsnqic-Cyclic (802-2), Compstatin (POT-4), Conantokin G, Contulakin G (CGX-1007), Corticorelin (NEU-3002), CP-95253, C-peptide (SPM-933), CR-665, CR-845, CTCE-0214, CTCE-9908, CTS-21166 (ASP-1702) (ATG-Z1) (OM-00-3) (OM-99-2), CVX-045, CVX-060, CVX-096 (PF-4856883), CZEN-002, D-4F (APP-018), Danegaptide (ZP-1609) (WAY-261134) (GAP-134), Davalintide (AC-2307), Davunetide (AL-108) (AL-208), Degarelix (FE 200486), Delmitide (RDP-58), Deltibant (CP-0127), Deslorelin, Desmopressin, Detirelix (RS-68439), DG-3173 (PTR-3173), Didemnin B (NSC-325319), Dirucotide (MBP-8298) Disitertide (NAFB-001) (P-144), DMP-728 (DU-728), dnaJP1 (AT-001), Dopastatin (BIM-23A760), DPK-060, DRF-7295, DSC-127, Dynorphin A, E-2078, EA-230, Ebiratide (Hoe-427), Edotreotide (SMT-487), Edratide (TV-4710), Efegatran (LY-294468), Elcatonin, Eledoisin (ELD-950), Elisidepsin (PM-02734), EMD-73495, Enfuvirtide (T-20), EP-100, EP-51216 (EP-51389), Eptifibatide (C68-22), ET-642 (RLT-peptide), ETRX 101, Examorelin (EP-23905) (W-6003), Exenatide (AC-2993) (LY-2148568), Exsulin (INGAP Peptide), F-991, FAR-404, FE 202158, Felypressin, FGLL, Frakefamide (LEF-576) (SPD-759) (BCH-3963), FX-06, Ganirelix (Org-37462) (RS-26306), Glaspimod (SKF-107647), Glatiramer (COP-1), Glucagon, Glucosamyl muramyl tripeptide, Glutoxim (NOV-002), Glypromate, GMDP, Golotimod (SCV-07), Goralatide (BIM-32001), Goserelin (ICI-118630), GPG-NH2, GTP-200, GTP-300, H-142, Hemoparatide (PTH 1-37), Hexapeptide copper II (PC-1358), Histrelin, hLF (1-11), HP-228, I-040302 (KUR-112), Icatibant (JE-049) (HOE-140), Icrocaptide (ITF-1697), IMX-942, 1pamorelin (NNC-26-0161), IPP-201101, Iseganan (IB-367), ISF402, Iturelix (ORF-23541), JTP-2942, KAI-1455, KAI-1678, KM-9803, KP-101 (GHRP-1), L-346670, L-364343, Labradimil (RMP-7), Lagatide (BN-52080), Lanreotide (ITM-014), Larazotide (AT-1001) (SPD-550), Leconotide (AM-336), Leuprolide (SOT-375), Linaclotide (MD-1100) (MM-41775), Liraglutide (NN-2211), Lixisenatide (AVE-0010) (ZP-10), LSI-518P, Lucinactant, Lusupultide (BY-2001), LY-2189265, LY-2510924, LY-548806, LYN-001, Lypressin, MER-104, Met-enkephalin (INNO-105), Metkephamide (LY-127623), Mifamurtide (CGP-19835) (MLV-19835), Montirelin (CG-3703), MPL-TLB100, MS peptide, MT-11 (PT-14), Murabutide (VA-101) (CY-220), Muramyl tripeptide, Nafarelin (RS-94991), NBI-6024, Nemifitide (INN-00835), Neogen, Nepadutant (MEN-11420), Nesiritide, Nifalatide (BW942C), NNZ-2566, NP-213, NFC-567, NPY (24-36) (PTL-041120), NT-13, Obinepitide (TM-30338), Octreotide (SMS-201-995), Oglufanide (IM-862), OGP 10-14L, Omiganan (CPI-226), OP-145, ORG-2766 Org-42982 (AG-4263), Ornithine vasopressin, Oxytocin, Ozarelix (D-63153) (SPI-153), p-1025, P-113 (PAC-113), Pasireotide (SOM-230), peg-TPOmp (RWJ-800088), Pentigetide (TA-521), Pep-F (5K), Peptide renin inhibitor, Peptide T (AIDS000530), Peptide YY 3-36, Pexiganan (MSI-78), PF-4603629, PI-0824, PI-2301, PL-3994, PLD-116, PMX-53, POL-6326, Posatirelin, PPI-1019, Pralmorelin, Pramlintide, Protirelin, PTH (7-34), PTHrP-(1-36), PTL-0901, PXL-01, R-1516, R-15-K, R-7089, RA peptide, Ramorelix (Hoe-013), RC-3095, Re-188-P-2045 (P2045), rGRF, Romiplostim (AMG-531), Romurtide (DJ-7041), ROSE-010 (GTP-010) (LY-307161), Rotigaptide (ZP-123) (GAP-486), Rusalatide (TP-508), SAN-134, Saralasin (P-113), Secretin (human) (PGN-52) (R-52), Secretin (human) (RG-1068), Semaglutide (NN-9535), SGS-111, Sifuvirtide, SKF-101926, SKF-105494, SKF-110679 (U-75799E), Soblidotin (YHI-501) (TZT-1027), Somatostatin, Somatostatin (D-Trp, D-Cys analog), SP-304 (Guanilib), SPC-3, SPI-1620, SST analog, SUN-11031, SUN-E7001 (CS-872), SYN-1002, Tabilautide (RP-56142), TAK-448, TAK-683, Taltirelin (TA-0910), Tasidotin (ILX-651) (BSF-223651), Taspoglutide (BIM-51077), TCMP-80, Teduglutide (ALX-0600), Teriparatide (LY-333334), Terlakiren (CP-80794), Terlipressin, Tesamorelin (TH-9507), Teverelix (EP-24332), TH-0318, TH-9506, Thymalfasin, Thymodepressin, Thymonoctan (FCE-25388), Thymopentin (TP-5), Thymosin beta-4, Tifuvirtide (R-724) (T-1249), Tigapotide (PCK-3145), Tiplimotide (NBI-5788), TKS-1225 (Oxyntomodulin), TLN-232 (CAP-232)(TT-232), TM-30339, TP-9201, TRI-1144, Tridecactide (AP-214), Triletide (Z-420) (ZAMI-420), Triptorelin (WY-42462), TT-223 (E1-INT), TT-235, TX14(A), Tyroserleutide (CMS-024), Tyroservatide (CMS-024-02), Ularitide (CDD-95-126) (ESP-305), Unacylated ghrelin (AZP-01) (TH-0332), Urocortin 11, Vapreotide (RC-160), Vasopressin, VIR-576, Xen-2174, XG-102, XOMA-629, Ziconotide (SNX-111), ZP-120, or ZP-1846.

In certain embodiments, compounds of Formula (V) are selected from the group consisting of aza-analogues of AC-2592, AC-625, Anaritide, APL-180, Atriopeptin, BGC-728, Carperitide (SUN-4936), CD-NP, CG-77X56, D-4F (APP-018), Danegaptide (ZP-1609) (WAY-261134) (GAP-134), DMP-728 (DU-728), Efegatran (LY-294468), EMD-73495, Eptifibatide (C68-22), ET-642 (RLT-peptide), FE 202158, FX-06, Icatibant (JE-049) (HOE-140), Icrocaptide (ITF-1697), KAI-1455, KM-9803, L-346670, L-364343, LSI-518P, Nesiritide, Peptide renin inhibitor, PL-3994, Rotigaptide (ZP-123) (GAP-486), Saralasin (P-113), SKF-105494, Terlakiren (CP-80794), Tridecactide (AP-214), Ularitide (CDD-95-126) (ESP-305), Urocortin 11, Ziconotide (SNX-111), or ZP-120; and have utility in the treatment of cardiovascular diseases (e.g., alleviate one or more symptom(s) of a cardiovascular disease).

In certain embodiments, compounds of Formula (V) are selected from the group consisting of aza-analogues of Azetirelin (YM-14673), Conantokin G, Corticorelin (NEU-3002), CTS-21166 (ASP-1702) (ATG-Z1) (OM-00-3) (OM-99-2), Davunetide (AL-108) (AL-208), Deltibant (CP-0127), Ebiratide (Hoe-427), FGLL, Glypromate, JTP-2942, Montirelin (CG-3703), Nemifitide (INN-00835), NNZ-2566, NT-13, ORG-2766, Peptide T (AIDS000530), Posatirelin, PPI-1019, Protirelin, Secretin (human) (RG-1068), SGS-111, Taltirelin (TA-0910), XG-102, or Ziconotide (SNX-111), and have utility in the treatment of CNS disorders (e.g., alleviate one or more symptom(s) of a CNS disorder).

In certain embodiments, compounds of Formula (V) and are selected from the group consisting of aza-analogues of A-6, Abarelix (PPI-149), ABT-510, ADH-1, AEZS-108 (AN-152) (ZEN-008), Ambamustine (PTT-119), Antagonist G (PTL-68001), ATN-161, Avorelin (EP-23904), Buserelin, Carfilzomib (PR-171), CBP-501, Cemadotin (LU-103793), Chlorotoxin (TM-601), Cilengitide (EMD-121974) (EMD-85189), CTCE-9908, CVX-045, CVX-060, Degarelix (FE 200486), Didemnin B (NSC-325319), DRF-7295, Edotreotide (SMT-487), Elisidepsin (PM-02734), EP-100, Glutoxim (NOV-002), Goralatide (BIM-32001), Goserelin (ICI-118630), Histrelin, Labradimil (RMP-7), Leuprolide (SOT-375), LY-2510924, Met-enkephalin (INNO-105), Mifamurtide (CGP-19835) (MLV-19835), Muramyl tripeptide, Ozarelix (D-63153) (SPI-153), POL-6326, Ramorelix (Hoe-013), RC-3095, Re-188-P-2045 (P2045), Romurtide (DJ-7041), Soblidotin (YHI-501) (TZT-1027), SPI-1620, Tabilautide (RP-56142), TAK-448, TAK-683, Tasidotin (ILX-651) (BSF-223651), Teverelix (EP-24332), Tigapotide (PCK-3145), TLN-232 (CAP-232)(TT-232), Triptorelin (WY-42462), Tyroserleutide (CMS-024), Tyroservatide (CMS-024-02), ZP-1848, in ZT0131; and have utility in the treatment of oncological conditions (e.g., alleviate one or more symptom(s) of an oncological condition).

In certain embodiments, compounds of Formula (V) are selected from the group consisting of aza-analogues of A-623 (AMG-623), AG-284, AI-502, Allotrap 2702 (B-2702), AZD-2315, Cnsnqic-Cyclic (802-2), Delmitide (RDP-58), Dirucotide (MBP-8298) Disitertide (NAFB-001) (P-144), dnaJP1 (AT-001), Edratide (TV-4710), F-991, FAR-404, Glaspimod (SKF-107647), Glatiramer (COP-1), GMDP, IPP-201101, Icatibant (JE 049)(HOE-140), MS peptide, Org-42982 (AG-4263), Pentigetide (TA-521), PI-0824, PI-2301, PLD-116, PMX-53, PTL-0901, RA peptide, TCMP-80, Thymodepressin, Thymopentin (TP-5), Tiplimotide (NBI-5788), or ZP-1848; and have utility in the treatment of allergy and immunology disorders.

In certain embodiments, compounds of Formula (V) are selected from the group consisting of aza-analogues of A-71378, AC-162352 (PYY 3-36), AC-253, AG2/102, AKL-0707 (LAB GHRH), Albiglutide (GSK-716155), AOD-9604, BAY-73-7977, BIM-44002, BMS-686117, BRX-0585, CJC-1131 (DAC:GLP-1), CJC-1134 (PC-DAC) (Exendin-4), CJC-1295 (DAC:GRF), CP-95253, CVX-096 (PF-4856883), Davalintide (AC-2307), Exenatide (AC-2993) (LY-2148568), Exsulin (INGAP Peptide), Glucagon, ISF402, Liraglutide (NN-2211), Lixisenatide (AVE-0010) (ZP-10), LY-2189265, LY-548806, nafarelin (RS 94991), NBI-6024, Obinepitide (TM-30338), Peptide YY 3-36, PF-4603629, Pramlintide, R-7089, Semaglutide (NN-9535), SST analog, SUN-E7001 (CS-872), Taspoglutide (BIM-51077), Tesamorelin (TH-9507), TH-0318, TKS-1225 (Oxyntomodulin), TM-30339, TT-223 (E1-INT), Unacylated ghrelin (AZP-01) (TH-0332), or ZT0131, and have utility in the treatment of metabolic disordrs (e.g., alleviate one or more symptom(s) of a metabolic disorder).

In certain embodiments, compounds of Formula (V) are selected from the group consisting of aza-analogues of A-75998, Buserelin, Cetrorelix (NS-75), Detirelix (RS-68439), Ganirelix (Org-37462) (RS-26306), Iturelix, Nafarelin (RS-94991), or triproletin (WY-42462); and have utility in the treatment of fertility.

In certain embodiments, compounds of Formula (V) are selected from the group consisting of aza-analogues of AC-100 and p-1025, and have utility in the treatment of dental disorders.

In certain embodiments, compounds of Formula (V) are selected from the group consisting of aza-analogues of ACV-1, Conantokin G, CJC-1008 (DAC: Dynorphin A), Contulakin G (CGX-1007), CR-665, CR-845, Dynorphin A, E-2078, Felypressin, Frakefamide (LEF-576) (SPD-759) (BCH-3963), HP-228, Icatibant (JE-049) (HOE-140), KAI-1678, Leconotide (AM-336), Metkephamide (LY-127623), MPL-TLB100, NT-13, SYN-1002, TX14(A), Xen-2174, and Ziconotide (SNX-111); and have utility in the treatment of pain.

In certain embodiments, compounds of Formula (V) are selected from the group consisting of aza-analogues of Afamelanotide (EP-1647) (CUV-1647) (Melanotan I), AZX-100, DPK-060, DSC-127, Hemoparatide (PTH (1-37)), Hexapeptide copper II (PC-1358), Pexiganan (MSI-78), PTH (7-34), PXL-01, SKF-110679 (U-75799E), or Thymosin beta-4; and have utility in the treatment of dermatologic conditions (e.g., alleviate one or more symptom(s) of a dermatologic condition).

In certain embodiments, compounds of Formula (V) are selected from the group consisting of aza-analogues of AF-37702, Bivalirudin (BG-8865), carfilomib, (PR-171), CTCE-0214, ETRX 101, H-142, OGP 10-14L, Ornithine vasopressin, peg-TPOmp (RWJ-800088), R-1516, Romiplostim (AMG-531), and TP-9201; and have utility in the treatment of hematology disorders (e.g., alleviate one or more symptom(s) of a hematology disorder).

In certain embodiments, compounds of Formula (V) are selected from the group consisting of aza-analogues of Albuvirtide, ALG-889, Alloferon, ALX-40-4C, CB-182804, CB-183315, CZEN-002, Enfuvirtide (T-20), Glucosamyl muramyl tripeptide, Golotimod (SCV-07), GPG-NH2, hLF (1-11), IMX-942, Iseganan (IB-367), Murabutide (VA-101) (CY-220), Neogen, NP-213, Oglufanide (IM-862), Omiganan (CPI-226), OP-145, p-1025, P-113 (PAC-113), Pep-F (5K), R-15-K, Sifuvirtide, SPC-3, Thymalfasin, Thymonoctan (FCE-25388), Tifuvirtide (R-724) (T-1249), TRI-1144, VIR-576, or XOMA-629; and have utility as an antimicrobial or antiviral agent.

In certain embodiments, compounds of Formula (V) are selected from the group consisting of aza-analogues of ALTY-0601, B27PD, BDM-E, BIM-23190, CBT-101, Compstatin (POT-4), Eledoisin (ELD-950), and LYN-001, and have utility in the treatment of ophthalmologic disorders.

In certain embodiments, compounds of Formula (V) are selected from the group consisting of aza-analogues of Atosiban (ORF-22164), Barusiban (FE-200400), Carbetocin, Cargutocin (Y-5350), Deslorelin, Oxytocin, or TT-235, and have utility in the treatment of OB-GYN disorders.

In certain embodiments, compounds of Formula (V) are selected from the group consisting of aza-analogues of Aviptadil (PSD-510), Bremelanotide (PT-141), C-peptide (SPM-933), Desmopressin, EA-230, Lypressin, MER-104, MT-11 (PT-14), SKF-101926, or Vasopressin, and have utility in the treatment of urologic conditions (e.g., alleviate one or more symptom(s) of a urologic condition).

In certain embodiments, compounds of Formula (V) are selected from the group consisting of aza-analogues of AC-100, BA-058, Calcitonin (Human), Calcitonin (Salmon), Elcatonin, I-040302 (KUR-112), PTHrP-(1-36), Rusalatide (TP-508), SAN-134, Teriparatide (LY-333334), or ZT031; and have utility in the treatment of bones and connective tissue disorders.

In certain embodiments, compounds of Formula (V) are selected from the group consisting of aza-analogues of BIO-1211, CGRP (LAB-CGRP), Glucosamyl muramyl tripeptide, GMDP, Icrocaptide (ITF-1697), Lucinactant, Lusupultide (BY-2001), NPC-567, NPY (24-36) (PTL-041120), or Secretin (human) (PGN-52) (R-52); and have utility in the treatment of respiratory conditions (e.g., alleviate one or more symptom(s) of a respiratory condition).

In certain embodiments, compounds of Formula (V) are selected from the group consisting of aza-analogues of Casokefamide, CCK (25-33), Lagatide (BN-52080), Larazotide (AT-1001) (SPD-550), Linaclotide (MD-1100) (MM-41775), Nepadutant (MEN-11420), Nifalatide (BW942C), ROSE-010 (GTP-010) (LY-307161), Somatostatin, Somatostatin (D-Trp, D-Cys analog), SP-304 (Guanilib), Teduglutide (ALX-0600), Terlipressin, Triletide (Z-420) (ZAMI-420), Vapreotide (RC-160), ZP-1846, or ZP-1846; and have utility in the treatment of gastroenterologic disorders (e.g., alleviate one or more symptom(s) of a gastroenterologic disorder).

In certain embodiments, compounds of Formula (V) are selected from the group consisting of aza-analogues of CJC-1295 (DAC:GRF), DG-3173 (PTR-3173), Dopastatin (BIM-23A760), EP-51216 (EP-51389), Examorelin (EP-23905) (W-6003), GTP-200 (GTP-300), 1pamorelin (NNC-26-0161), Iturelix (ORF-23541), KP-101 (GHRP-1), Lanreotide (ITM-014), Octreotide (SMS-201-995), Pasireotide (SOM-230), Pralmorelin, rGRF, SUN-11031, TH-9506, ZT0131, or vapreotide (RC-160); and have utility in the treatment of endocrinology disorders (e.g., alleviate one or more symptom(s) of a gastroenterologic disorder).

Example 1

Synthesis of Benzotriazole-Based Aza Amino Acid Derivatives; a Readily Reactive Building Blocks for Coupling

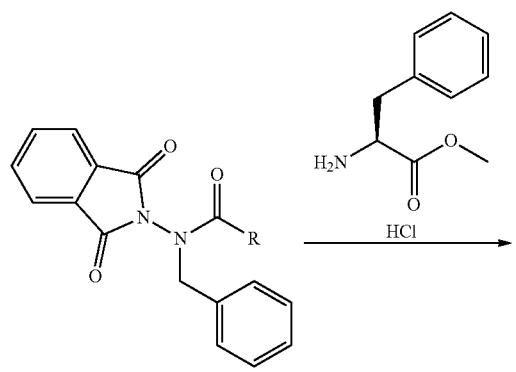

-continued

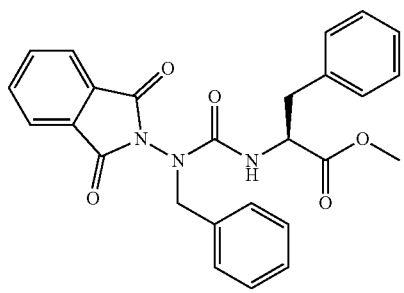 [SMILES: COC(=O)[C@H](Cc1ccccc1)NC(=O)N(Cc1ccccc1)N1C(=O)c2ccccc2C1=O]

| R = | Reaction Conditions | Isolated Yield (% wt) |
|---|---|---|
| HBt | 1.5eq Amino acid<br>2.0eq DIPEA<br>Acetonitrile<br>40° C., 20 hours | 70% |
| 5-CF$_3$—HBt | 1.5eq Amino acid<br>2.0eq DIPEA<br>Acetonitrile<br>40° C., 20 hours | 80% |
| HOBt | 1.1eq Amino acid<br>2.0eq DIPEA<br>Acetonitrile<br>25° C., 1 hour | 91% |

In contrast to HBt and 5-CF3-HBt-based derivatives, HOBt based derivatives are reactive and produced high yield coupling within an hour and room temperature. Such conditions are compatible for solid and solution phase coupling.

Example 2

Synthesis of N-Phth-1-OH-Benzotriazole (HOBt) Building Blocks

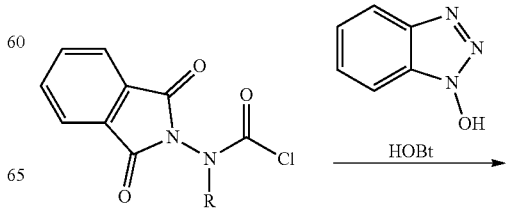

-continued

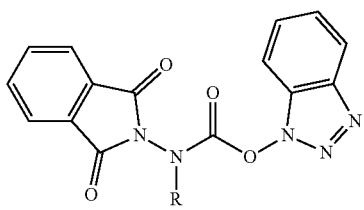

| Product | Reaction Conditions | Isolated Yield and Stability |
|---|---|---|
| R = (benzyl) | 1.5eq HOBt<br>1.5eq DIPEA<br>DCM with 4% DMF<br>25° C., 0.5 hr | 90% |
| R = (CH2-CO-O-tBu) | 1.5eq HOBt<br>1.5eq DIPEA<br>DCM with 4% DMF<br>25° C., 0.5 hr | 75% |
| R = (N-Boc indolylmethyl) | 1.5eq HOBt<br>1.5eq DIPEA<br>DCM with 4% DMF<br>25° C., 0.5 hr | 77% |
| R = (tri-Boc guanidinylpropyl) | 1.5eq HOBt<br>1.5eq DIPEA<br>DCM with 4% DMF<br>25° C., 0.5 hr | 47% (the yield is reduced due to the deprotection of Boc groups on the molecule) |

The Boc and Fmoc protection strategy was tried and overall, the yield was low and multiple byproducts were observed. Therefore, it was decided to focus on the Phth protection. Phth represent an attractive protecting group compared to traditional peptide protecting groups such as Fmoc and Boc for the following reasons:

Compared to Fmoc-NH— or Boc-NH—, Phth-N lacks of NH provides superiority as protecting group in the aza chemistry. NH in Fmoc-NH— and Boc-NH— complicates stability, reactivity and reaction condition for coupling efficiency.

Phth deprotection requires unique conditions that do not compromise any of the amino acid side chain protecting agents. In certain embodiments, about 60% hydrazine hydrate in DMF for 1 hour at room temperature is used to achieve this purpose.

Example 3

Assessing the Compatibility of HOBt Aza Building Blocks in the Presence of Traditional Alpha Amino Protecting Groups (e.g. Phth, Fmoc and Boc) with Other Protecting Synthesis and Stability

| Product | Reaction Conditions | Isolated Yield and Stability |
|---|---|---|
| R = Boc; R' = H | 1.5eq HOBt<br>1.5eq DIPEA<br>DCM with 4% DMF<br>25° C., 0.5 hr | 94%<br>Stable white solid<br>Partially stable in solution that comprised yield of coupling |
| R = Fmoc | 1.5eq HOBt<br>1.5eq DIPEA<br>DCM with 4% DMF<br>25° C., 0.5 hr | 89%<br>Stable white solid<br>Partially stable in solution that comprised yield of coupling |
| R, R' = Phth | 1.5eq HOBt<br>1.5eq DIPEA<br>DCM with 4% DMF<br>25° C., 0.5 hr | 90%<br>Stable white solid<br>Stable in organic solvents such as acetone, dichloromethane, acetonitrile, DMF at room temperature for weeks |

The issues with stability were observed when the N-1 is protected with R=Boc or Fmoc and R'=H. This is due to the presence of NH that leads to undesirable intramolecular cyclization and formation oxadiazoles (Future Med. Chem. (2011) 3(9), 1139-1164) Org. Biomol. Chem., 2015, 13, 59-63. Boc and Fmoc form an unwanted side reaction of carboxyanhydride in peptide synthesis with acid halogenation reagent (Acc. Chem. Res. 1996, 29, 268-274; J. Am. Chem. Soc. 1996, 118, 9796-9797) and in azapeptide synthesis with hydrazine component, the oxadiazolone will be formed (Journal of Peptide Science 2013, 19, 725-729).

Example 4

1-OH-Benzotriazole (HOBt) Building Blocks Coupling Activity 1

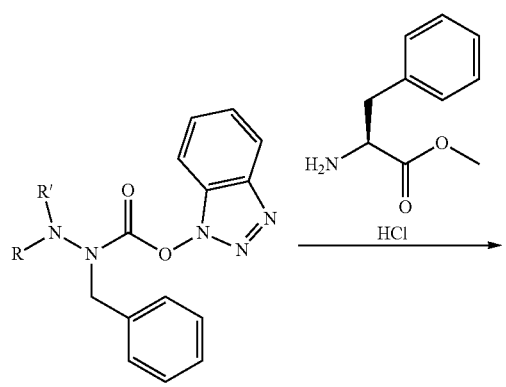

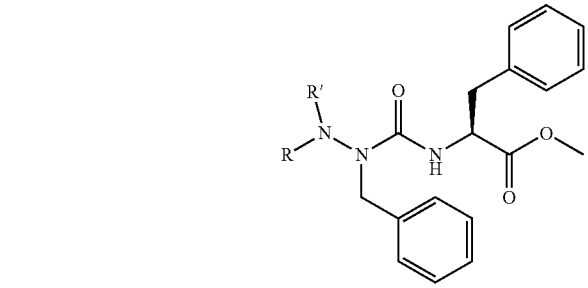

| Product | Reaction Conditions | Isolated Yield |
|---|---|---|
| R = Boc; R' = H 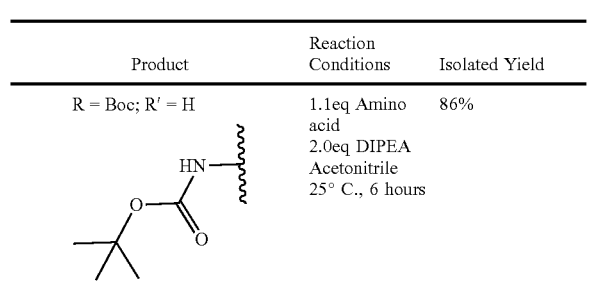 | 1.1eq Amino acid<br>2.0eq DIPEA<br>Acetonitrile<br>25° C., 6 hours | 86% |
| R = Fmoc; R' = H 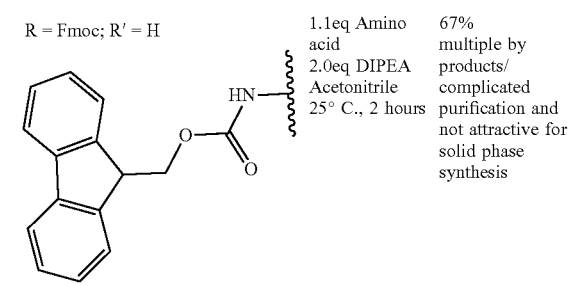 | 1.1eq Amino acid<br>2.0eq DIPEA<br>Acetonitrile<br>25° C., 2 hours | 67%<br>multiple by products/<br>complicated purification and not attractive for solid phase synthesis |

| Product | Reaction Conditions | Isolated Yield |
|---|---|---|
| R, R' = Phth 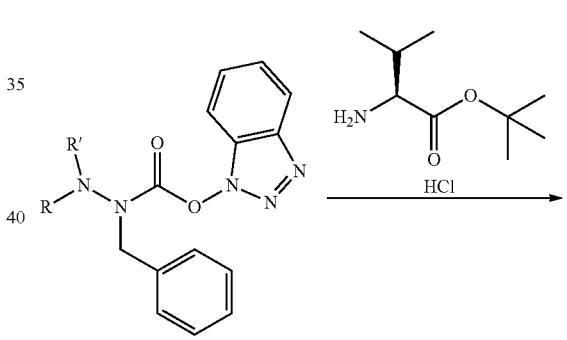 | 1.1eq Amino acid<br>2.0eq DIPEA<br>Acetonitrile<br>25° C., 1 hour | 91% |

Upon testing the coupling reactions, low yield, multiple byproducts, and up to 6 hours reaction conditions when N-alpha was protected with Fmoc and Boc. In contrast, Phth protection provided a higher yield and a shorter time reaction.

Example 5

1-OH-Benzotriazole (HOBt) Building Blocks Coupling Activity 2

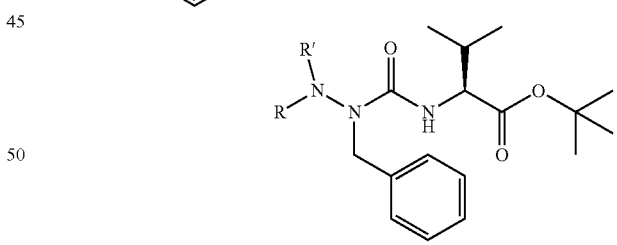

| Product | Reaction Conditions | Isolated Yield |
|---|---|---|
| R = Boc; R' = H 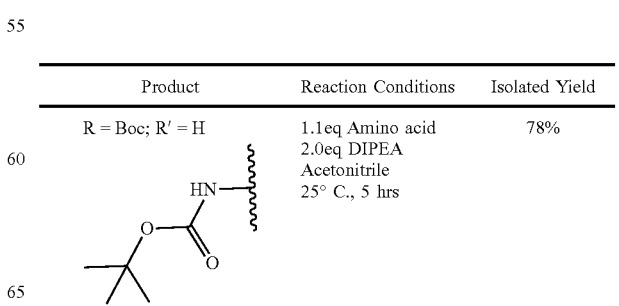 | 1.1eq Amino acid<br>2.0eq DIPEA<br>Acetonitrile<br>25° C., 5 hrs | 78% |

-continued

| Product | Reaction Conditions | Isolated Yield |
|---|---|---|
| R, R' = Phth 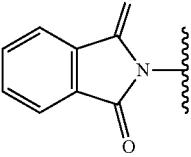 | 1.1eq Amino acid<br>2.0eq DIPEA<br>Acetonitrile<br>25° C., 1 hr | 96% |

Example 6

Examples of Synthesized N-Phth-Di-Azapeptides

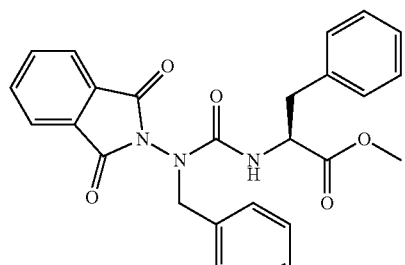

(91% yield)
m/z 458.47 $(M + H)^+$
m/z 480.47 $(M + Na)^+$

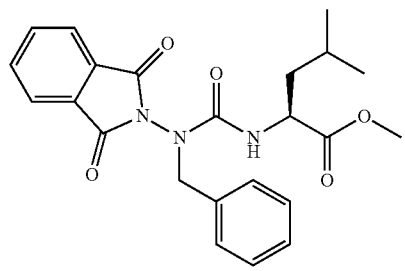 [SMILES: COC(=O)[C@H](CC(C)C)NC(=O)N(Cc1ccccc1)N1C(=O)c2ccccc2C1=O]

(94% yield)
m/z 466.33 $(M + H)^+$
m/z 488.40 $(M + Na)^+$

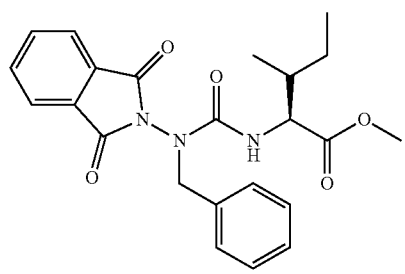 [SMILES: CCC(C)[C@H](NC(=O)N(Cc1ccccc1)N1C(=O)c2ccccc2C1=O)C(=O)OC]

(95% yield)
m/z 424.33 $(M + H)^+$
m/z 446.53 $(M + Na)^+$

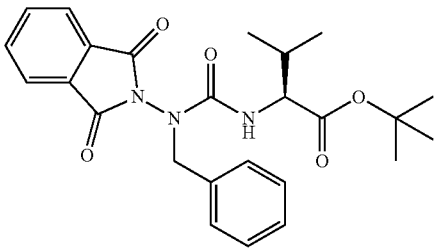 [SMILES: CC(C)[C@H](NC(=O)N(Cc1ccccc1)N1C(=O)c2ccccc2C1=O)C(=O)OC(C)(C)C]

(96% yield)
m/z 452.27 $(M + H)^+$
m/z 474.27 $(M + Na)^+$

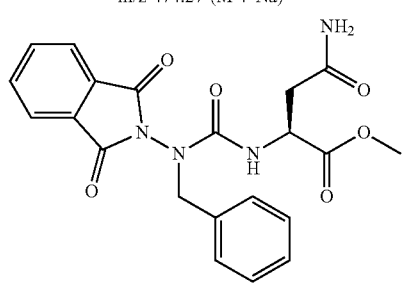

(90% yield)
m/z 467.33 $(M + H)^+$
m/z 489.27 $(M + Na)^+$

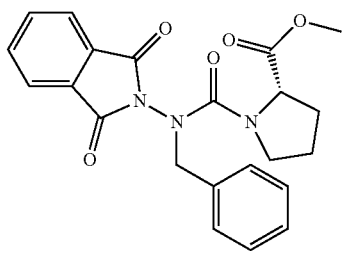 [SMILES: COC(=O)[C@@H]1CCCN1C(=O)N(Cc1ccccc1)N1C(=O)c2ccccc2C1=O]

(97% yield)
m/z 408.40 $(M + H)^+$
m/z 430.47 $(M + Na)^+$

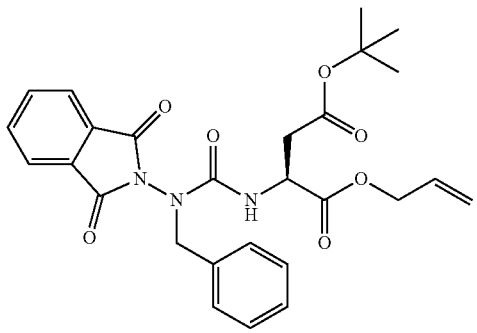 [SMILES: C=CCOC(=O)[C@H](CC(=O)OC(C)(C)C)NC(=O)N(Cc1ccccc1)N1C(=O)c2ccccc2C1=O]

(92% yield)
m/z 508.20 $(M + H)^+$
m/z 530.40 $(M + Na)^+$

-continued

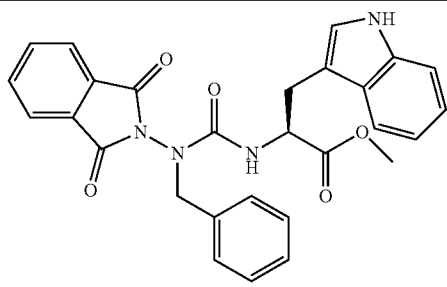

(96% yield)
m/z 497.40 (M + H)+
m/z 519.60 (M + Na)+

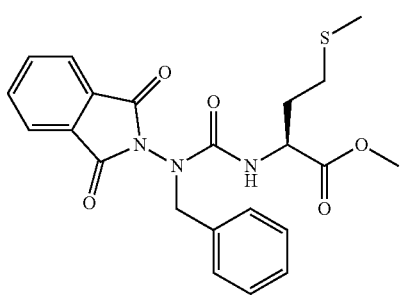 [SMILES: COC(=O)[C@H](CCSC)NC(=O)N(Cc1ccccc1)N1C(=O)c2ccccc2C1=O]

(90% yield)
m/z 442.33 (M + H)+
m/z 464.33 (M + Na)+

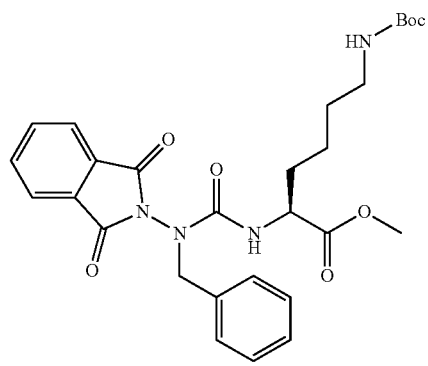 [SMILES: COC(=O)[C@H](CCCCNC(=O)OC(C)(C)C)NC(=O)N(Cc1ccccc1)N1C(=O)c2ccccc2C1=O]

(81% yield)
m/z 539.20 (M + H)+
m/z 561.33 (M + Na)+

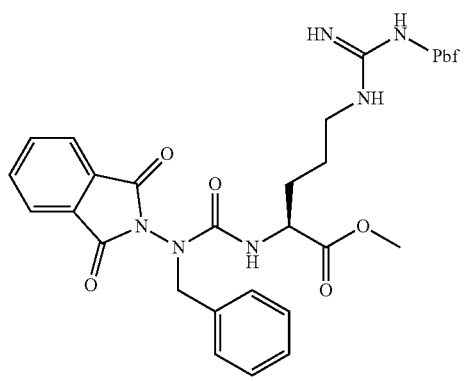

(94% yield)
m/z 719.47 (M + H)+
m/z 741.33 (M + Na)+

-continued

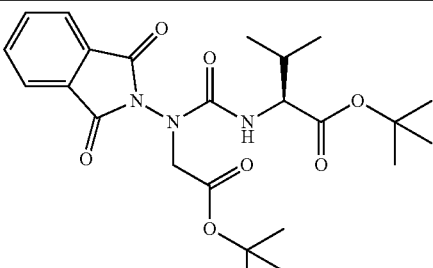

(87% yield)
m/z 476.07 (M + H)+
m/z 498.13 (M + Na)+

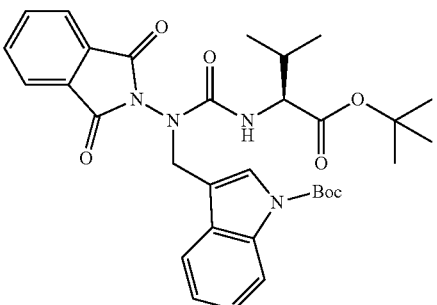

(92% yield)
m/z 591.07 (M + H)+
m/z 613.33 (M + Na)+

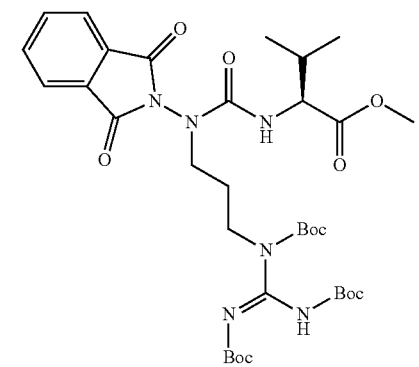 [SMILES: COC(=O)[C@@H](NC(=O)N(CCCN(C(=O)OC(C)(C)C)/C(=N/C(=O)OC(C)(C)C)NC(=O)OC(C)(C)C)N1C(=O)c2ccccc2C1=O)C(C)C]

(94% yield)
m/z 761.20 (M + H)+
m/z 783.27 (M + Na)+

Example 7

Unless otherwise noted, all starting materials were obtained from commercial suppliers and used directly without further purifications. NMR spectra were collected on 500 or 600 MHz machines. Chemical shifts were expressed in parts per million (ppm) relative to the deuterated solvent peak or the internal standard tetramethylsilane (TMS) peak. Coupling constants were in units of hertz (Hz). Splitting patterns described apparent multiplicities and were designated as s (singlet), d (doublet), t (triplet), q (quartet), m (multiplet), br (broad). Low-resolution mass spectrometry was carried out at the Thermo Scientific LTQ XL™ Linear Ion Trap mass spectrometry. TLC plates were seen under UV light with short and long wavelengths, or were observed after iodine staining, or were visualized by heating the plates upon exposure to a solution of ammonium (VI) molybdate tetrahydrate and cerium (IV) sulfate tetrahydrate. Flash column chromatography (FCC) was implemented using silica gel 60 (230-400 mesh) and employed a stepwise solvent polarity gradient, correlated with TLC mobility. HPLC was performed using Waters system combining a 1525 binary PUMP. The analytical column was a Phenomenex Kinetex 2.6 μm EVO C18 analytical column, 100 Å 150×4.6 mm. Chromatography was performed at ambient temperature with a flow rate of 1 mL/min with a linear gradient from Water (0.05% TFA): CAN (0.05% TFA)[95:5] to Water (0.05% TFA): CAN (0.05% TFA) [5:95] in 15 minutes, monitored/detected UV at 254 nm and/or 215 nm by 2998 Photodiode Array (PDA) Detector. For preparative ["prep"] HPLC was performed using Waters Prep 150 LC System combining a 2545 Binary Gradient Module. The Preparative Column was a waters Xselect Peptide CSH C18 OBD Prep Column, 130 Å, 5 μm, 19 mm×150 mm. Chromatography was performed at ambient temperature with a flow rate of 18 mL/min with a linear gradient from Water (0.1% FA): CAN (0.1% FA)[95:5] to Water (0.1% FA): CAN (0.1% FA) [5:95] in 12 minutes with a 2 min hold. Monitored/detected UV at 254 nm and/or 215 nm by 2998 Photodiode Array (PDA) Detector. Peptide elongation was performed on Wang resin (0.3 mmol/g, 0.33 g, 0.1 mmol) using standard Fmoc/tert-butyl chemistry on a Tribute peptide synthesizer (Protein Technologies, Inc.) using HCTU/NNM activation in DMF.

General Procedure to Prepare alkyl-(1,3-dioxo-1,3-dihydro-isoindol-2-yl)-carbamic acid benzotriazol-1-yl ester To a solution of N-alkyl-aminophthalimide (1 mmol) in anhydrous DCM (10 mL) at 0° C. was added phosgene (1.5 mmol, 1M solution in toluene). The stirred mixture was warmed up to room temperature and stirred at this temperature for 0.5 hours. The reaction was stopped by evaporating the excess volatiles and the crude mixture was dried under vacuum pump for 1 hour to give the corresponding acyl chlorides which were re-dissolved in anhydrous DCM (10 mL). To the above solution was added HOBt (1.5 mmol in 400 uL DMF) and DIPEA (1.5 mmol). The reaction mixture was stirred at room temperature for half hour. The reaction mixture was mixed with water (25 mL) and was extracted with EtOAc (25 mL×4). The combined organic layer was washed with brine (25 mL), dried over $Na_2SO_4$, filtered and evaporated under vacuum, and the residue was purified by FCC to give the corresponding alkyl-(1,3-dioxo-1,3-dihydro-isoindol-2-yl)-carbamic acid benzotriazol-1-yl ester.

The following four building blocks were prepared:

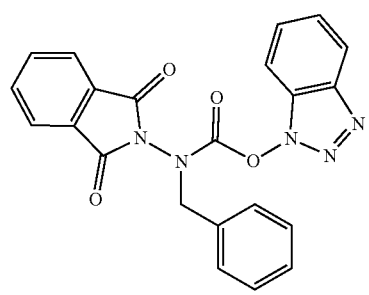

1

Benzyl-(1,3-dihydro-isoindol-2-yl)-carbamic acid benzotriazol-yl-ester

After FCC purification, the Phth-Azphe-Obt was isolated as white foam (371 mg, 90%).

Two conformations were observed in acetone-d6 NMR with ratio of 1:4; ESI mass spectroscopy (MH$^+$=414).

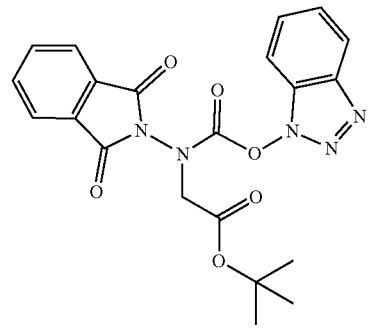

2

{(Benzotriazol-1-yloxycarbonyl)-(1,3-dioxo-1,3-dihydro-isoindol-2-yl)-amino}-Acetic Acid Tert-Butyl Ester After FCC purification the Phth-Azasp-Obt was isolated as white foam (328 mg, 75%).

Two conformations were observed in acetone-d6 NMR with ratio of 1:2; ESI mass spectroscopy (MH$^+$=438).

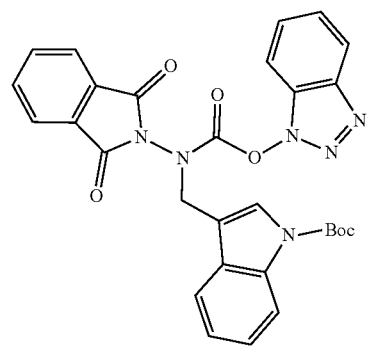

3

3-{[(Benzotriazol-1-yloxycarbonyl)-(1,3-dioxo-1,3-dihydro-isoindol-2-yl)-amino]-methyl}-indole-1-Carboxylic Acid Tert-Butyl Ester After FCC purification the Phth-Aztrp-Obt was isolated as white foam (425 mg, 77%).

Two conformations were observed in acetone-d6 NMR with ratio of 1:6; ESI mass spectroscopy (MH$^+$=553).

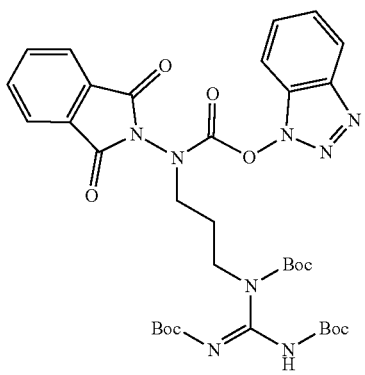

4

(1,3-Dioxo-1,3-dihydro-isoindol-2-yl)-[3-(N,N',N''-tri-Boc)-guanidino-propyl]-Carbamic Acid Benzotriazol-1-yl-Ester After FCC purification the Phth-Azarg-Obt was isolated as white foam (339 mg, 47%).

ESI mass spectroscopy (MH$^+$=723).

Example 8

Procedure to Prepare N-Boc-Azphe-Phe-Ome Ester

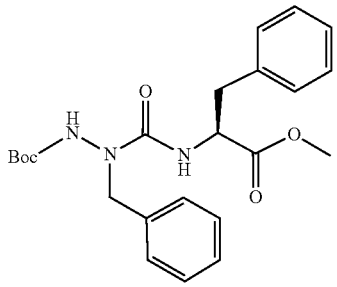

5 tert-butyl (S)-2-benzyl-2-(1-methoxy-1-oxo-3-phenylpropan-2-yl)carbamoyl)hydrazine-1-carboxylate To a solution of the Boc-Azphe-Obt (0.065 mmol) in CAN (0.5 mL) was added L-phenylalanine methyl ester HCl salt (0.072 mmol) and DIPEA (0.13 mmol). The reaction mixture was stirred at room temperature for 6 hours. Then, the reaction mixture was mixed with water (5 mL) and was extracted with EtOAc (5 mL×4). The combined organic layer was washed with brine (5 mL), dried over Na$_2$SO$_4$, filtered and evaporated under vacuum, and the residue was purified by FCC to give the corresponding compound (24 mg, 86%). $^1$HNMR (500 MHz, Acetoned$_6$) δ 8.09 (br, 1H), 7.25 (m, 10H), 6.25 (br, 1H), 4.70 (m, 3H), 3.67 (s, 3H), 3.11 (m, 2H), 1.23 (s, 9H); $^{13}$C NMR (125 MHz, Acetoned$_6$) δ 173.1, 158.0, 155.2, 138.4, 137.9, 130.3, 129.5, 129.4, 129.2, 129.1, 128.1, 127.5, 81.2, 55.5, 52.3, 51.2, 38.8, 28.3. ESI mass spectroscopy (MH$^+$=428).

Example 9

Procedure to Prepare N-Boc-Azphe-Val-OtBu Ester

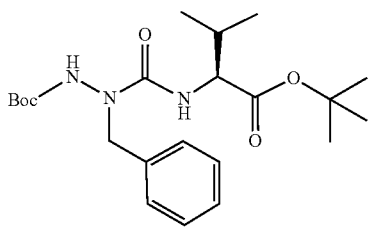

6 tert-butyl (S)-2-benzyl-2-(1-(tert-butoxy)-3-methyl-1-oxobutan-2-yl)carbamoyl)hydrazine-1-carboxylate To a solution of the Boc-Azphe-Obt (0.065 mmol) in CAN (0.5 mL) was added L-valine tert-butyl ester HCl salt (0.072 mmol) and DIPEA (0.13 mmol). The reaction mixture was stirred at room temperature for 5 hours then the reaction mixture was mixed with water (5 mL) and was extracted with EtOAc (5 mL×4). The combined organic layer was washed with brine (5 mL), dried over Na$_2$SO$_4$, filtered and evaporated under vacuum, and the residue was purified by FCC to give the corresponding compound (24 mg, 86%). $^1$HNMR (500 MHz, Acetoned$_6$) δ 8.03 (br, 1H), 7.31 (m, 5H), 6.02 (br, 1H), 4.86-4.40 (br, 2H), 4.26 (m, 1H), 2.18 (m, 1H), 1.54 (s, 9H), 1.41 (s, 9H), 0.90 (d, J=10 Hz, 3H), 0.84 (d, J=10 Hz, 3H); $^{13}$C NMR (125 MHz, Acetoned$_6$) δ 172.2, 158.3, 155.1, 138.6, 129.5, 129.4, 128.1, 81.9, 81.2, 59.5, 51.6, 32.4, 28.3, 28.0, 19.3, 17.9. ESI mass spectroscopy (MH$^+$=422).

Example 10

Procedure to Prepare N-Fmoc-Azphe-Phe-Ome Ester

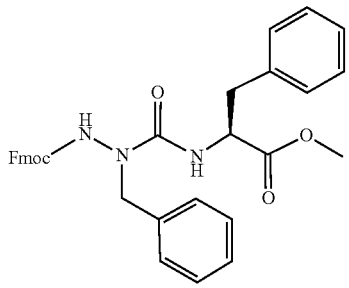

7

(9H-fluoren-9-yl)methyl (S)-2-benzyl-2-(1-methoxy-1-oxo-3-phenylpropan-2-yl)carbamoyl)hydrazine-1-Carboxylate To a solution of the Fmoc-Azphe-Obt (0.05 mmol) in CAN (0.5 mL) was added L-phenylalanine methyl ester HCl salt (0.055 mmol) and DIPEA (0.1 mmol). The reaction mixture was stirred at room temperature for 2 hours then the reaction mixture was mixed with water (5 mL) and was extracted with EtOAc (5 mL×4). The combined organic layer was washed with brine (5 mL), dried over Na₂SO₄, filtered and evaporated under vacuum, and the residue was purified by FCC to give the corresponding compound (18 mg, 67%). ¹HNMR (500 MHz, Acetoned₆) δ 8.81 (br, 1H), 7.88 (d, J=10 Hz, 2H), 7.67 (d, J=10 Hz, 2H)7.46 (m, 2H), 7.36-7.21 (m, 12H), 6.32 (br, 1H), 4.86-4.60 (br, 2H), 4.65 (m, 1H), 4.42 (br, 2H), 4.20 (m, 1H), 3.65 (s, 3H), 3.08 (m, 2H); ¹³C NMR (125 MHz, Acetoned₆) 6173.0, 157.7, 156.0, 144.7, 142.1, 138.2, 137.8, 130.2, 129.5, 129.2, 129.1, 128.6, 128.1, 128.0, 127.4, 126.2, 120.8, 67.7, 60.5, 55.5, 52.2, 51.2, 47.8, 38.6. ESI mass spectroscopy (MH⁺=550).

Example 11

General Procedure to Prepare N-Phth-Azphe-Aa-Ome or OtBu Esters

To a solution of the Phth-Azphe-Obt in CAN was added L-Amino acid methyl or tert-butyl esters and DIPEA. The reaction mixture was stirred at room temperature for 1 hour. Then, the reaction mixture was mixed with water and extracted with EtOAc (×4). The combined organic layer was washed with brine, dried over Na₂SO₄, filtered and evaporated under vacuum, and the residue was purified by FCC to give the corresponding compound. The following compounds were prepared.

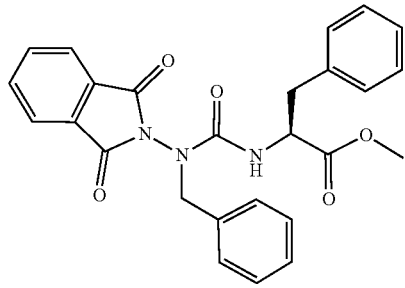

8 methyl (benzyl(1,3-dioxoisoindolin-2-yl)carbamoyl)-L-phenylalaninate

Phth-Azphe-Obt (0.065 mmol) in CAN (0.5 mL) was added L-phenylalanine methyl ester HCl salt (0.072 mmol) and DIPEA (0.13 mmol). Yield (25 mg, 91%). ¹HNMR (500 MHz, Acetoned₆) δ 7.93-7.80 (m, 4H), 7.39-7.30 (m, 2H), 7.25-7.15 (m, 8H), 6.75 (br, 1H), 4.85 (Abq, J=20 Hz, 2H), 4.58 (m, 1H), 3.62 (s, 3H), 3.02 (dd, J=15, 6 Hz, 1H), 2.90 (dd, J=15, 8 Hz, 1H); ¹³C NMR (125 MHz, Acetoned₆) δ 172.9, 165.9, 165.8, 156.9, 138.1, 137.0, 135.6, 131.1, 130.2, 129.9, 129.1, 128.9, 128.4, 127.4, 124.2, 124.1, 56.3, 53.1, 52.1, 38.2. ESI mass spectroscopy (MH⁺=458).

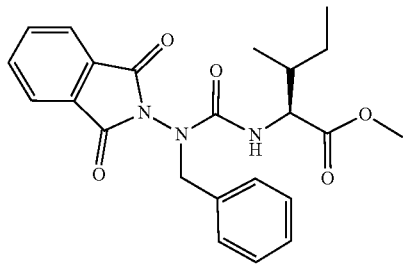

9 methyl (benzyl(1,3-dioxoisoindolin-2-yl)carbamoyl)-L-alloisoleucinate

Phth-Azphe-Obt (0.048 mmol) in CAN (0.5 mL) was added L-isoleucine methyl ester HCl salt (0.053 mmol) and DIPEA (0.096 mmol). Yield (19.2 mg, 95%). ¹HNMR (500 MHz, Acetoned₆) δ 7.85 (m, 4H), 7.40 (m, 2H), 7.25 (m, 3H), 6.65 (br, 1H), 4.85 (Abq, 2H), 4.35 (m, 1H), 3.65 (s, 3H), 1.75 (m, 1H), 1.43 (m, 1H), 1.12 (m, 1H), 0.80 (m, 6H); ¹³C NMR (125 MHz, Acetoned₆) δ 173.2, 166.1, 166.0, 157.2, 138.1, 137.1, 135.6, 131.3, 131.2, 130.0, 129.0, 128.5, 124.2, 124.1, 59.2, 53.4, 51.9, 37.7, 25.8, 15.8, 11.3. ESI mass spectroscopy MH⁺=424).

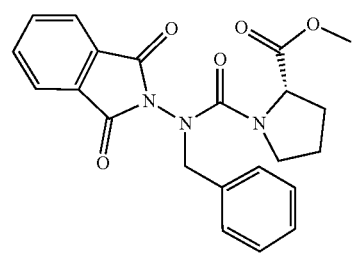

10 methyl (benzyl(1,3-dioxoisoindolin-2-yl)carbamoyl)-L-prolinate

Phth-Azphe-Obt (0.048 mmol) in CAN (0.5 mL) was added L-proline methyl ester HCl salt (0.053 mmol) and DIPEA (0.096 mmol). Yield (19.0 mg, 97%). ¹HNMR (500 MHz, Acetoned₆) δ 7.90 (m, 4H), 7.42 (m, 2H), 7.22 (m, 3H), 4.80 (Abq, 2H), 4.35 (m, 1H), 3.45 (s, 3H), 3.35 (m, 2H), 2.12 (m, 1H), 1.90-1.78 (m, 3H); ¹³C NMR (125 MHz, Acetoned₆) δ 173.3, 166.0, 165.8, 158.5, 137.1, 136.0, 130.5, 130.3, 128.9, 128.4, 124.3, 61.6, 50.5, 55.2, 51.9, 48.8, 25.0. ESI mass spectroscopy (MH⁺=408).

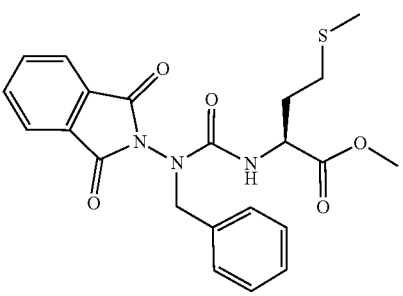

11 methyl (benzyl(1,3-dioxoisoindolin-2-yl)carbamoyl)-L-methioninate

Phth-Azphe-Obt (0.048 mmol) in CAN (0.5 mL) was added L-methionine methyl ester HCl salt (0.053 mmol) and DIPEA (0.096 mmol). Yield (19.0 mg, 90%). $^1$HNMR (500 MHz, Acetone$_6$) δ 7.85 (m, 4H), 7.38 (m, 2H), 7.22 (m, 3H), 6.98 (br, 1H), 4.90 (Abq, 2H), 4.55 (m, 1H), 3.65 (s, 3H), 2.50 (m, 2H), 2.02 (s, 3H), 1.98 (m, 1H), 1.80 (m, 1H); $^{13}$C NMR (125 MHz, Acetone$_6$) δ 173.3, 166.0, 165.8, 157.3, 137.1, 135.7, 131.2, 131.1, 130.1, 128.9, 128.4, 124.2, 124.1, 53.6, 53.0, 52.3, 32.0, 30.8, 15.2. ESI mass spectroscopy (MH$^+$=442).

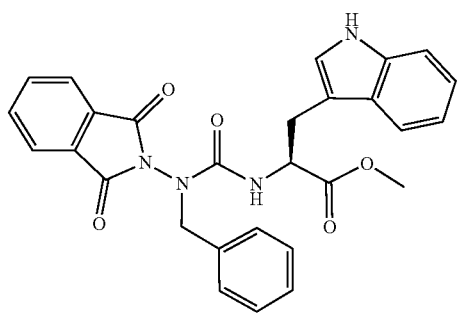

12 methyl (benzyl(1,3-dioxoisoindolin-2-yl)carbamoyl)-L-tryptophanate

Phth-Azphe-Obt (0.048 mmol) in CAN (0.5 mL) was added L-tryptophan methyl ester HCl salt (0.053 mmol) and DIPEA (0.096 mmol). Yield (23 mg, 96%). $^1$HNMR (500 MHz, Acetone$_6$) δ 10.0 (bs, 1H), 7.90-7.80 (m, 4H), 7.51 (d, J=7.9 Hz, 1H), 7.35 (m, 3H), 7.21 (m, 3H), 7.12 (m, 1H), 7.04 (t, J=7.15 Hz, 1H), 6.96 (t, J=7.3, 1H), 6.74 (m, 1H), 4.86 (Abq, J=14.8 Hz, 2H), 4.65 (m, 1H), 3.59 (s, 3H), 3.19 (m, 1H), 3.05 (m, 1H); $^{13}$C NMR (125 MHz, Acetone$_6$) δ 173.3, 165.9, 157.0, 137.4, 137.0, 135.6, 131.0, 129.9, 128.9, 128.4, 124.5, 124.4, 124.3, 122.1, 119.6, 118.9, 112.1, 110.7, 55.7, 53.2, 52.2, 28.2. ESI mass spectroscopy (MH$^+$=497).

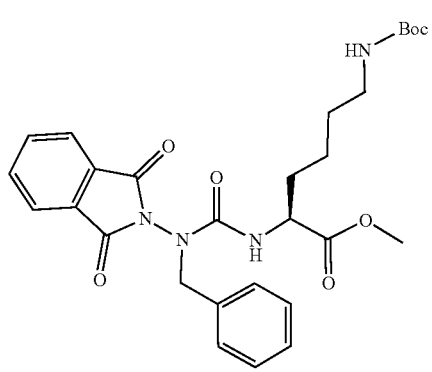

13 methyl N2-(benzyl(1,3-dioxoisoindolin-2-yl)carbamoyl)-N6-(tert-butoxycarbonyl)-L-lysinate Phth-Azphe-Obt (0.048 mmol) in CAN (0.5 mL) was added L-N-Boc-lysine methyl ester HCl salt (0.053 mmol) and DIPEA (0.096 mmol). Yield (21.0 mg, 81%). $^1$HNMR (500 MHz, Acetone$_6$) δ 7.85 (m, 4H), 7.40 (m, 2H), 7.22 (m, 3H), 6.89 (d, J=8.0 Hz, 1H), 6.86 (br, 1H), 5.85 (br, 1H), 4.90 (Abq, 2H), 4.39 (m, 1H), 3.60 (s, 3H), 3.05 (m, 2H), 1.70 (m, 1H), 1.50-1.40 (m, 14H); $^{13}$C NMR (125 MHz, Acetone$_6$) δ 173.7, 166.0, 165.9, 157.3, 156.6, 137.1, 135.6, 131.2, 131.1, 130.1, 128.9, 128.4, 124.2, 124.1, 78.3, 54.6, 53.1, 52.1, 40.8, 32.0, 29.4, 28.7, 23.8. ESI mass spectroscopy (MH$^+$=539).

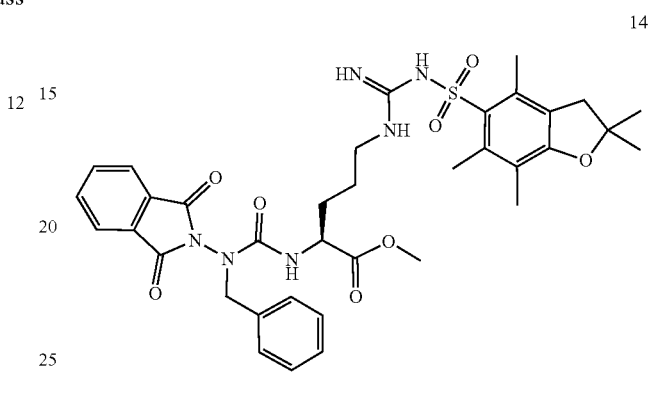

14 methyl N2-(benzyl(1,3-dioxoisoindolin-2-yl)carbamoyl)-Nw-((2,2,4,6,7-pentamethyl-2,3-dihydrobenzofuran-5-yl)sulfonyl)-L-argininate Phth-Azphe-Obt (0.048 mmol) in CAN (0.5 mL) was added L-N-Pbf-arginine methyl ester HCl salt (0.053 mmol) and DIPEA (0.096 mmol). Yield (33.0 mg, 94%). $^1$HNMR (500 MHz, Acetone$_6$) δ 7.85 (m, 4H), 7.38 (m, 2H), 7.20 (m, 3H), 6.95 (br, 1H), 6.49 (br, 2H), 4.90 (Abq, J=15 Hz, 2H), 4.35 (m, 1H), 3.64 (s, 3H), 3.18 (m, 2H), 3.00 (s, 2H), 2.55 (s, 3H), 2.48 (s, 3H), 2.05 (s, 3H), 1.75 (m, 1H), (1.60-1.50 (m, 3H), 1.45 (s, 6H); $^{13}$C NMR (125 MHz, Acetone$_6$) δ 173.4, 166.0, 165.8, 158.9, 157.4, 157.2, 138.7, 137.0, 135.6, 135.5, 132.8, 131.1, 130.1, 128.9, 128.4, 125.3, 124.2, 124.1, 117.5, 87.0, 54.3, 53.1, 52.2, 43.6, 41.1, 28.7, 26.6, 19.5, 18.2, 12.6. ESI mass spectroscopy (MH$^+$=719).

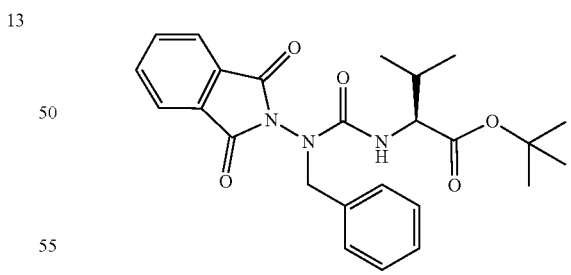

tert-butyl (benzyl(1,3-dioxoisoindolin-2-yl)carbamoyl)-L-valinate

Phth-Azphe-Obt (0.06 mmol) in CAN (0.5 mL) was added L-valine tert-butyl ester HCl salt (0.066 mmol) and DIPEA (0.12 mmol). Yield (26.0 mg, 96%). $^1$HNMR (500 MHz, Acetone$_6$) δ 7.85 (m, 4H), 7.45 (m, 2H), 7.25 (m, 3H), 6.35 (br, 1H), 4.90 (s, 2H), 4.29 (q, J$_1$=10 Hz, J$_2$=5 Hz, 1H), 1.95 (m, 1H), 1.42 (s, 9H), 0.89 (d, J=5.0 Hz, 3H), 0.80

(d, J=5.0 Hz, 3H); $^{13}$C NMR (125 MHz, Acetone$_6$) δ 171.7, 166.1, 157.2, 137.2, 135.6, 131.3, 131.2, 129.9, 129.0, 128.4, 124.2, 81.5, 60.8, 53.4, 31.6, 28.2, 19.5, 18.6. ESI mass spectroscopy (MH$^+$=452).

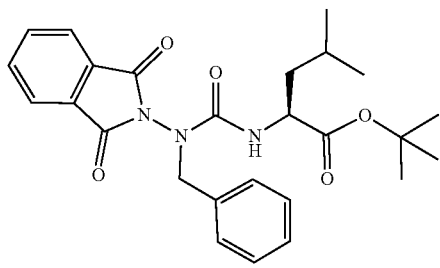

tert-butyl (benzyl(1,3-dioxoisoindolin-2-yl)carbamoyl)-L-leucinate

Phth-Azphe-Obt (0.048 mmol) in CAN (0.5 mL) was added L-leucine tert-butyl ester HCl salt (0.053 mmol) and DIPEA (0.96 mmol). Yield (21.0 mg, 94%). $^1$HNMR (500 MHz, Acetone$_6$) δ 7.85 (m, 4H), 7.40 (m, 2H), 7.22 (m, 3H), 6.72 (br, 1H), 4.90 (s, 2H), 4.35 (m, 1H), 1.70 (m, 1H), 1.45 (m, 11H), 0.92 (d, J=5 Hz, 3H), 0.85 (d, J=5 Hz, 3H); $^{13}$C NMR (125 MHz, Acetone$_6$) δ 172.9, 166.0, 165.9, 157.3, 137.2, 135.5, 131.2, 130.0, 128.9, 128.3, 124.2, 124.1, 81.1, 53.8, 53.0, 41.3, 28.1, 25.2, 23.3, 21.8. ESI mass spectroscopy (MH$^+$=466).

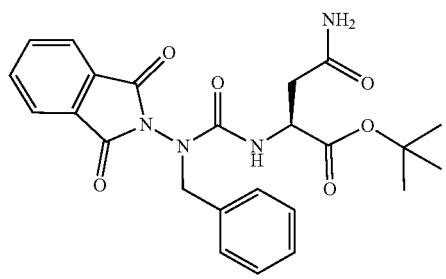 [SMILES: CC(C)(C)OC(=O)[C@H](CC(N)=O)NC(=O)N(Cc1ccccc1)N1C(=O)c2ccccc2C1=O]

tert-butyl (benzyl(1,3-dioxoisoindolin-2-yl)carbamoyl)-L-asparaginate

Phth-Azphe-Obt (0.048 mmol) in CAN (0.3 mL) and DMF (0.2 mL) was added L-asparagine tert-butyl ester HCl salt (0.053 mmol) and DIPEA (0.96 mmol). Yield (20.0 mg, 90%). $^1$HNMR (500 MHz, CD$_3$OD) δ 7.78 (m, 4H), 7.30 (m, 2H), 7.18 (m, 3H), 4.84 (q, J$_1$=14 Hz, J$_2$=5 Hz, 2H), 4.48 (t, J=5.5 Hz, 1H), 2.70 (m, 2H), 1.42 (s, 9H); $^{13}$C NMR (125 MHz, CD$_3$OD) δ 175.3, 171.7, 166.6, 158.1, 136.1, 135.8, 131.0, 130.9, 130.6, 129.6, 129.4, 125.0, 124.9, 83.5, 53.7, 52.6, 37.9, 28.5. ESI mass spectroscopy (MH$^+$=467).

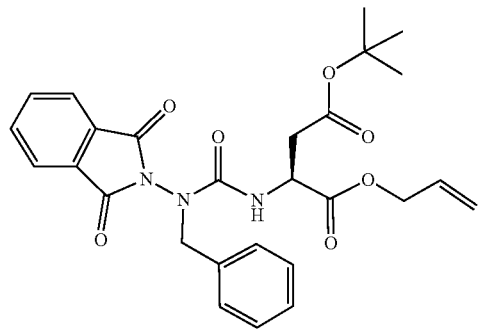

1-allyl 4-(tert-butyl) (benzyl(1,3-dioxoisoindolin-2-yl)carbamoyl)-L-aspartate

Phth-Azphe-Obt (0.048 mmol) in CAN (0.5 mL) was added L-aspartic (O-tBu)-allyl ester HCl salt (0.053 mmol) and DIPEA (0.96 mmol). Yield (22.0 mg, 92%). $^1$HNMR (500 MHz, Acetone$_6$) δ 7.89 (m, 4H), 7.43 (m, 2H), 7.23 (m, 3H), 6.95 (br, 1H), 5.35 (m, 1H), 5.23 (m, 1H), 4.90 (Abq, J=15 Hz, 2H), 4.77 (q, J$_1$=15 Hz, J$_2$=5 Hz, 2H), 4.61 (d, J=15 Hz, 2H), 2.80 (m, 1H), 2.60 (m, 11H), 1.40 (s, 9H); $^{13}$C NMR (125 MHz, Acetone$_6$) δ 171.4, 170.0, 165.7, 156.9, 137.0, 135.7, 133.2, 131.0, 129.9, 128.9, 128.4, 124.2, 118.0, 81.3, 66.1, 53.1, 51.4, 38.3, 28.1. ESI mass spectroscopy (MH$^+$=508).

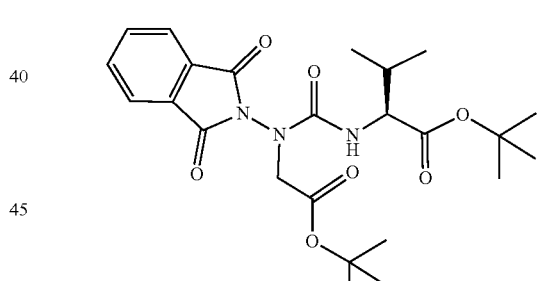

tert-butyl ((2-(tert-butoxy)-2-oxoethyl)(1,3-dioxoisoindolin-2-yl)carbamoyl)-L-valinate Phth-Azasp-Obt (0.023 mmol) in CAN (0.2 mL) was added L-valine tert-butyl ester HCl salt (0.025 mmol) and DIPEA (0.046 mmol). Yield (9.5 mg, 87%). $^1$HNMR (500 MHz, Acetone$_6$) δ 7.94 (s, 4H), 6.59 (br, 1H), 4.90 (s, 2H), 4.37 (Abq, J=20 Hz, 2H), 4.16 (dd, J=10 Hz, 1H), 1.95 (m, 1H), 1.42 (s, 9H), 1.39 (s, 9H), 0.92 (d, J=10 Hz, 3H), 0.85 (d, J=10 Hz, 3H); $^{13}$C NMR (125 MHz, Acetone$_6$) δ 171.7, 168.0, 165.8, 156.7, 135.6, 131.6, 124.3, 124.2, 81.7, 81.5, 60.8, 51.9, 31.7, 28.1, 28.0, 19.5, 18.7. ESI mass spectroscopy (MH$^+$=476).

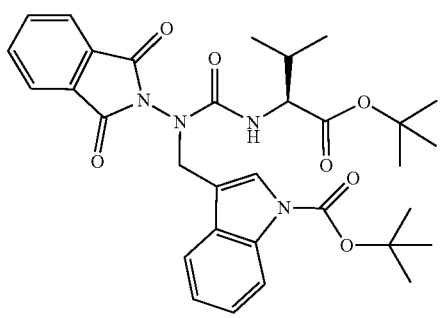

20

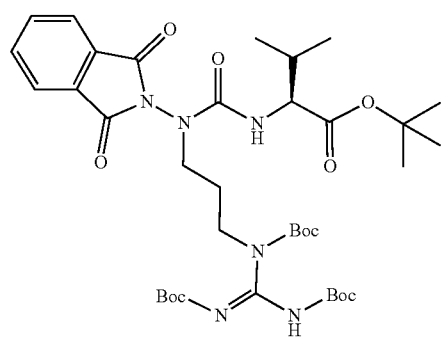

21 tert-butyl (S)-3-((3-(1-(tert-butoxy)-3-methyl-1-oxobutan-2-yl)-1-(1,3-dioxoisoindolin-2-yl)ureido)methyl)-1H-indole-1-carboxylate Phth-Aztrp-Obt (0.018 mmol) in CAN (0.15 mL) and DMF (0.15 mL) was added L-valine tert-butyl ester HCl salt (0.02 mmol) and DIPEA (0.036 mmol). Yield (10.0 mg, 94%). $^1$HNMR (500 MHz, Acetone$_6$) δ 8.08 (d, J=10 Hz, 1H), 7.97-7.81 (m, 4H), 7.78 (d, J=10 Hz, 1H), 7.65 (s, 1H), 7.31 (t, J=10 Hz, 1H), 7.21 (t, J=10 Hz, 1H), 6.50 (br, 1H), 5.10 (Abq, J=20 Hz, 2H), 4.23 (dd, J=10 Hz, 1H), 1.95 (m, 1H), 1.59 (s, 9H), 1.41 (s, 9H), 0.98 (d, J=10 Hz, 3H), 0.85 (d, J=10 Hz, 3H); $^{13}$C NMR (125 MHz, Acetone$_6$) δ 171.7, 166.1, 166.0, 157.1, 150.1, 135.6, 131.4, 131.3, 130.8, 126.6, 125.2, 124.3, 124.2, 123.3, 120.9, 117.0, 115.7, 84.2, 81.5, 60.8, 43.6, 31.6, 28.0, 19.5, 18.7. ESI mass spectroscopy (MH$^+$=591).

tert-butyl (Z)-((1,3-dioxoisoindolin-2-yl)(3-(1,2,3-tris(tert-butoxycarbonyl)guanidino)propyl)carbamoyl)-L-valinate Phth-Azlys-Obt (0.01 mmol) in CAN (0.1 mL) was added L-valine tert-butyl ester HCl salt (0.011 mmol) and DIPEA (0.02 mmol). Yield (7.0 mg, 92%). $^1$HNMR (500 MHz, Acetone$_6$) δ 10.19 (br, 1H), 7.83 (s, 4H), 6.25 (br, 1H), 4.25 (m, 1H), 4.15 (m, 1H), 3.80 (m, 2H), 1.95 (m, 1H), 1.45 (s, 37H), 1.25 (m, 2H), 0.92 (d, J=10 Hz, 3H), 0.82 (d, J=10 Hz, 3H); $^{13}$C NMR (125 MHz, Acetone$_6$) δ 171.8, 166.5, 156.9, 153.9, 135.6, 131.5, 124.3, 83.4, 81.5, 64.1, 62.3, 60.7, 48.4, 46.0, 31.7, 28.7, 28.3, 28.1, 28.0, 19.6, 18.8. ESI mass spectroscopy (MH$^+$=761).

Example 12

The following compounds were synthesized.

TABLE 1

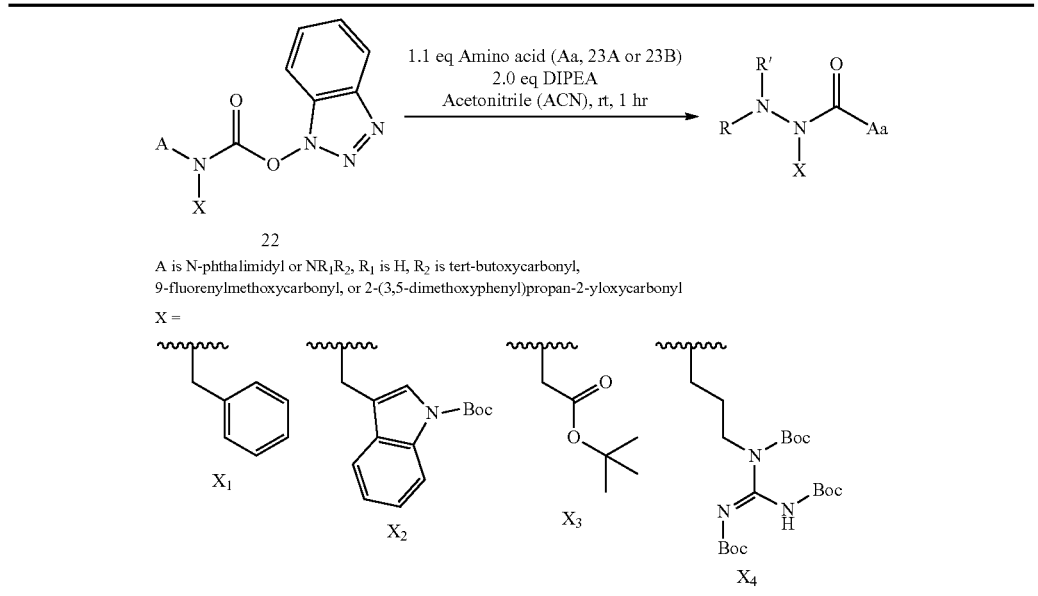

22

A is N-phthalimidyl or NR$_1$R$_2$, R$_1$ is H, R$_2$ is tert-butoxycarbonyl, 9-fluorenylmethoxycarbonyl, or 2-(3,5-dimethoxyphenyl)propan-2-yloxycarbonyl

22:

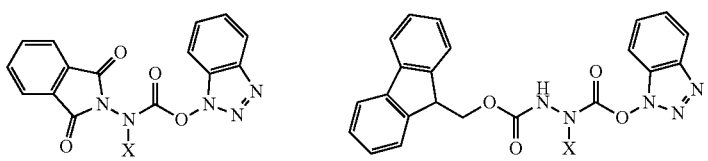

TABLE 1-continued

| compound | yield | compound | yield |
| --- | --- | --- | --- |
| (phenylalanine methyl ester) 8 (X = X₁) | 91% | 7 (X = X₁) | 67% (2 hrs RXN) |
| (valine tert-butyl ester) 15 (X = X₁) | 96% | | |
| 20 (X = X₂) | 94% | | |
| 19 (X = X₃) | 87% | | |
| 21 (X = X₄) | 92% | | |

Reaction scheme:

Compound 22 + 1.1 eq Amino acid (Aa, 23A or 23B), 2.0 eq DIPEA, Acetonitrile (ACN), rt, 1 hr → product

22

A is N-phthalimidyl or NR₁R₂, R₁ is H, R₂ is tert-butoxycarbonyl, 9-fluorenylmethoxycarbonyl, or 2-(3,5-dimethoxyphenyl)propan-2-yloxycarbonyl

X =

X₁ = benzyl

X₂ = (1-Boc-indol-3-yl)methyl

X₃ = CH₂C(O)O-tBu

X₄ = (CH₂)₃-N(Boc)-C(=N-Boc)-NH-Boc

22:

(tert-butyl carbamate–N(X)–C(O)–O-benzotriazole structure)

| compound | yield |
| --- | --- |
| (phenylalanine methyl ester) 5 (X = X₁) | 86% (6 hrs RXN) |
| (valine tert-butyl ester) 6 (X = X₁) | 78% (5 hrs RXN) |

"RXN" = reaction time

Example 13

The following compounds were synthesized.

TABLE 2

| Aa (23) | compound | yield |
|---|---|---|
| (isoleucine methyl ester) | 9 | 95% |
| (proline methyl ester) | 10 | 97% |
| (methionine methyl ester) | 11 | 90% |
| (tryptophan methyl ester) | 12 | 96% |

TABLE 2-continued
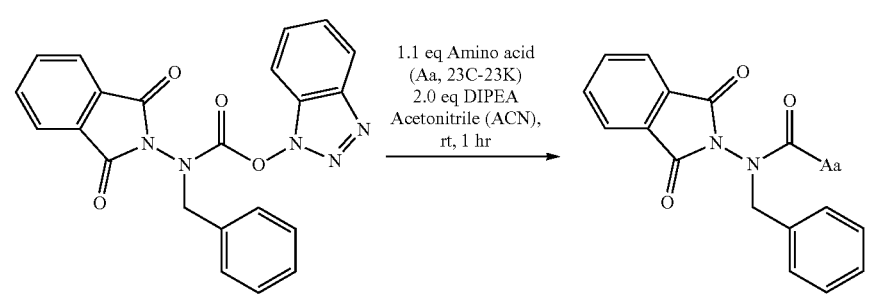
| Aa (23) | compound | yield |
|---|---|---|
| 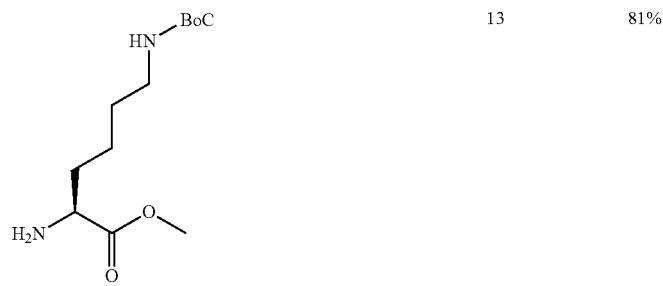 | 13 | 81% |
|  | 16 | 94% |
|  | 17 | 90% |
| 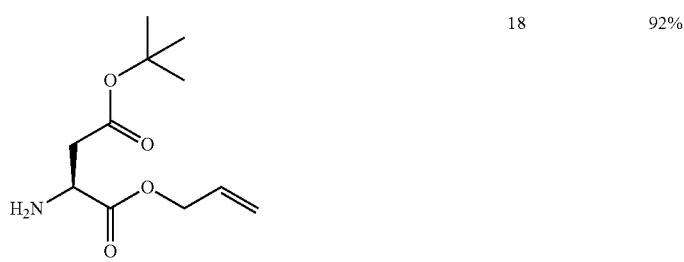 | 18 | 92% |

TABLE 2-continued

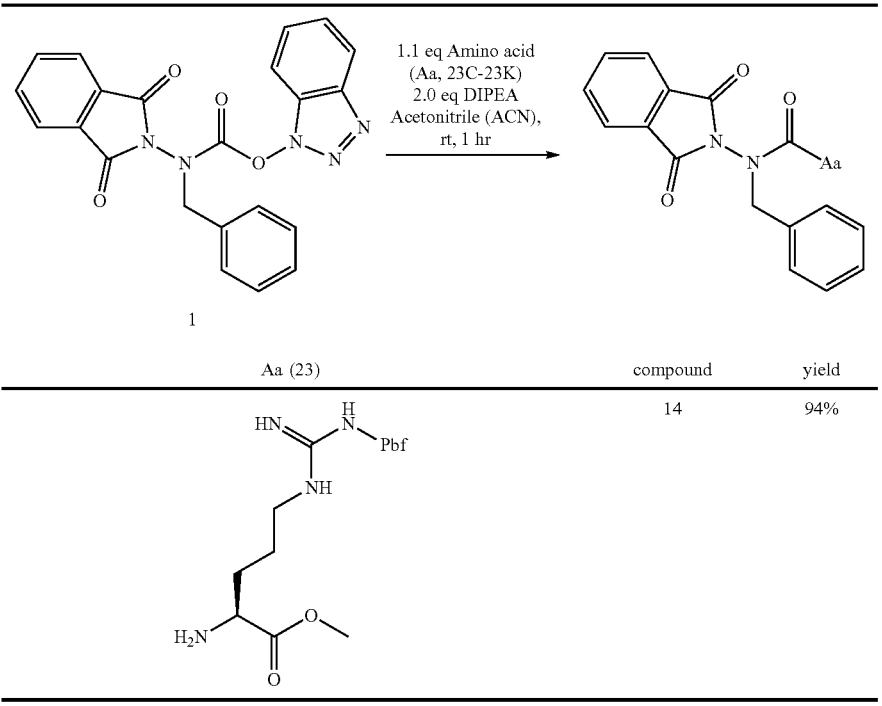

| Aa (23) | compound | yield |
|---|---|---|
| | 14 | 94% |

Example 14

Solid Phase Peptide Synthesis (SPPS) of 8Aza-Bradykinin

Compatibility and reactivity of Obt synthons with SPPS using standard Fmoc/tert-butyl chemistry was examined.

8aza-Bradykinin was selected as an example because, prior to the present invention, it was synthesized by solution phase synthesis with very low yield and was problematic in purification. The following standard SPPS procedures were used:

Resin loading: ~100 mg per mL in DMF

Swelling: DMF 10 min for 3 cycles

Fmoc Deprotection: 20% piperdine/DMF 2.5 min for 2 cycles

Coupling cycle: resin substitution: amino acid: coupling reagent: base (1:5:5:10) for 10 min 1 cycle Washing: DMF 0.5 min for 5 cycles; DCM 0.5 min for 6 cycles Capping: 50 eq. Acetic anhydride and 50 eq. Pyridine in DMF for 30 minutes (repeated cycle if needed)

Cleavage: TFA: water:triisopropylsilane (95:2.5:2.5) for 2 hours

After swelling of the Fmoc-Arg(pbf)-Wang resin (0.3 mmol/g, 0.33 g, 0.1 mmol), the Fmoc protecting group was removed using 20% piperidine in DMF. The solution of the reagent Fmoc-azphe-Obt (4 eq) in DMF was delivered automatically to the peptidyl resin and the bead suspension was shaken for 1 hour (scheme 1).

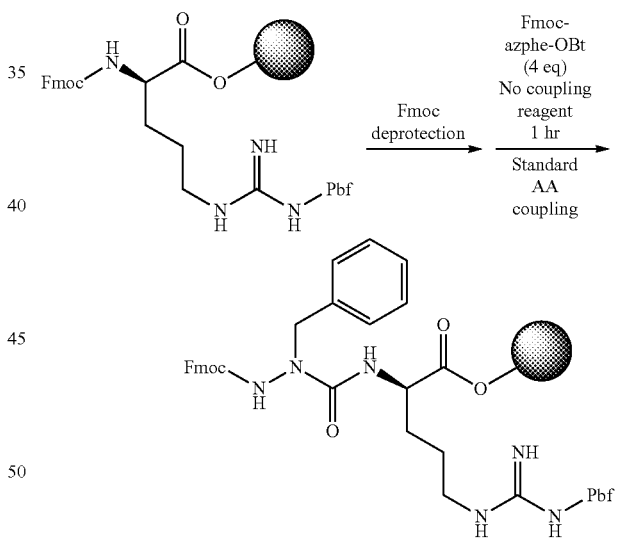

Scheme 1

In the process, the coupling activity of Fmoc-azphe-Obt with the peptidyl resin to obtain the resin-bound Fmoc-aza-Phe-Arg(pbf)-OH was studied. Since the formation of the aza-peptide bond was much slower than that of native peptide, the conventional SPPS protocol using typical coupling agents and amino acid activators cannot be directly applied to aza-peptide synthesis. In order to achieve effective acylation of the semicarbazide moiety in aza-peptide bond formation, fresh generated amino acid chloride as the coupling activator was applied. After Fmoc removal, the resin-bound $NH_2$-aza-Phe-Arg(pbf)-OH was mixed with $Na_2CO_3$ (30 eq) and Fmoc-Proline acid chloride (5 eq) in dioxane. The bead suspension was shaken for 1 hour to obtain the resin-bound Fmoc-pro-aza-Phe-Arg(pbf)-OH (scheme2). Small portion of the bead (10 mg) was cleaved and deprotected from the solid support by using 0.2 mL of TFA/H2O/TIS: 95/2.5/2.5 by volume for 1 hour. The crude azapeptide was precipitated out in cold ether (2 mL) and washed with ether (×3). RP-HPLC analysis indicated the formation desired product 24 (70%) along with missing aza-Phe side product 25 (30%) which indicating incomplete conversion of Fmoc-azphe-Obt to the resin-bound Fmoc-aza-Phe-Arg(pbf)-OH (FIG. 1). Similar observation was reported by Gibson in his synthesis of RGD-Mimetics (*J. Org. Chem.* 1999, 64, 7388-7394).

Scheme 2

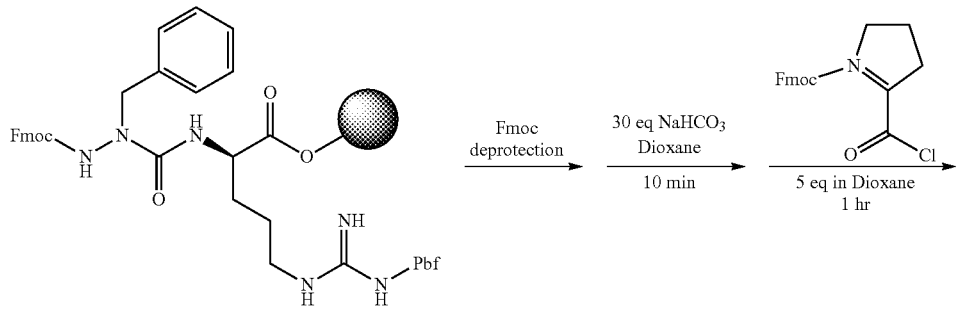

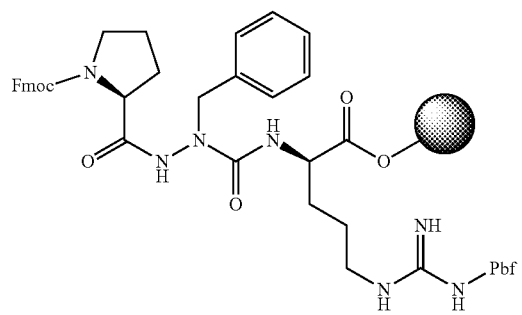

24

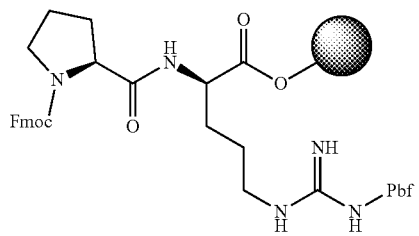

25

The Fmoc protecting group was removed using 20% piperidine in DMF and the peptidyl resin was subjected to the conventional SPPS protocol to finish the bradykinin sequence (scheme3).

Scheme 3

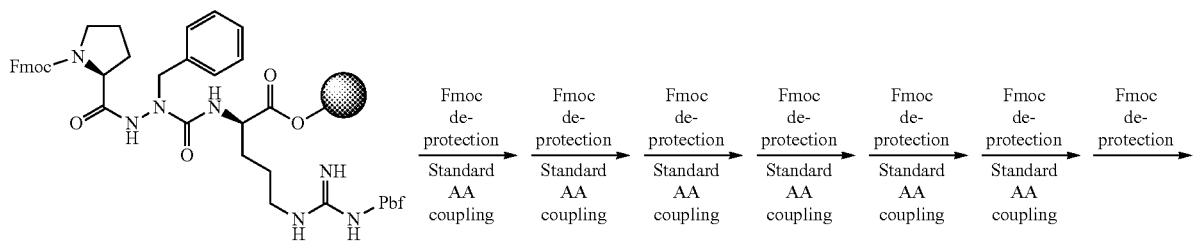

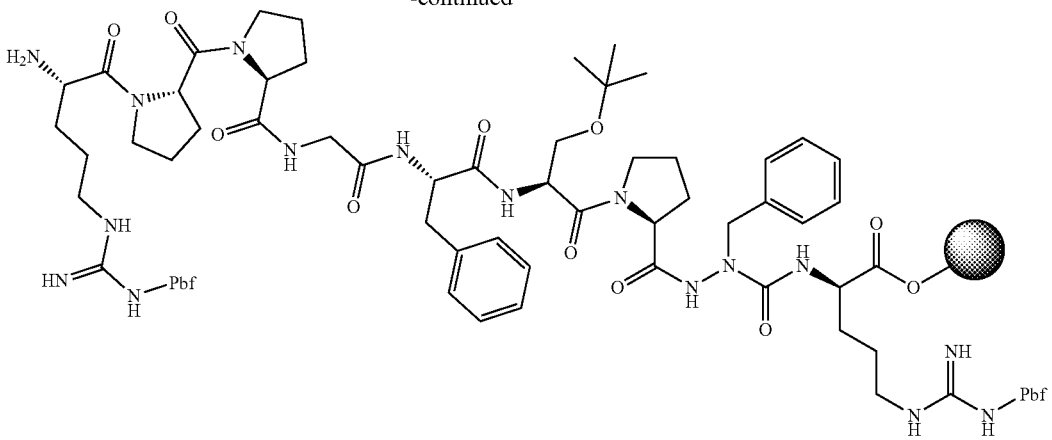

Figure 2:
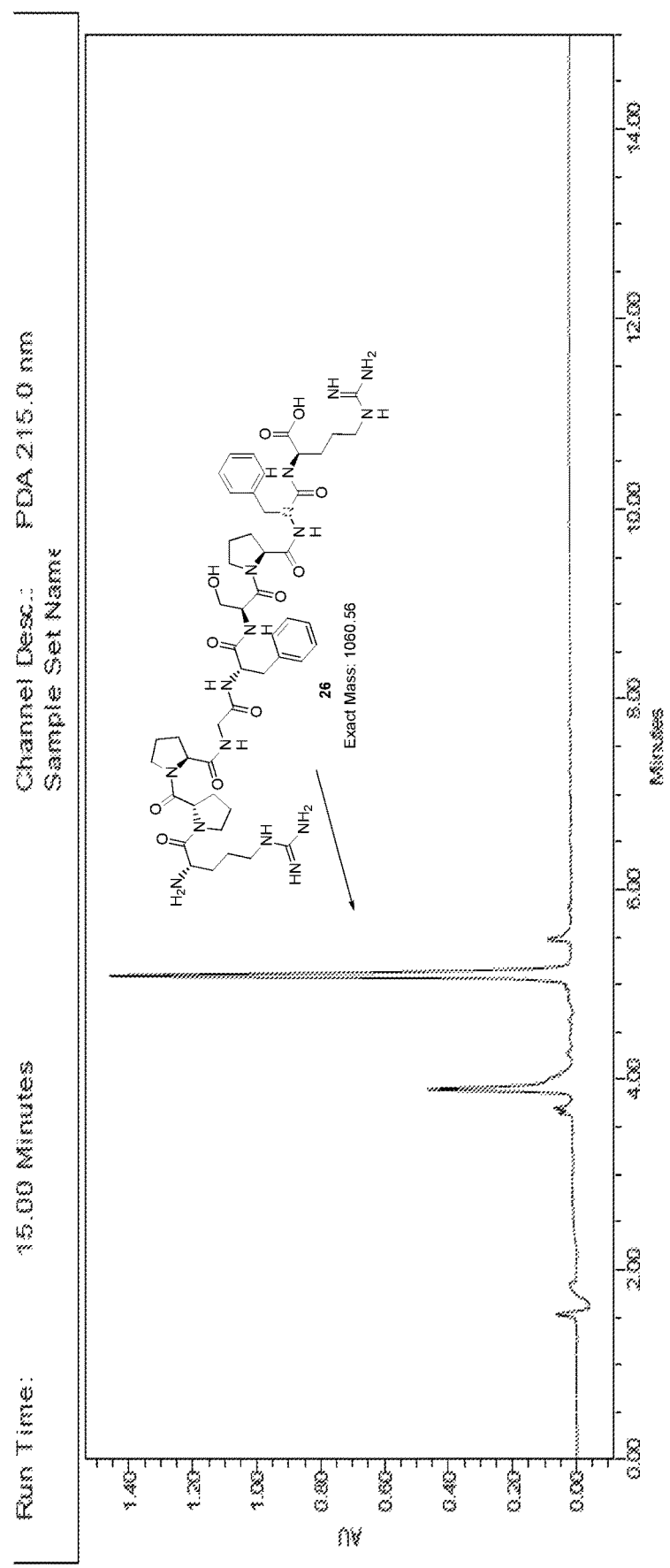
FIG. 2 is HPLC of crude 8AzaBK (26) from SPPS of Example 15.

Final cleavage and deprotection from the solid support were performed by using 2 mL of TFA/H2O/TIS: 95/2.5/2.5 by volume for 2 hours. The crude azapeptide was precipitated out in cold ether (40 mL) and washed with ether (×3) to obtain crude product (127 mg). RP-HPLC analysis indicated formation of the major desired product 8aza-Bradykinin (26) (FIG. 2).

The crude 26 was purified by RP-HPLC using Waters Prep 150 LC System combining a 2545 Binary Gradient Module. The Preparative Column was a waters Xselect Peptide CSH C18 OBD Prep Column, 130 Å, 5 μm, 19 mm×150 mm. Chromatography was performed at ambient temperature with a flow rate of 18 mL/min with a linear gradient from Water (0.1% FA): CAN (0.1% FA)[95:5] to Water (0.1% FA): CAN (0.1% FA) [50:50] in 12 minutes with a 2 min hold. Monitored/detected UV at 254 nm and/or 215 nm by 2998 Photodiode Array (PDA) Detector. Fractions containing 26 were collected and lyophilized to obtain 8aza-Bradykinin (26) (30 mg, 96% pure). The overall yield of the synthesis by SPPS is 28% within 8 hours working time.

Incomplete conversion of Fmoc-azphe-Obt to the resin-bound Fmoc-aza-Phe-Arg(pbf)-OH was reasoned as the less coupling activity of Fmoc-azphe-Obt and it can be improved by increasing the concentration of reagents content and enhance the coupling times or repeat the coupling process.

In contrast to Fmoc-azphe-Obt, Phth-azphe-Obt is more stable and active azabuilding block as shown in solution phase di-azapeptides synthesis (Table 1). Compared to Fmoc-NH— or Boc-NH—, Phth-N lacks of NH provides superiority as protecting group in the aza chemistry. NH in Fmoc-NH— and Boc-NH— complicates stability, reactivity and reaction condition for coupling efficiency. The presence of NH leads to undesirable intramolecular cyclization and formation oxadiazoles (Future Med. Chem. (2011) 3(9), 1139-1164); (Org. Biomol. Chem., 2015, 13, 59-63). In addition, Boc and Fmoc form an unwanted side reaction of carboxyanhydride in peptide synthesis with acid halogenation reagent (Acc. Chem. Res. 1996, 29, 268-274; J. Am. Chem. Soc. 1996, 118, 9796-9797) and in azapeptide synthesis with hydrazine component, the oxadiazalone will be formed (Journal of Peptide Science 2013, 19, 725-729).

The coupling activity of Phth-azphe-Obt with the peptidyl resin to obtain the resin-bound Phth-aza-Phe-Arg(pbf)-OH was investigated. After swelling of the Fmoc-Arg(pbf)-Wang resin (0.3 mmol/g, 0.33 g, 0.1 mmol), the Fmoc protecting group was removed using 20% piperidine in DMF. The solution of the reagent Phth-azphe-Obt (5 eq) in DMF was delivered automatically to the peptidyl resin and the bead suspension was shaken for 1 h (scheme 4).

Scheme 4

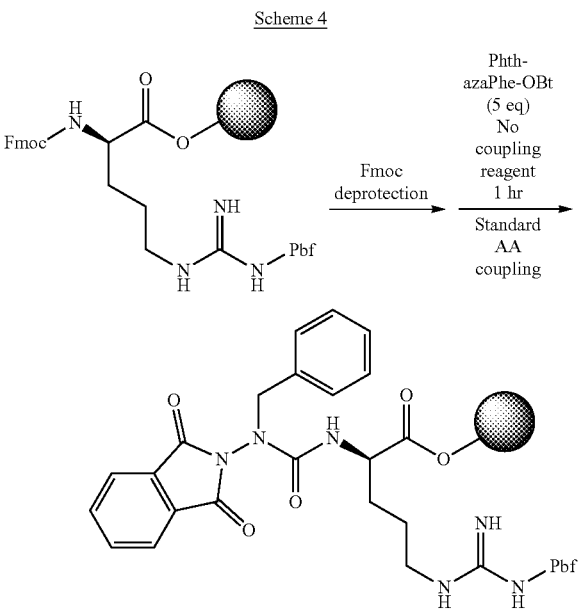

Figure 3:
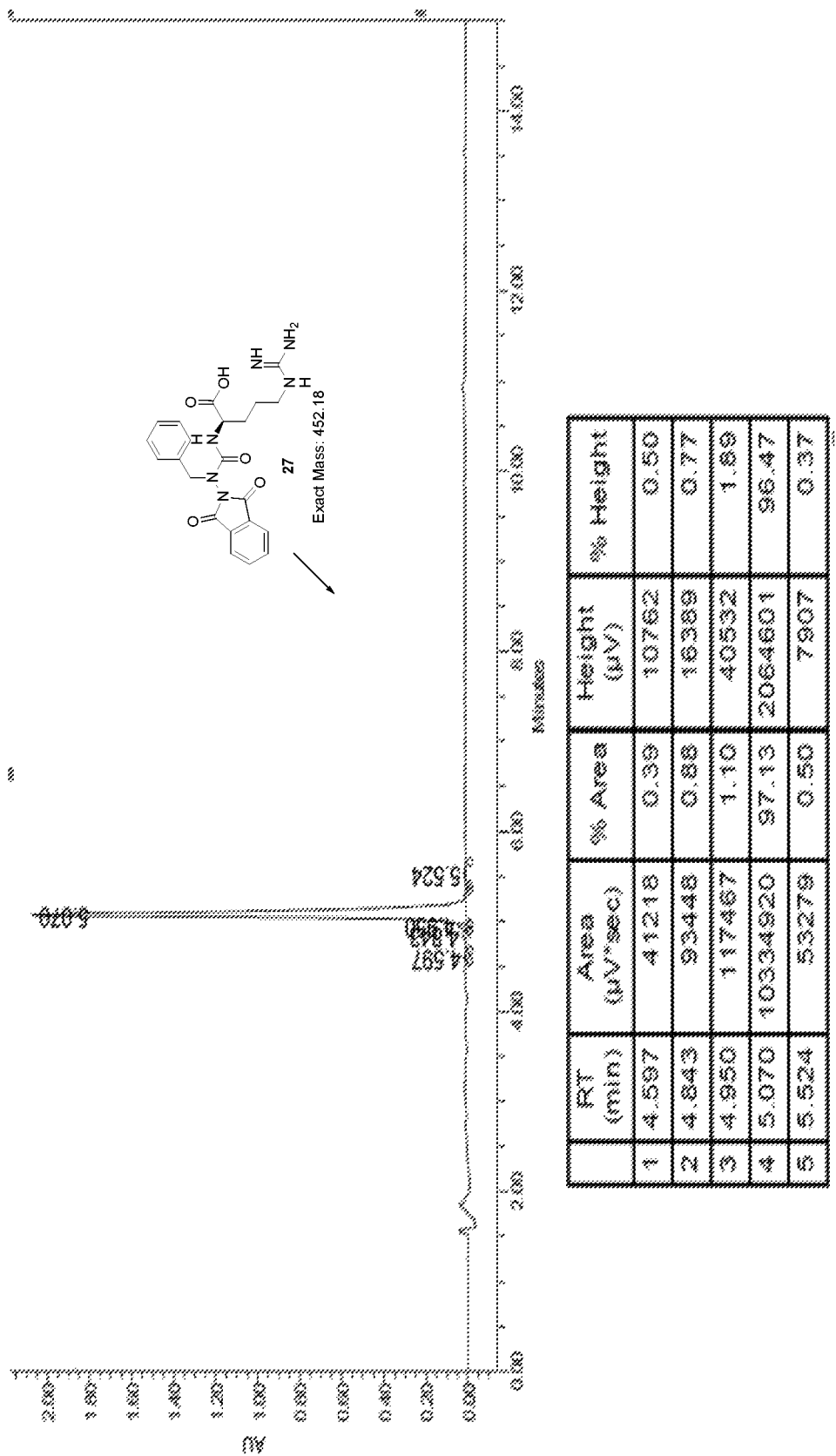
FIG. 3 is HPLC of isolated 8Aza-BK (26) of Example 15.

Small portion of the bead (10 mg) was cleaved and deprotected from the solid support by using 0.2 mL of TFA/H2O/TIS: 95/2.5/2.5 by volume for 1 hour. The crude azapeptide was precipitated out in cold ether (2 mL) and washed with ether (×3). RP-HPLC analysis indicated the formation only desired product 27 (>95%) (FIG. 3).

Phth deprotection requires conditions that do not compromise any of the amino acid side chain protecting agents. In literature, a 60% hydrazine in DMF for 1-3 h is reported to remove the phthaloyl group completely from the resin (J. Am. Chem. Soc. 1997, 119, 1556-1564). However, when the same method was applied to the resin-bound Phth-aza-Phe-Arg(pbf)-OH, after cleavage and deprotection from the solid support, RP-HPLC analysis indicated the formation only half open side product 28 (90%):

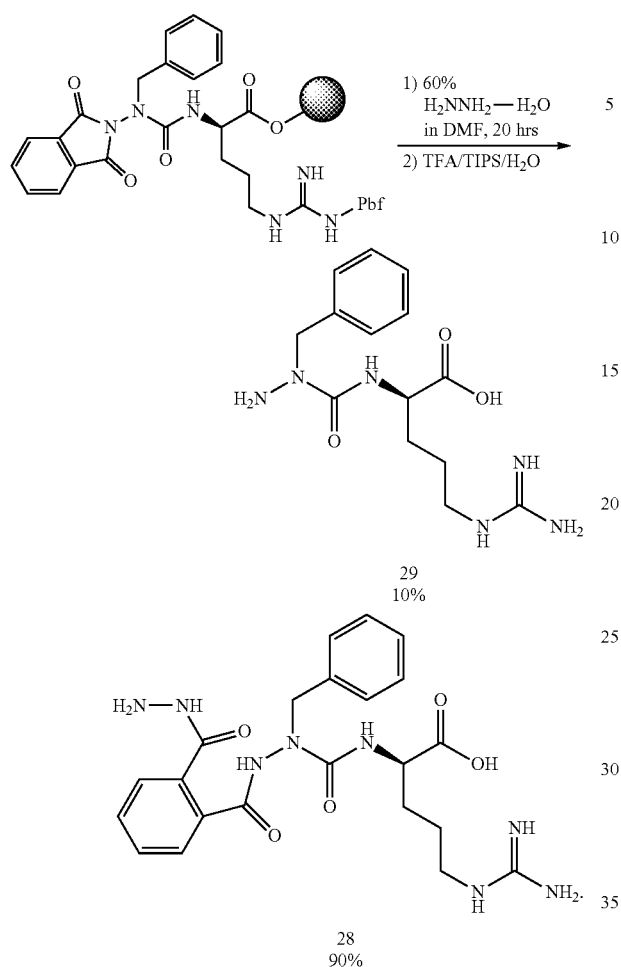

29
10%

28
90%

Different reagent, reaction time and solvents were examined to achieve the fully deprotected product (29). Among the tests, 50% MeNHNH$_2$ in anhydrous THF at room temperature for 1 hour gave 80% desired product (29).

Example 15

Synthesis of Aza-Bradykinin

8Aza-bradykinin (8-aza-BK) was synthesized from Fmoc-azPhe-OBt building block by SPPS with standard amino acid (Aa) coupling with automate mode, the overall yield of the synthesis by SPPS is 28% (97% pure). The synthetic schemes were as follows:

Scheme 1

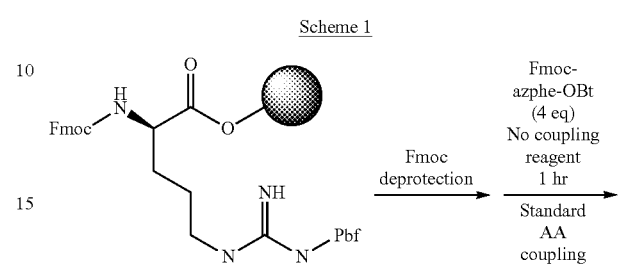

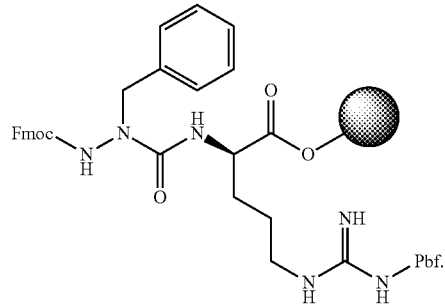

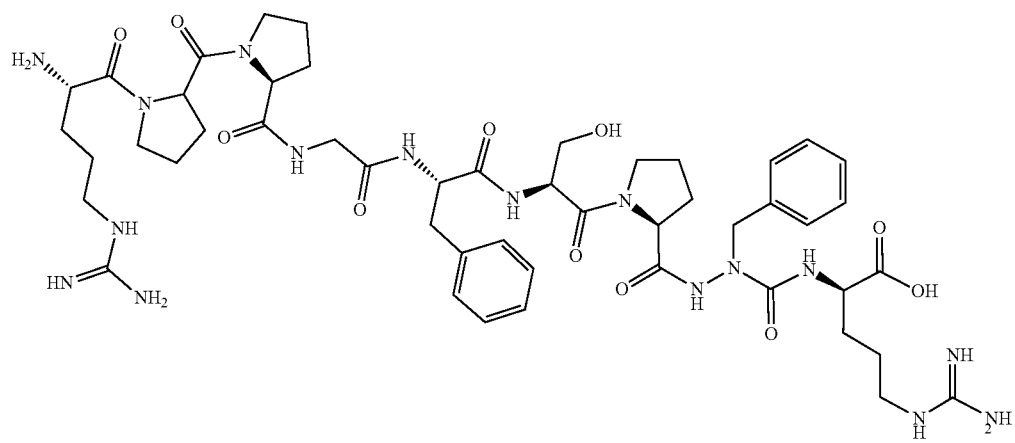 [SMILES: N=C(N)NCCC[C@H](N)C(=O)N1CCCC1C(=O)N1CCC[C@H]1C(=O)NCC(=O)N[C@@H](Cc1ccccc1)C(=O)N[C@@H](CO)C(=O)N1CCC[C@H]1C(=O)NN(Cc1ccccc1)C(=O)N[C@H](CCCNC(=N)N)C(=O)O]

Scheme 2.
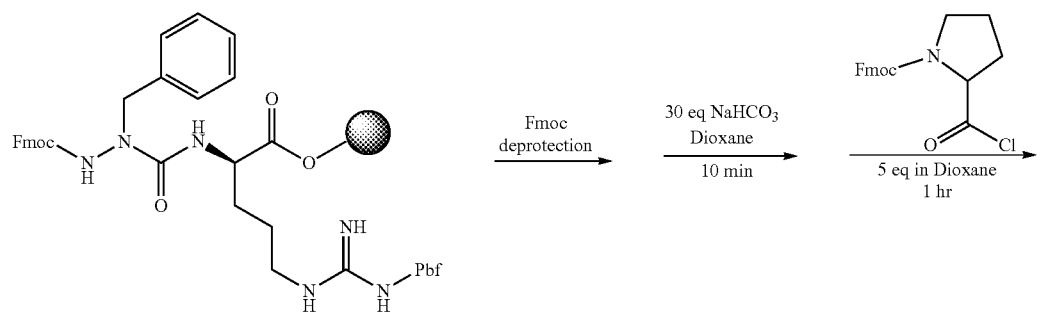
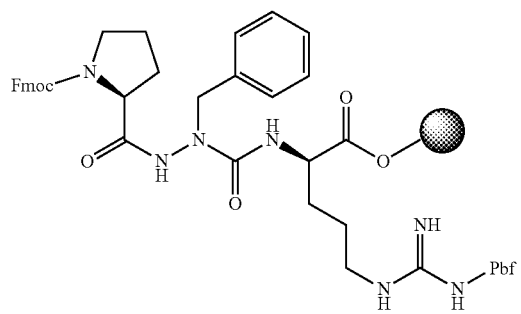
24
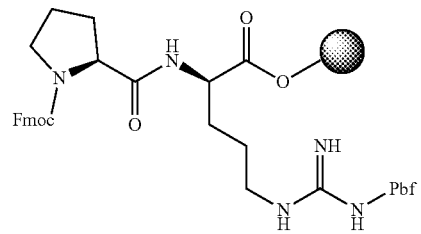
25
Scheme 3.
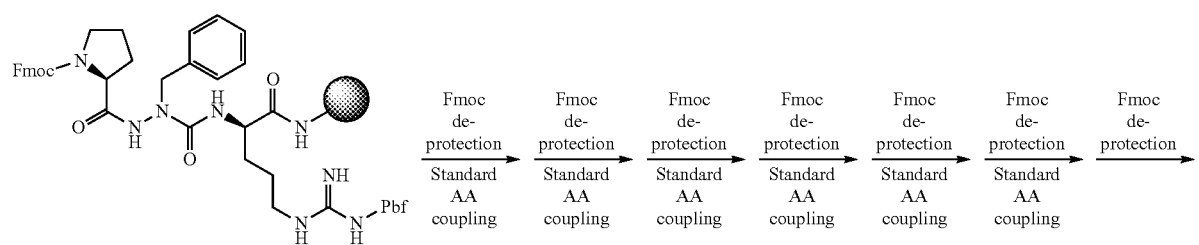

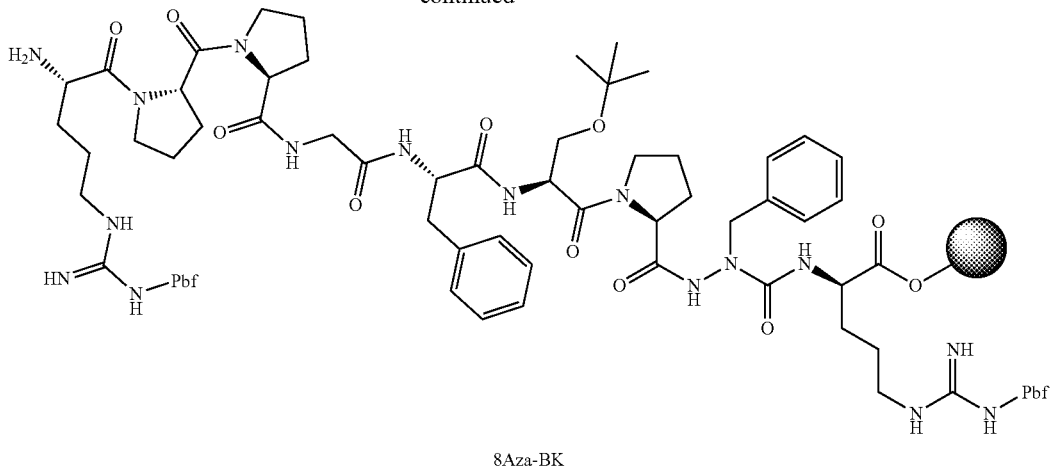

8Aza-BK

HPLC analysis is presented in FIGS. 1-3.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense. All documents cited herein, as well as text appearing in the figures, are hereby incorporated by reference in their entirety for all purposes to the same extent as if each were so individually denoted.

What is claimed is:

1. A compound of Formula (IA):

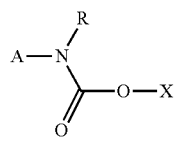

(IA)

wherein A is N-phthalimidyl or $NR_1R_2$,
$R_1$ is H,
$R_2$ is tert-butoxycarbonyl, 9-fluorenylmethoxycarbonyl, 2-(3,5-dimethoxyphenyl)propan-2-yloxycarbonyl, or
R and $R_1$ or $R_2$ are connected and together form a side chain radical of proline;
X is imidazolyl or benzotriazolyl; and
R is selected from the group consisting of H, methyl, isopropyl, isobutyl, benzyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine;
with the proviso that if A is $NR_1R_2$ and $R_2$ is 9-fluorenylmethoxycarbonyl, R is selected from the group consisting of H, isopropyl, isobutyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine.

2. The compound of claim 1, which is a compound of Formula (III):

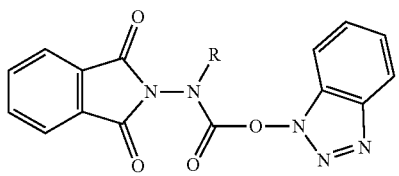

(III)

wherein R is selected from the group consisting H, methyl, isopropyl, isobutyl, benzyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine.

3. The compound of claim 1, which is a compound of Formula (II):

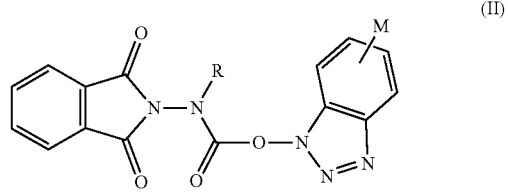

(II)

wherein R is selected from the group consisting of H, methyl, isopropyl, isobutyl, benzyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine; and M is a substituent selected from the group consisting of a halogen, a $C_1$-$C_6$ alkyl, hydroxyl, —COOH, —COH, methoxyl, ethoxyl, propoxyl, and a $C_1$-$C_6$ haloalkyl.

4. The compound of claim 1, wherein R is selected from the group consisting of methyl, isopropyl, isobutyl, benzyl, and side chain radicals of aspartic acid, histidine, glutamic acid, tryptophan, threonine, lysine, methionine, tyrosine, R-isoleucine, S-isoleucine, RS-isoleucine, arginine, glycine, asparagine, serine, and glutamine is unsubstituted.

5. The compound of claim 1, wherein R is substituted with one or more of the following: a halogen, a $C_1$-$C_6$ alkyl, hydroxyl, —COOH, —COH, methoxyl, ethoxyl, propoxyl, a $C_1$-$C_6$ haloalkyl, or a protecting group.
6. The compound of claim 1, wherein the compound is selected from the group consisting of:
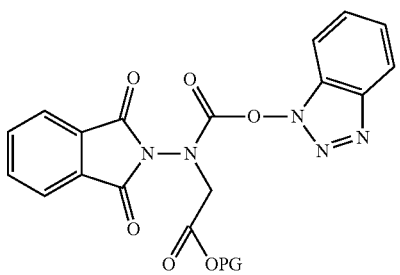
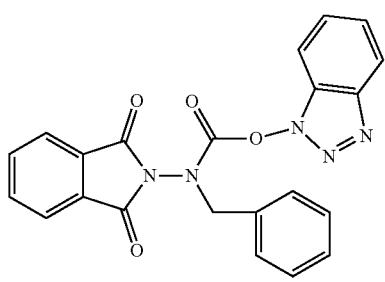 [SMILES: O=C(On1nnc2ccccc21)N(Cc1ccccc1)N1C(=O)c2ccccc2C1=O]
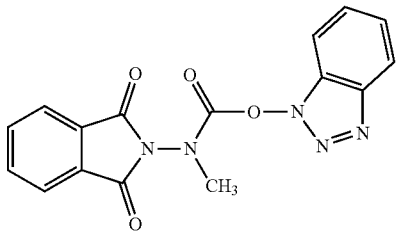 [SMILES: CN(C(=O)On1nnc2ccccc21)N1C(=O)c2ccccc2C1=O]
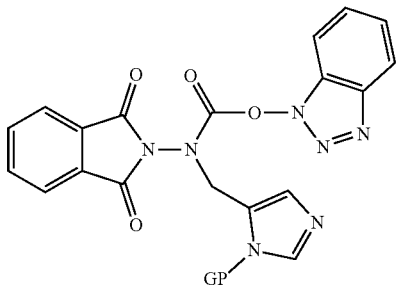
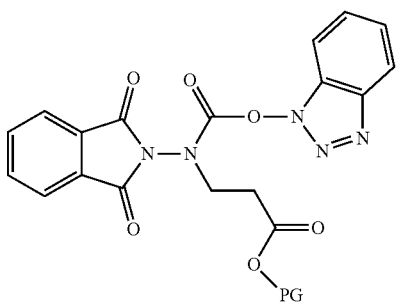
-continued
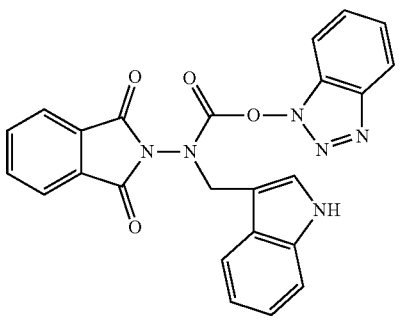 [SMILES: O=C(On1nnc2ccccc21)N(Cc1c[nH]c2ccccc12)N1C(=O)c2ccccc2C1=O]
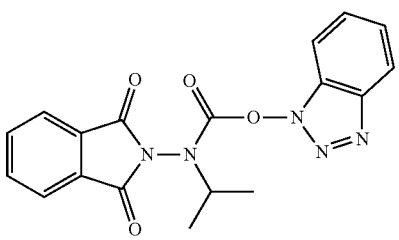 [SMILES: CC(C)N(C(=O)On1nnc2ccccc21)N1C(=O)c2ccccc2C1=O]
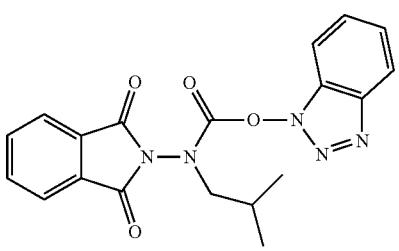 [SMILES: CC(C)CN(C(=O)On1nnc2ccccc21)N1C(=O)c2ccccc2C1=O]
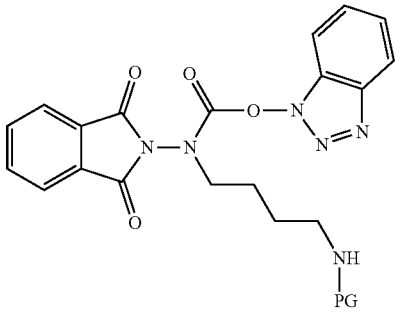
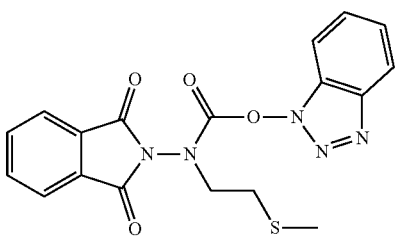 [SMILES: CSCCN(C(=O)On1nnc2ccccc21)N1C(=O)c2ccccc2C1=O]

-continued

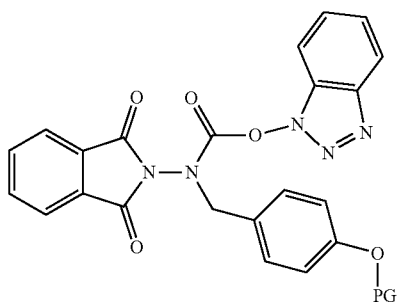

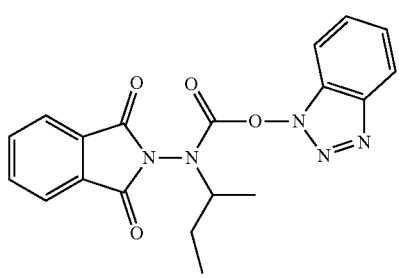 [SMILES: CCC(C)N(C(=O)On1nnc2ccccc21)N1C(=O)c2ccccc2C1=O]

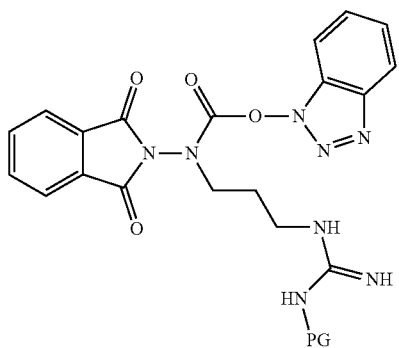

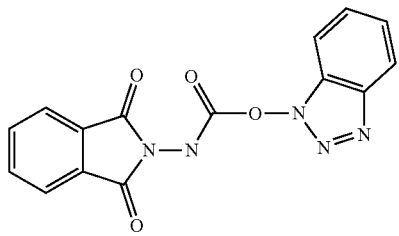 [SMILES: O=C(NN1C(=O)c2ccccc2C1=O)On1nnc2ccccc21]

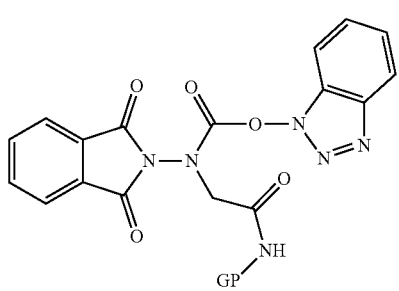

-continued

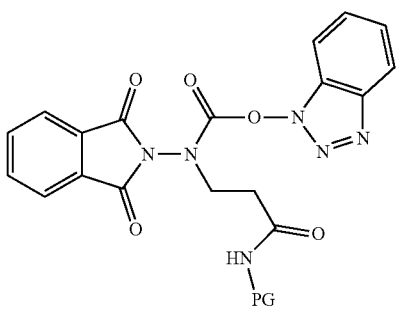

and pharmaceutically acceptable salts thereof, wherein PG is selected from the group consisting of H, N-phthalimidyl, tert-butoxycarbonyl, 9-fluorenylmethoxycarbonyl, and 2-(3, 5-dimethoxyphenyl)propan-2-yloxycarbonyl.

7. The compound of claim 6, wherein the PG is N-phthalimidyl.

8. The compound of claim 6, wherein the compound is selected from the group consisting of N-(((1H-benzo[d][1,2,3]triazol-1-yl)oxy)carbonyl)-N-(1,3-dioxoisoindolin-2-yl) glycine, 1H-benzo[d][1,2,3]triazol-1-yl benzyl(1,3-dioxoisoindolin-2-yl)carbamate, 1H-benzo[d][1,2,3]triazol-1-yl (1,3-dioxoisoindolin-2-yl)(methyl)carbamate, 1H-benzo[d][1,2,3]triazol-1-yl ((1H-pyrrol-2-yl)methyl)(1,3-dioxoisoindolin-2-yl)carbamate, 3-((((1H-benzo[d][1,2,3]triazol-1-yl)oxy)carbonyl)(1,3-dioxoisoindolin-2-yl)amino)propanoic acid, 1H-benzo[d][1,2,3]triazol-1-yl ((1H-indol-3-yl)methyl)(1,3-dioxoisoindolin-2-yl)carbamate, 1H-benzo[d][1,2,3]triazol-1-yl (1,3-dioxoisoindolin-2-yl)(isopropyl)carbamate (Phth-aza-valine-carbamoyl-O-benzotriazole), 1H-benzo[d][1,2,3]triazol-1-yl (1,3-dioxoisoindolin-2-yl)(isobutyl)carbamate, 1H-benzo[d][1,2,3]triazol-1-yl (4-aminobutyl)(1,3-dioxoisoindolin-2-yl)carbamate, 1H-benzo[d][1,2,3]triazol-1-yl (1,3-dioxoisoindolin-2-yl)(2-(methylthio)ethyl)carbamate, 1H-benzo[d][1,2,3]triazol-1-yl (1,3-dioxoisoindolin-2-yl)(4-hydroxybenzyl)carbamate, 1H-benzo[d][1,2,3]triazol-1-yl sec-butyl(1,3-dioxoisoindolin-2-yl)carbamate, 1H-benzo[d][1,2,3]triazol-1-yl (1,3-dioxoisoindolin-2-yl)(3-guanidinopropyl)carbamate, 1H-benzo[d][1,2,3]triazol-1-yl (1,3-dioxoisoindolin-2-yl)carbamate, 1H-benzo[d][1,2,3]triazol-1-yl (2-amino-2-oxoethyl)(1,3-dioxoisoindolin-2-yl)carbamate, 1H-benzo[d][1,2,3]triazol-1-yl (3-amino-3-oxopropyl)(1,3-dioxoisoindolin-2-yl)carbamate, and pharmaceutically acceptable salts thereof.

9. The compound of claim 1, wherein the compound is selected from the group consisting of:

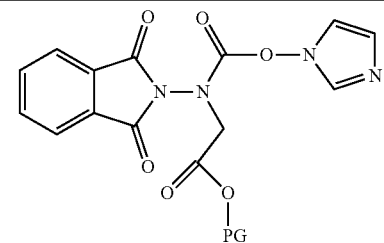

| 93 -continued | 94 -continued |
|---|---|
| 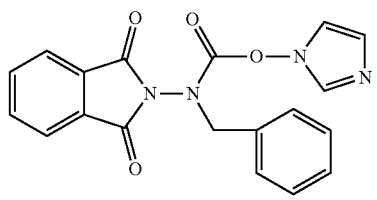 [SMILES: O=C(On1ccnc1)N(Cc1ccccc1)N1C(=O)c2ccccc2C1=O] | 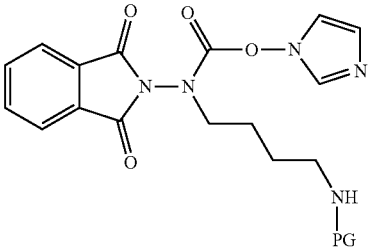 |
| 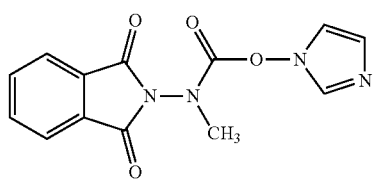 [SMILES: CN(C(=O)On1ccnc1)N1C(=O)c2ccccc2C1=O] | 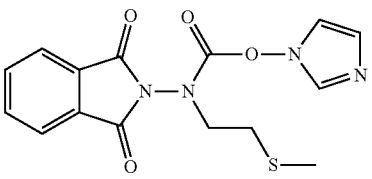 |
| 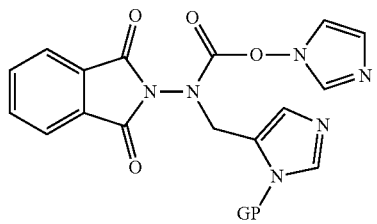 | 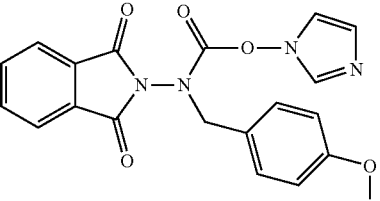 |
| 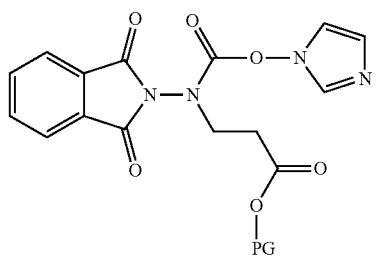 | 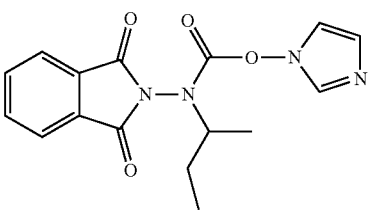 |
| 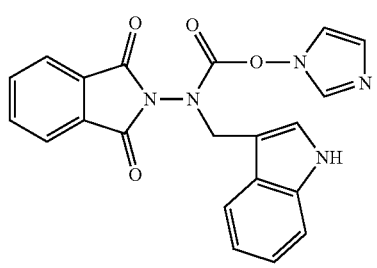 [SMILES: O=C(On1ccnc1)N(Cc1c[nH]c2ccccc12)N1C(=O)c2ccccc2C1=O] | 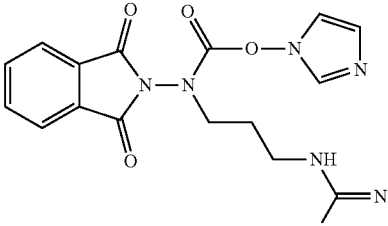 |
| 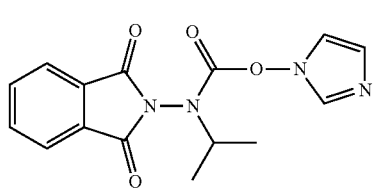 [SMILES: CC(C)N(C(=O)On1ccnc1)N1C(=O)c2ccccc2C1=O] | 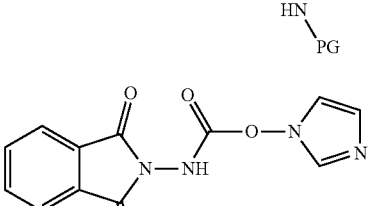 |
| 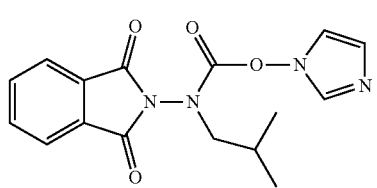 [SMILES: CC(C)CN(C(=O)On1ccnc1)N1C(=O)c2ccccc2C1=O] | 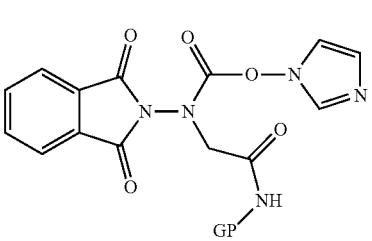 |

-continued

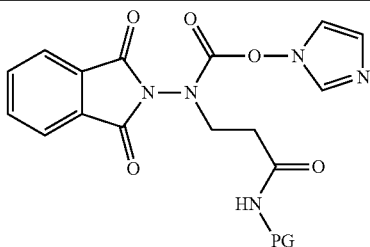

and pharmaceutically acceptable salts thereof, wherein PG is selected from the group consisting of H, N-phthalimidyl, tert-butoxycarbonyl, 9-fluorenylmethoxycarbonyl, 2-(3,5-dimethoxyphenyl)propan-2-yloxycarbonyl.

10. The compound of claim 9, wherein the PG is N-phthalimidyl.

11. The compound of claim 9, which is selected from the group consisting of N-(((1H-imidazol-1-yl)oxy)carbonyl)-N-(1,3-dioxoisoindolin-2-yl)glycine, 1H-imidazol-1-yl benzyl(1,3-dioxoisoindolin-2-yl)carbamate, 1H-imidazol-1-yl (1,3-dioxoisoindolin-2-yl)(methyl)carbamate, 1H-imidazol-1-yl ((1H-pyrrol-2-yl)methyl)(1,3-dioxoisoindolin-2-yl)carbamate, 3-((((1H-imidazol-1-yl)oxy)carbonyl)(1,3-dioxoisoindolin-2-yl)amino)propanoic acid, 1H-imidazol-1-yl ((1H-indol-3-yl)methyl)(1,3-dioxoisoindolin-2-yl)carbamate, 1H-imidazol-1-yl (1,3-dioxoisoindolin-2-yl)(isopropyl)carbamate, 1H-imidazol-1-yl (1,3-dioxoisoindolin-2-yl)(isobutyl)carbamate, 1H-imidazol-1-yl (4-aminobutyl)(1,3-dioxoisoindolin-2-yl)carbamate, 1H-imidazol-1-yl (1,3-dioxoisoindolin-2-yl)(2-(methylthio)ethyl)carbamate, 1H-imidazol-1-yl (1,3-dioxoisoindolin-2-yl)(4-hydroxybenzyl)carbamate, 1H-imidazol-1-yl sec-butyl(1,3-dioxoisoindolin-2-yl)carbamate, 1H-imidazol-1-yl (1,3-dioxoisoindolin-2-yl)(3-guanidinopropyl)carbamate, 1H-imidazol-1-yl (1,3-dioxoisoindolin-2-yl)carbamate, 1H-imidazol-1-yl (2-amino-2-oxoethyl)(1,3-dioxoisoindolin-2-yl)carbamate, 1H-imidazol-1-yl (3-amino-3-oxopropyl)(1,3-dioxoisoindolin-2-yl)carbamate, and pharmaceutically acceptable salts thereof.

12. A method of preparing an azapeptide comprising
a step of activating a compound according to claim 1; and
a step of coupling the activated compound with N-terminal of an amino acid, N-terminal of an aza-mino acid;
wherein the azapeptide is a compound of Formula (V):

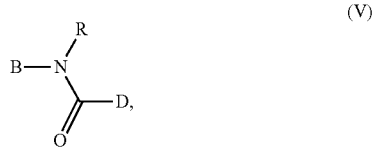

wherein

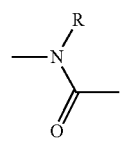

is at the N-terminus and/or the C-terminus of the compound of Formula (V), is adjacent to the N-terminus and/or the C-terminus of the compound of Formula (V) or hydrolysis site of the compound of Formula (V);

B is selected from the group consisting of hydrogen, $-NH_2$, $-NNH_2$, $-CONH_2$, $-COOR_3$, $-COOH$, $-COH$, $-COC_1-C_4$ alkyl, $-COC_1-C_4$ haloalkyl, $-OH$, an amino acid, an aza amino acid, a 2 to 60-mer peptide, a 2 to 60-mer aza peptide, a 2 to 60-mer azatide, D is selected from the group consisting of $-OR_4$, $-OH$, $-NH_2$, $-NNH_2$, $-NHCOCH_3$, $-NHCH_3$, $-N(CH_3)_2$, $-CONH_2$, $-COOH$, $-COH$, $-COC_1-C_4$ alkyl, $-COC_1-C_4$ haloalkyl, an amino acid, an aza amino acid, a 2 to 60-mer peptide, a 2 to 60-mer aza peptide, a 2 to 60-mer azatide, $R_3$ and $R_4$ is each independently selected from the group consisting of $C_1-C_6$ alkyl, methoxyl, ethoxyl, propoxyl, a $C_1-C_6$ haloalkyl and protecting groups, R is selected from the group consisting of side chain radicals of aspartic acid, phenylalanine, alanine, histidine, glutamic acid, tryptophan, valine, leucine, lysine, methionine, tyrosine, isoleucine, arginine, glycine, asparagine, serine, threonine, cysteine, and glutamine.

13. The method of claim 12, wherein the compound of claim 1 is substituted with one or more of the following: a halogen, a $C_1-C_6$ alkyl, hydroxyl, $-COOH$, $-COH$, methoxyl, ethoxyl, propoxyl, or a $C_1-C_6$ haloalkyl.

14. The method of claim 12, wherein the compound according to claim 1 is activated by iodomethane.

15. The method of claim 12, wherein said coupling is in acetonitrile.

16. The method of claim 9, wherein DIPEA is added to the acetonitrile.

17. The method of claim 16, wherein said coupling is during solid phase azapeptide synthesis.

18. The method of claim 12, wherein said coupling is during liquid phase azapeptide synthesis.

19. The method of claim 12, wherein the azapeptide is produced in a yield of at least about 50%.

20. The compound of claim 1, wherein
A is N-phthalimidyl,
X is imidazolyl or benzotriazolyl, and
R is selected from the group consisting of H, methyl, isopropyl, isobutyl, benzyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine.

21. The compound of claim 1, wherein A is $NR_1R_2$,
$R_1$ is H,
$R_2$ is 9-fluorenylmethoxycarbonyl,
X is imidazolyl or benzotriazolyl, and
R is selected from the group consisting of H, isopropyl, isobutyl, and side chain radicals of aspartic acid, histidine, glutamic acid, tryptophan, lysine, methionine, tyrosine, threonine, R-isoleucine, S-isoleucine, RS-isoleucine, arginine, glycine, asparagine, serine, and glutamine.

* * * * *